(12) United States Patent
Weinhold et al.

(10) Patent No.: US 8,129,106 B2
(45) Date of Patent: Mar. 6, 2012

(54) SEQUENCE-SPECIFIC DETECTION OF METHYLATION IN BIOMOLECULES

(75) Inventors: Elmar Weinhold, Aachen (DE);
Thomas Meier, München (DE);
Hartmut Düfel, Schlehdorf (DE);
Christine Markert-Hahn, Penzberg (DE); Rainer Schmuck, Benediktbeuern (DE)

(73) Assignee: Max-Planck-Geselischaft zur Forderung der Wissenschaften E.V., Berlin (DE)

( * ) Notice: Subject to any disclaimer, the term of this patent is extended or adjusted under 35 U.S.C. 154(b) by 1156 days.

(21) Appl. No.: 11/570,672

(22) PCT Filed: Jun. 14, 2005

(86) PCT No.: PCT/EP2005/006374
§ 371 (c)(1),
(2), (4) Date: Nov. 5, 2007

(87) PCT Pub. No.: WO2005/121361
PCT Pub. Date: Dec. 22, 2005

(65) Prior Publication Data
US 2011/0165564 A1     Jul. 7, 2011

(30) Foreign Application Priority Data

Jun. 14, 2004  (EP) .................................... 04013894

(51) Int. Cl.
C12Q 1/68 (2006.01)
C12Q 1/70 (2006.01)
G01N 33/53 (2006.01)
C07H 15/00 (2006.01)
C07H 21/04 (2006.01)
C07H 19/04 (2006.01)

(52) U.S. Cl. .................. 435/6; 435/5; 435/7.1; 435/7.2; 536/4.1; 536/24.3; 536/26.6

(58) Field of Classification Search .................. 435/5, 6, 435/7.1, 7.2; 536/4.1, 24.3, 26.6
See application file for complete search history.

(56) References Cited

U.S. PATENT DOCUMENTS 6,875,750 B1    4/2005  Pignot et al.
2003/0129602 A1*  7/2003  Huang .............................. 435/6

FOREIGN PATENT DOCUMENTS

FR       2548190        1/1985
WO     WO 00/06587       2/2000

OTHER PUBLICATIONS

Weller, R. L et al, "Aziridination of [gamma], [delta]-dibromoethyl-1-pentenoate with primary amines: Extension of the Gabriel-Comwell reaction", Tetrahedron Letters, Jul. 19, 2004, UK, vol. 45, No. 30, pp. 5807-5810.

* cited by examiner

Primary Examiner — Jezia Riley
(74) Attorney, Agent, or Firm — Baker Donelson Bearman Caldwell & Berkowitz, PC

(57) ABSTRACT

A method for detecting sequence specific methylation in a biomolecule, comprising: (a) contacting the biomolecule with an S-adenosyl-L-methionine-dependent methyltransferase in the presence of a detectable cofactor of said methyltransferase; and (b) detecting whether the recognition sequence of said methyltransferase has been modified with the cofactor or a derivative thereof, wherein modification of the recognition sequence of said methyltransferase is indicative of an absence of methylation at said recognition sequence. Also disclosed is a cofactor specific for S-adenosyl-L-methionine-dependent methyltransferases, wherein said cofactor is an N-adenosylaziridine derivative with a reporter group attached to the 6 or 7 position of the adenine ring or attached to the aziridine ring. A complex of the cofactor and a methyltransferase a composition comprising the cofactor or the complex and the use of the cofactor or the complex for detecting sequence-specific methylation in DNA molecules are also disclosed.

34 Claims, 15 Drawing Sheets

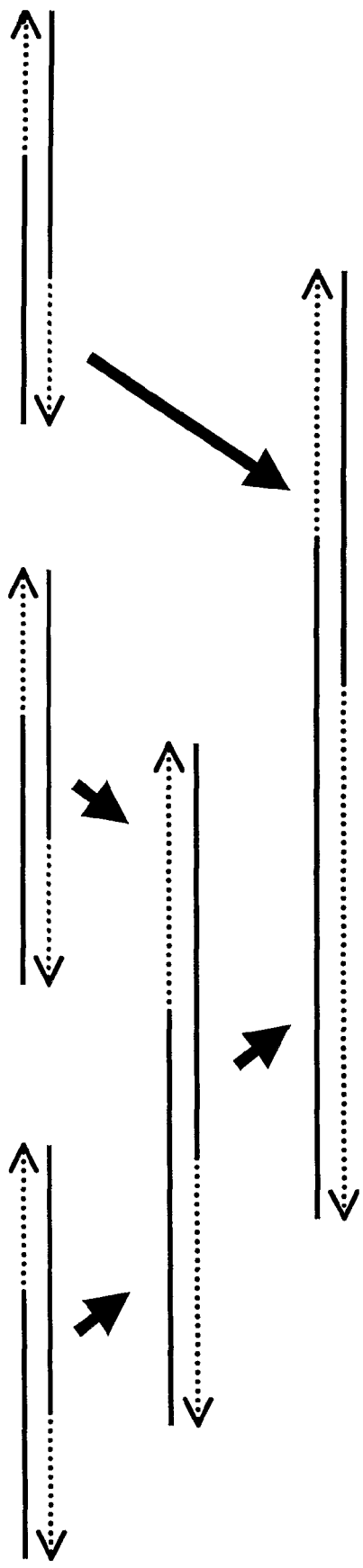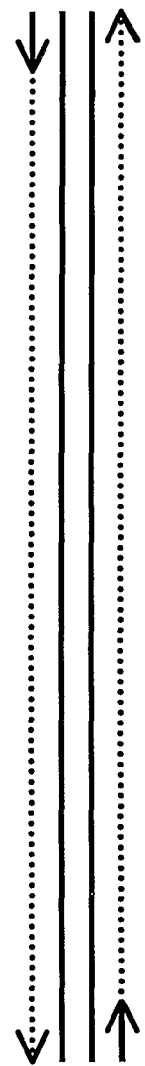
Step 1:
Annealing of overlapping primer pairs and completion of the double strand by PCR
Step 2:
Amplification of the entire fragment by using standard PCR primers
Figure 7

| | | |
|---|---|---|
| SssI-Substrate 23 | ttccccggcccagtgcgcggactccggggactccaggggcgccctctg | |
| PCR-Product 1 | ttccccggcccagtgcgcggactccggggactccaggggcgccctctg | |
| SssI- Substrate 73 | cgcccgacgcgccccggggtgcagcggcgcgccgggggctgggggccggcggggagt | |
| PCR-Product 51 | cgcccgacgcgccggggtgcagcggcgcgccgggggctgggggccggcggggagt | |
| SssI-Substrate 123 | ccgtgcgaccctccagaagagcgcccggcgccgtgactcagcactgggc | |
| PCR-Product 101 | ccggcgaccctccagaagagcgcccggcgccgtgactcagcactgggc | |
| SssI-Substrate 173 | gcagcggggcgggaccaccccttataaggctcggagggcgcgaggccttcg | |
| PCR-Product 151 | gcagcggggcgggaccaccccttataaggctcggagggcgcgaggccttag | |
| SssI-Substrate 223 | ctggagttgcgcgcgcagtcttcgccaccagtgagtacgcgcggcccg | |
| PCR-Product 201 | ctggagttgcgcgcgcagtcttcgccaccagtgagtacgcgcggcccg | |
| SssI-Substrate 273 | cgcccggggatggggctcagagctcc | |
| PCR-Product 251 | cgcccggggatggggctcagagctcc | |

⇒ sequencing without errors

Length of the substrate (incl. PCR-Primer): 320 bp
MW: 211,2 kDa
1 μg target-DNA = 4,7 pmol 40 CpG-sites (SssI-targets) => degree of methylation 100 %
12 GCGC-sites (HhaI-targets) => degree of methylation 30 %
7 CCGG-sites (HpaII-targets) => degree of methylation 17,5 %
20 HhaI + HpaII-targets => degree of methylation 47,5 %

Figure 8

Analysis of methylated/partially methylated DNA-substrate:

➢ after cleavage with the respective endonucleases, the substrate was purified and extracted, in order to obtain substrate which is (as much as possible) clean and free of by-products
➢ after a further cleavage step, purified substrate was analyzed on an agarose gel (2 % (w/v))

| lane | sample |
|---|---|
| 1 | SssI-methylated DNA, HhaI/HpaII |
| 2 | SssI- methylated DNA, BstUI |
| 3 | MW-Marker VIII (Roche) |
| 4 | HhaI- methylated DNA, HhaI |
| 5 | HpaII- methylated DNA, HpaII |
| 6 | HhaI/HpaII- methylated DNA, HhaI/HpaII |
| 7 | MW-Marker VIII (Roche) |
| 8 | non-methylated DNA |

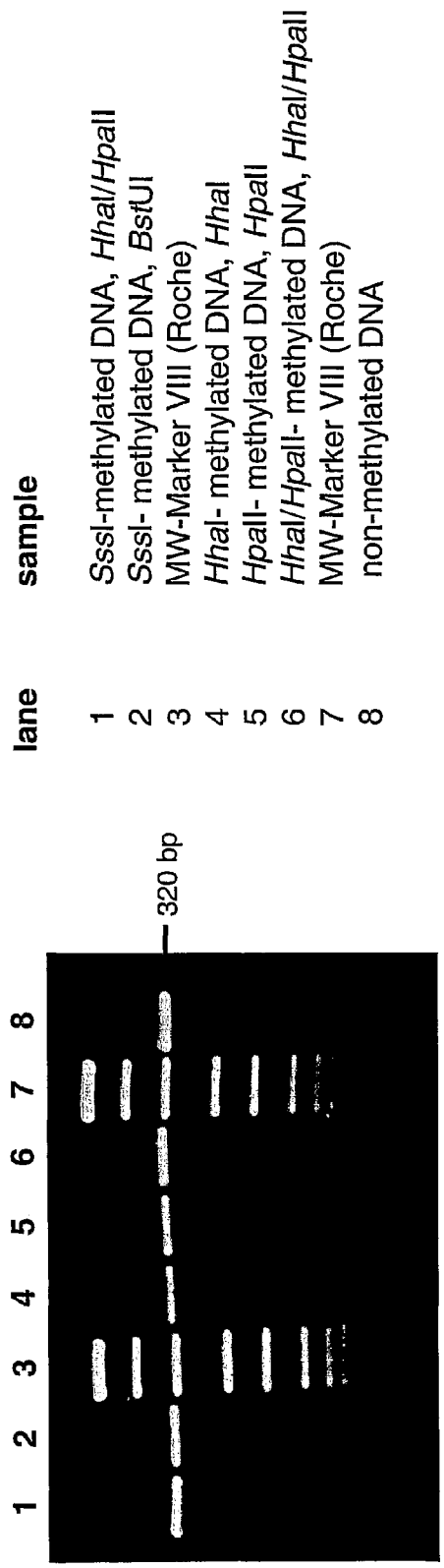

Figure 9B

SEQUENCE LISTING

```
<160> NUMBER OF SEQ ID NOS: 23

<210> SEQ ID NO 1
<211> LENGTH: 13
<212> TYPE: DNA
<213> ORGANISM: Artificial Sequence
<220> FEATURE:
<223> OTHER INFORMATION: oligodeoxynucleotide

<400> SEQUENCE: 1
tgtcagcgca tga                                                          13

<210> SEQ ID NO 2
<211> LENGTH: 13
<212> TYPE: DNA
<213> ORGANISM: Artificial Sequence
<220> FEATURE:
<223> OTHER INFORMATION: oligodeoxynucleotide
<220> FEATURE:
<221> NAME/KEY: modified_base
<222> LOCATION: (6)..(6)
<223> OTHER INFORMATION: 5-methyl-2'-deoxy-cytidine

<400> SEQUENCE: 2
tcatgcgctg aca                                                          13

<210> SEQ ID NO 3
<211> LENGTH: 13
<212> TYPE: DNA
<213> ORGANISM: Artificial Sequence
<220> FEATURE:
<223> OTHER INFORMATION: oligodeoxynucleotide

<400> SEQUENCE: 3
tcatgcgctg aca                                                          13

<210> SEQ ID NO 4
<211> LENGTH: 22
<212> TYPE: DNA
<213> ORGANISM: Artificial Sequence
<220> FEATURE:
<223> OTHER INFORMATION: oligodeoxynucleotide

<400> SEQUENCE: 4
gacctgggaa agagggaaag gc                                                22

<210> SEQ ID NO 5
<211> LENGTH: 19
```

```
<212> TYPE: DNA
<213> ORGANISM: Artificial Sequence
<220> FEATURE:
<223> OTHER INFORMATION: oligodeoxynucleotide

<400> SEQUENCE: 5
ctgcgggttg gccccatgc                                                    19

<210> SEQ ID NO 6
<211> LENGTH: 16
<212> TYPE: DNA
<213> ORGANISM: Artificial Sequence
<220> FEATURE:
<223> OTHER INFORMATION: oligodeoxynucleotide
<220> FEATURE:
<221> NAME/KEY: modified_base
<222> LOCATION: (1)..(1)
<223> OTHER INFORMATION: oligodeoxynucleotide is labeled at 5' end with
      LC Red640

<400> SEQUENCE: 6
ggcgcagcgg ggcggg                                                       16

<210> SEQ ID NO 7
<211> LENGTH: 17
<212> TYPE: DNA
<213> ORGANISM: Artificial Sequence
<220> FEATURE:
<223> OTHER INFORMATION: oligodeoxynucleotide
<220> FEATURE:
<221> NAME/KEY: modified_base
<222> LOCATION: (17)..(17)
<223> OTHER INFORMATION: 3' end of oligodeoxynucleotide is labeled with
      fluorescein

<400> SEQUENCE: 7
cgccgtgact cagcact                                                      17

<210> SEQ ID NO 8
<211> LENGTH: 28
<212> TYPE: DNA
<213> ORGANISM: Artificial Sequence
<220> FEATURE:
<223> OTHER INFORMATION: oligodeoxynucleotide

<400> SEQUENCE: 8
atgcgtgggt agttcgatgg tctagtct                                          28

<210> SEQ ID NO 9
<211> LENGTH: 28
<212> TYPE: DNA
<213> ORGANISM: Artificial Sequence
<220> FEATURE:
<223> OTHER INFORMATION: oligodeoxynucleotide

<400> SEQUENCE: 9
agactagacc atcgaactac ccacgcat                                          28

<210> SEQ ID NO 10
<211> LENGTH: 28
<212> TYPE: DNA
<213> ORGANISM: Artificial Sequence
<220> FEATURE:
<223> OTHER INFORMATION: oligodeoxynucleotide
<220> FEATURE:
<221> NAME/KEY: modified_base
<222> LOCATION: (4)..(4)
<223> OTHER INFORMATION: m5c
<220> FEATURE:
<221> NAME/KEY: modified_base
```

<222> LOCATION: (15)..(15)
<223> OTHER INFORMATION: m5c

<400> SEQUENCE: 10
atgcgtgggt agttcgatgg tctagtct                                          28

<210> SEQ ID NO 11
<211> LENGTH: 28
<212> TYPE: DNA
<213> ORGANISM: Artificial Sequence
<220> FEATURE:
<223> OTHER INFORMATION: oligodeoxynucleotide
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (24)..(24)
<223> OTHER INFORMATION: m5c

<400> SEQUENCE: 11
agactagacc atcgaactac ccacgcat                                          28

<210> SEQ ID NO 12
<211> LENGTH: 50
<212> TYPE: DNA
<213> ORGANISM: Artificial Sequence
<220> FEATURE:
<223> OTHER INFORMATION: oligodeoxynucleotide

<400> SEQUENCE: 12
ttccccggcc agctgcgcgg cgactccggg gactccaggg cgcccctctg                  50

<210> SEQ ID NO 13
<211> LENGTH: 50
<212> TYPE: DNA
<213> ORGANISM: Artificial Sequence
<220> FEATURE:
<223> OTHER INFORMATION: oligodeoxynucleotide

<400> SEQUENCE: 13
ttccccggcc agctgcgcgg cgactccggg gactccaggg cgcccctctg                  50

<210> SEQ ID NO 14
<211> LENGTH: 50
<212> TYPE: DNA
<213> ORGANISM: Artificial Sequence
<220> FEATURE:
<223> OTHER INFORMATION: oligodeoxynucleotide

<400> SEQUENCE: 14
cgcccgacgc ccggggtgca gcgggcgccg gggctggggc cggcgggagt                  50

<210> SEQ ID NO 15
<211> LENGTH: 50
<212> TYPE: DNA
<213> ORGANISM: Artificial Sequence
<220> FEATURE:
<223> OTHER INFORMATION: oligodeoxynucleotide

<400> SEQUENCE: 15
cgcccgacgc ccggggtgca gcgggcgccg gggctggggc cggcgggagt                  50

<210> SEQ ID NO 16
<211> LENGTH: 50
<212> TYPE: DNA
<213> ORGANISM: Artificial Sequence

```
<220> FEATURE:
<223> OTHER INFORMATION: oligodeoxynucleotide

<400> SEQUENCE: 16
ccgcgcgacc ctccagaaga gcgcccggcg ccgtgactca gcactggggc        50

<210> SEQ ID NO 17
<211> LENGTH: 50
<212> TYPE: DNA
<213> ORGANISM: Artificial Sequence
<220> FEATURE:
<223> OTHER INFORMATION: oligodeoxynucleotide

<400> SEQUENCE: 17
ccgcgcgacc ctccagaaga gcgcccggcg ccgtgactca gcactggggc        50

<210> SEQ ID NO 18
<211> LENGTH: 50
<212> TYPE: DNA
<213> ORGANISM: Artificial Sequence
<220> FEATURE:
<223> OTHER INFORMATION: oligodeoxynucleotide

<400> SEQUENCE: 18
gcagcggggc gggaccaccc ttataaggct cggagggcgc gaggccttcg        50

<210> SEQ ID NO 19
<211> LENGTH: 50
<212> TYPE: DNA
<213> ORGANISM: Artificial Sequence
<220> FEATURE:
<223> OTHER INFORMATION: oligodeoxynucleotide

<400> SEQUENCE: 19
gcagcggggc gggaccaccc ttataaggct cggagggcgc gaggccttcg        50

<210> SEQ ID NO 20
<211> LENGTH: 50
<212> TYPE: DNA
<213> ORGANISM: Artificial Sequence
<220> FEATURE:
<223> OTHER INFORMATION: oligodeoxynucleotide

<400> SEQUENCE: 20
ctggagttgc gccgccgcag tcttcgccac cagtgagtac gcgcggcccg        50

<210> SEQ ID NO 21
<211> LENGTH: 50
<212> TYPE: DNA
<213> ORGANISM: Artificial Sequence
<220> FEATURE:
<223> OTHER INFORMATION: oligodeoxynucleotide

<400> SEQUENCE: 21
ctggagttgc gccgccgcag tcttcgccac cagtgagtac gcgcggcccg        50

<210> SEQ ID NO 22
<211> LENGTH: 27
<212> TYPE: DNA
<213> ORGANISM: Artificial Sequence
<220> FEATURE:
<223> OTHER INFORMATION: oligodeoxynucleotide

<400> SEQUENCE: 22
cgccccgggg atggggctca gagctcc                                 27
```

```
<210> SEQ ID NO 23
<211> LENGTH: 27
<212> TYPE: DNA
<213> ORGANISM: Artificial Sequence
<220> FEATURE:
<223> OTHER INFORMATION: oligodeoxynucleotide

<400> SEQUENCE: 23
cgccccgggg atgggctca gagctcc                                            27
```

SEQUENCE-SPECIFIC DETECTION OF METHYLATION IN BIOMOLECULES

CROSS REFERENCE TO RELATED APPLICATIONS

This application is a 35 USC §371 National Stage application of International Application No. PCT/EP05/006374 filed Jun. 14, 2005 which claims priority to European Application No. 04013894.3 filed Jun. 14, 2004.

BACKGROUND AND SUMMARY OF THE INVENTION

The present invention relates to a method for detecting sequence-specific methylation in a biomolecule, comprising: (a) contacting a biomolecule with an S-adenosyl-L-methionine-dependent methyltransferase in the presence of a detectable cofactor of said methyltransferase; and (b) detecting whether the recognition sequence of said methyltransferase has been modified with the cofactor or a derivative thereof, wherein modification of the recognition sequence of said methyltransferase is indicative of an absence of methylation at said recognition sequence. The present invention also relates to a cofactor which is specific for S-adenosyl-L-methionine-dependent methyltransferases, wherein said cofactor is an N-adenosylaziridine derivative with a reporter group attached to the 6 or 7 position of the adenine ring or attached to the aziridine ring. Moreover, the present invention relates to a complex of the cofactor of the present invention and a methyltransferase which normally uses S-adenosyl-L-methionine (AdoMet) as a cofactor. In addition, the present invention relates to a diagnostic composition comprising the cofactor of the present invention or the complex of the present invention. Finally, the present invention relates to the use of the cofactor of the present invention or the complex of the present invention for detecting sequence-specific methylation in DNA molecules.

Several documents are cited throughout the text of this specification. The disclosure content of the documents cited therein (including manufacture's specifications, instructions, etc.) is herewith incorporated by reference.

Any combination of steps (including single steps only) carried out in vitro and cited throughout this specification can also be carried out with cell extracts or in vivo.

The present invention is exemplified using DNA methylation found in humans. However, it can also be used to detect DNA methylation in other organisms as well as RNA methylation and protein methylation.

DNA methylation is found in almost all organisms (Jeltsch, (2002) ChemBioChem 3, 275-293). The DNA can contain the methylated nucleobases 5-methylcytosine (5-mCyt), N4-methylcytosine (4-mCyt) or N6-methyladenine (6-mAde) in addition to cytosine, adenine, thymine and guanine. These methylated nucleobases are formed by DNA methyltransferases (MTases) which catalyze the transfer of the activated methyl group from the cofactor S-adenosyl-L-methionine (AdoMet) to the C5 carbon of cytosine, the N4 nitrogen of cytosine or the N6 nitrogen of adenine within their DNA recognition sequences (Cheng, (1995) Annu. Rev. Biophys. Biomol. Struct. 24, 293-318). Since a particular nucleotide sequence may exist in its methylated or unmethylated form, DNA methylation can be regarded as an increase of the information content of DNA, which serves a wide variety of biological functions. In prokaryotes DNA methylation is involved in protection of the host genome from endogenous restriction endonucleases, DNA mismatch repair, regulation of gene expression and DNA replication. In eukaryotes DNA methylation plays a role in important regulatory processes such as gene silencing (Bird, (2002) Genes Dev. 16, 6-21, genomic imprinting (Feil and Khosla, (1999) Trends Genet. 15, 431-435), X-chromosome inactivation (Panning and Jaenisch, (1998) Cell 93, 305-308), silencing of intragenomic parasites (Yoder, (1997) Trends Genet. 13, 335-340), and carcinogenesis (Baylin, (1998) Adv. Cancer Res. 72, 141-196; Jones and Laird, (1999) Nat. Genet. 21, 163-167). Success of cancer treatments, in general, depends to a large extent on an early diagnosis of tumorgenesis. Therefore, there is an important need to develop early assays of general tumorgenesis.

It is considered that a number of particular forms of cancer are associated with changes in the regulation of gene expression. In many cases, the changes of gene expression can be traced back to an altered methylation pattern of chromosomal DNA. For a long time it was known that DNA methylation is a mechanism for altering gene expression without altering the coding function of a gene. The methylation reaction involves transfer of a methyl group from S-adenosyl-L-methionine (AdoMet) in a cleft of the enzyme DNA (cytosine-5)-methyltransferase to form 5-methylcytosine (5-mCyt). Interestingly, 5-methylcytosines are not evenly distributed in the chromosomal DNA but tend to be located to CpG dinucleotides. The mammalian genome contains few isolated CpG dinucleotides which are largely methylated (Larsen, et al., (1992) Genomics 13, 1095-1107). More frequently observed are dinucleotide clusters of CpG's or "CpG islands" (Gardiner-Garden and Frommer, (1987) J. Mol. Biol. 196, 261-282) which are present in the promoter and exonic regions of approximately 40% of mammalian genes. CpG islands are areas of the genome, typically between 0.2 to about 1 kb in length, which are enriched in cytosines and guanines relative to the genome. CpG islands have been shown to be associated with the 5' ends of all housekeeping genes and many tissue-specific genes, and with the 3' ends of some tissue-specific genes. The 5' CpG islands may extend through 5'-flanking DNA, exons and introns, whereas most of the 3' CpG islands appear to be associated with exons. CpG islands are generally found in the same position relative to the transcription unit of equivalent genes in different species, with some notable exceptions (Gardiner-Garden and Frommer, (1987) J. Mol. Biol. 196, 261-82).

Methylation of cytosine residues contained within CpG islands of certain genes has been inversely correlated with gene activity. It is conceivable that this could lead to a decreased gene expression by a variety of mechanisms such as a local condensation of chromatin structure, inhibition of transcription factor-DNA binding, or by recruiting proteins which specifically interact with methylated CpGs indirectly preventing transcription factor binding. Increased methylation may also affect, e.g., the promoter region of tumor suppressor genes. Increased methylation in such regions may lead to progressive reduction of normal gene expression resulting in a population of cells having a selective growth advantage.

It is, however, not simply an increased methylation of DNA that is observed in cancer cells. Rather, distinct changes in the methylation pattern of DNA might be sufficient to alter gene expression in the cell and to induce carcinogenesis. In fact, it has been shown that cancer cells are associated with a characteristic pattern of CpG-methylation, distinct from the methylation pattern of their healthy progenitor cell. Hence, knowledge of the specific methylation pattern of chromosomal DNA of healthy and diseased cells can be exploited for developing markers that can be used for detection of diseases such as cancer.

Mapping of methylated regions in DNA (Rein et al., (1998) Nucleic Acids Res. 26, 2255-2264) has primarily relied on Southern hybridization approaches, based on the inability of methylation-sensitive restriction enzymes to cleave sequences which contain one or more methylated CpG sequences. This method provides for an assessment of the overall methylated status of CpG islands, including some quantitative analysis, but is relatively insensitive, requires large amounts of sample and can only provide information about those CpG sequences found within sequences recognized by methylation-sensitive restriction enzymes.

A more sensitive approach is based on the detection of methylated patterns by using a combination of methylation sensitive enzymes and the polymerase chain reaction (PCR). After digestion of DNA with the enzyme, PCR will amplify from primers flanking the restriction sequence only if DNA cleavage was prevented by methylation. Like Southern-based approaches, this method can only monitor CpG-methylation in methylation-sensitive restriction sites. Another method that avoids the use of restriction endonucleases utilizes bisulfite treatment of DNA to convert all unmethylated cytosines to uracils. The altered DNA is amplified and sequenced to show the methylation status of all CpG sequences. Alternatively, the amplified DNA can be analyzed in hybridization experiments.

The major disadvantage of the approaches of the prior art is that the primary modification of native DNA does not directly lead to incorporation of a detectable label which strongly restricts applicable methods for the following detection step.

Recently, a novel approach for sequence-specific labelling of DNA using a newly designed fluorescent cofactor for the DNA (adenine-6)-methyltransferase from *Thermus aquaticus* (M.TaqI) has been presented (Pljevaljcic et al., (2003) J. Am. Chem. Soc. 125, 3486-3492). Naturally, M.TaqI catalyze the nucleophilic attack of the exocyclic amino group of adenine within the double-stranded 5'-TCGA-3' DNA sequence onto the methyl group of the cofactor S-adenosyl-L-methionine (AdoMet) leading to sequence- and base-specific methyl group transfer. Most importantly, M.TaqI, like other DNA methyltransferases (MTases) can only transfer one methyl group to its target base and DNA with a fully methylated recognition sequence is not further modified.

Replacement of the methionine side chain of the natural cofactor S-adenosyl-L-methionine (AdoMet) by an aziridinyl residue leads to M.TaqI-catalyzed nucleophilic ring opening and coupling of the whole nucleoside to the target adenine in DNA. The adenosyl moiety is the molecular anchor for cofactor binding. Attachment of a fluorophore via a flexible linker to the 8-position of the adenosyl moiety does not block cofactor binding. The newly designed cofactor, 8-amino[1"-(N"-dansyl)-4"-aminobutyl]-5'-(1-aziridinyl)-5'-deoxyadenosine, can be used to sequence-specifically label DNA in a M.TaqI-catalyzed reaction.

It would be desirable to use the newly designed fluorescent cofactor for labelling reactions catalyzed by DNA (cytosine-5)-methyltransferases with a recognition sequence embracing the CpG motif of CpG islands. Since methylation of cytosine residues should block enzymatic coupling of the labelled cofactor, a successful labelling reaction would be indicative of a non-methylated CpG sequence, whereas a failure to couple a labelled cofactor would be indicative of a methylated CpG sequence. Thus, this reaction could be used to monitor the methylation status of chromosomal DNA.

*Haemophilus haemolyticus* naturally produces a DNA (cytosine-5)-methyltransferase, M.HhaI, with the required specificity and methylates the first cytosine within the double-stranded DNA sequence 5'-GCGC-3'. However, no detectable N-adenosyl-aziridine cofactors or derivatives of M.HhaI are available in the art. Therefore, the technical problem underlying the teaching of the present application was to provide a detectable cofactor for M.HhaI and other S-adenosyl-L-methionine-dependent methyltransferases and methods for detecting alterations in the methylation status of DNA.

The solution to this technical problem is achieved by providing the embodiments characterized in the claims.

Accordingly the present invention relates to a method for detecting sequence-specific methylation in a biomolecule, comprising: (a) contacting a biomolecule with an S-adenosyl-L-methionine-dependent methyltransferase in the presence of a detectable cofactor of said methyltransferase; and (b) detecting whether the recognition sequence of said methyltransferase has been modified with the cofactor or a derivative thereof, wherein modification of the recognition sequence of said methyltransferase is indicative of an absence of methylation at said recognition sequence, wherein the N-adenosylaziridine derivative is represented by formula (I),

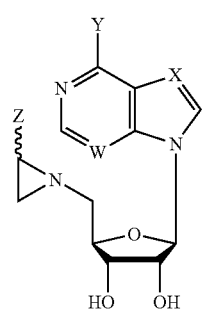

(I)

wherein
W is selected from N and CH,
X is N or $CR^1$,
Y is $NH_2$ or $NHR^2$,
Z is H, $R^3$ or $CH_2CH(COOH)(NH_2)$,
with the proviso that
if X is $CR^1$, Y is $NH_2$ and Z is H or $CH_2CH(COOH)(NH_2)$,
if X is N and Y is $NHR^2$, Z is H or $CH_2CH(COOH)(NH_2)$,
if X is N and Y is $NH_2$, Z is $R^3$,
$R^1$ is selected from —$(CH_2)_nR^4$, —$(CH=CH)_m(CH_2)_nR^4$, —$(CH_2)_o(CH=CH)_m(CH_2)_nR^4$, —$(C≡C)_m(CH_2)_nR^4$, —$(C)_m(C_6H_4)_o(CH_2)_nR^4$, —$(C_6H_4)_m(CH_2)_nR^4$, —$CO(CH_2)_nR^4$ and —$S(CH_2)_nR^4$;
$R^2$ is selected from —$(CH_2)_nR^4$, —$(C_6H_4)_m(CH_2)_nR^4$, —$CO(C_6H_4)_m(CH_2)_nR^4$ and —$CO(CH_2)_nR^4$;
$R^3$ is selected from —$(CH_2)_nR^4$, —$(CH=CH)_m(CH_2)_nR^4$, —$(C≡C)_m(CH_2)_nR^4$, —$(C_6H_4)_m(CH_2)_nR^4$ and —$CONH(CH_2)_nR^4$;
$R^4$ is selected from —$NHR^5$, —$NHCO(CH_2)_pSR^5$, —$SR^5$, —$OR^5$, —$O(C_2H_5O)_n(C_2H_5)NHR^5$, —$CH_2NHNHR^5$, —$NHCOCH(CH_2SH)NHR^5$ and —$CONHR^5$;
$R^5$ is selected from fluorophores, affinity tags, crosslinking agents, chromophors, proteins, peptides, amino acids which may optionally be modified, nucleotides, nucleosides, nucleic acids, carbohydrates, lipids, PEG, transfection reagents, beads, intercalating agents, nucleic acid cleaving reagents and nanoparticles (e.g. gold cluster) and
n, m, o and p are independently selected from 0 or an integer from 1 to 5000.

The term "detecting sequence specific methylation", as used throughout the invention, means to assess whether the acceptor site within the recognition sequence of a methyltransferase (MTase) is modified by the addition of a methyl group. Preferably, said acceptor site is part of the recognition sequence of a DNA methyltransferase. More preferably, said DNA methyltransferase is selected from M.HhaI and M.TaqI, M.BseCI and M. SssI. When the DNA methyltransferase is M.HhaI, it is preferred that the acceptor site is cytosine within the 5'-CG-3' sequence which is embedded into the larger 5'-GCGC-3' recognition sequence of M.HhaI.

The term "biomolecule" means DNA, RNA or (poly)peptide. The term "(poly)peptide" refers alternatively to peptide or to polypeptide. Peptides conventionally are covalently linked amino acids of up to 30 residues, whereas polypeptides (also referred to as "proteins") comprise 31 and more amino acid residues. Preferably, the biomolecule is chromosomal or genomic DNA.

The term "contacting a biomolecule with a methyltransferase" means bringing into contact the biomolecule with the methyltransferase. Generally, this may be done by adding the methyltransferase to a sample containing the biomolecule. Alternatively, the sample containing the biomolecule may be added to a solution containing the methyltransferase. The skilled person knows that particular buffer conditions might be required for optimal enzyme activity. These conditions are either known to the skilled person or can be obtained by studying enzyme activity under various assay conditions.

BRIEF DESCRIPTION OF THE DRAWINGS

FIG. 7: Synthesis of substrate by overlap-extension-PCR.

FIG. 8: Sequence analysis of the DNA substrate.

DESCRIPTION OF THE INVENTION

Figure 1:
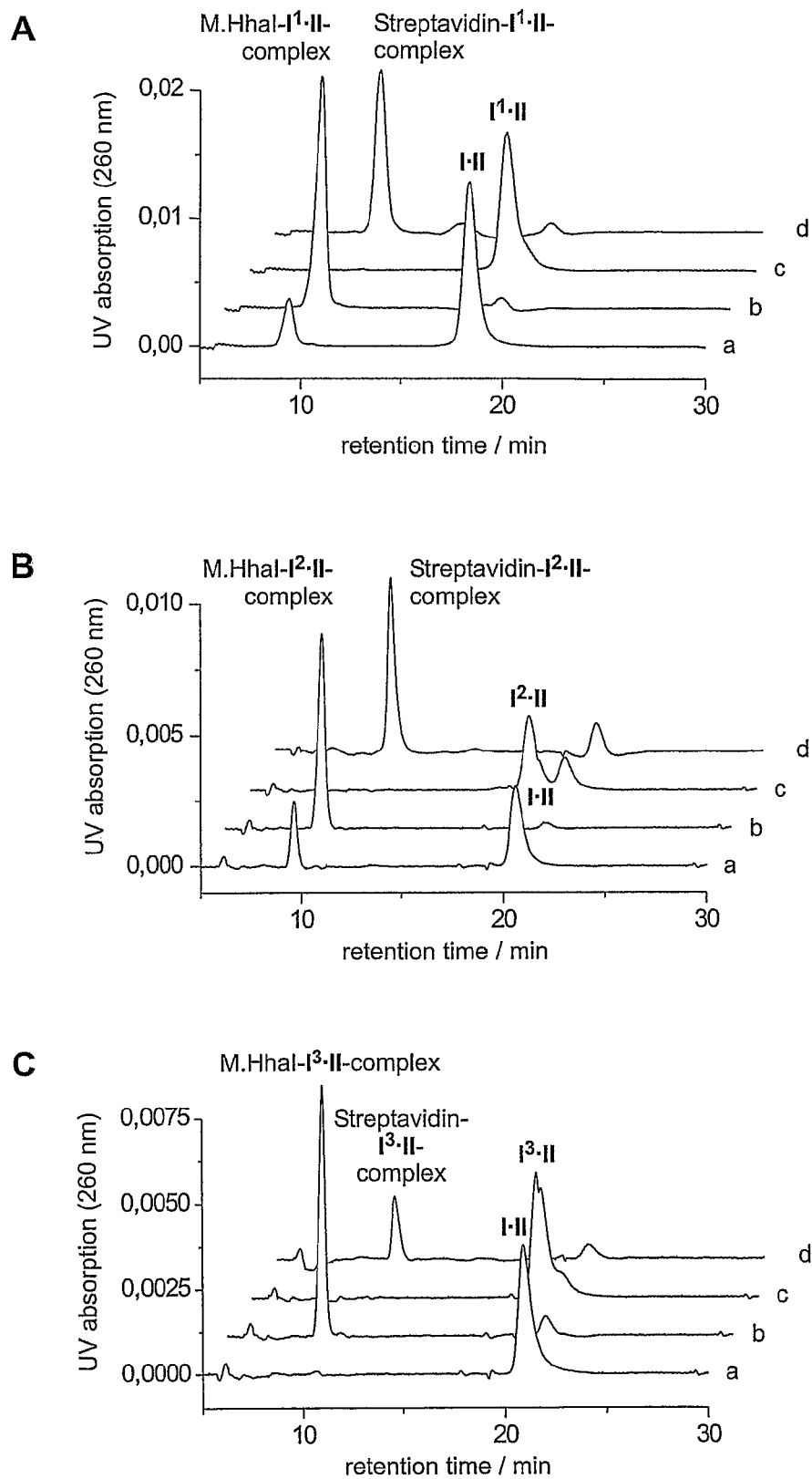
FIG. 1: M.HhaI-catalysed coupling of biotinylated aziridine cofactor 1 (A), 2 (B) and 3 (C) with the duplex oligodeoxynucleotide I-II analyzed by anion exchange HPLC at the beginning of the reaction (a), after 3 h in A, 1.5 h in B, 6.25 h in C (b), after additional heating to 65° C. for 30 min (c) and further addition of streptavidin (d).

Normally, the biomolecule is contacted by the methyltransferase in the presence of a cofactor of the methyltransferase. Preferably, said cofactor is the N-adenosyl aziridine derivative of formula (I).

The term "methyltransferase" refers to enzymes normally transferring the activated methyl from S-adenosyl-L-methionine (AdoMet) onto their substrate. Preferably, the methyltransferase is an enzyme capable of methylating DNA, RNA or (poly)peptides. More preferably, the methyltransferase is a DNA methyltransferase selected from M.HhaI, M.TaqI, M.BseCI and M.SssI.

The term "detecting whether the recognition sequence of said methyltransferase has been modified with the cofactor or a derivative thereof" means assessing whether the cofactor of formula (I) or a derivative thereof is attached to the biomolecule. Preferably, detection methods involve identifying the particular residue, within the recognition sequence of the methyltransferase, modified by the cofactor or the derivative thereof. Said derivative may be any compound resulting from the reaction between the N-adenosylaziridine derivative of formula (I) and the biomolecule.

The term "recognition sequence" refers to the particular sequence within the biomolecule recognized by the methyltransferase. In case the methyltransferase is a DNA methyltransferase, the recognition sequence may comprise 2, 3, 4, 5, 6, or 8 nucleotides or nucleotide pairs. As used herein, the recognition sequence also comprises the acceptor site for the N-adenosylaziridine derivative of formula (I) or the derivative thereof. The teaching of the present invention allows sequence-specific labelling in a methylation-dependent manner. DNA labelling of cytosine residues located in so-called CpG islands is a particular aspect of the present invention, as this allows to assess the methylation status of human chromosomal DNA. Therefore, the methods of the present invention are particularly useful for, but not limited to, diagnosing diseases associated with an altered methylation status of the chromosomal DNA. It should also be useful to access the methylation status of DNA from other sources as well as the methylation status of RNA or (poly)peptides. In addition, the cofactor of formula (I) or a derivative thereof in complex with a methyltransferase could be used to sequence-specifically label DNA, RNA or (poly)peptides which should be useful for various applications in biochemistry, molecular biology, gene therapy and nanobiotechnology. Furthermore, the cofactor of formula (I) or a derivative thereof could be used to find new methylation targets for methyltransferases.

The experimental results disclosed herein prove that the N-adenosylaziridine derivative of the present invention can replace the natural cofactor of M.HhaI. It was found that the N-adenosylaziridine derivative of the present invention can also be used by other S-adenosyl-L-methionine-dependent DNA methyltransferases, like M.TaqI, M.BseCI and M.SssI. Preferably, said S-adenosyl-L-methionine-dependent methyltransferase is selected from the group of DNA methyltransferases M.HhaI, M.TaqI, M.BseCI, M.SssI, M.RsrI, M.DpnM, M.PvuII and M.MboII, from the group of RNA methyltransferases VP39, Fts/RrmJ, NS5 and ErmC' or from the group of (poly)peptide methyltransferases hPIMT, LSMT, SET7/9, HemK/PrmC, hDOT1L or PRMT1.

In a preferred embodiment of the present invention, said biomolecule is a nucleic acid molecule or a (poly)peptide. Nucleic acid molecules shall be understood to encompass DNA and RNA. Preferably, DNA is chromosomal or genomic DNA. The biomolecule may be of any length. The term "chromosomal DNA" also encompasses fragments of a chromosome. Preferably, said fragment has a length of up to 500 nucleotides (nt), 1 kilobase (kb), 2 kb, 3 kb, 4 kb, 5 kb, 6 kb, 7 kb, 8 kb, 9 kb, 10 kb or even longer. However, also encompassed by the term chromosomal DNA are short fragments with a length of up to 5 nt, 10 nt, 15 nt, 20 nt, 25 nt, 30 nt, 35 nt, 40 nt, 45 nt, 50 nt, 100 nt, 200 nt, 300 nt, 400 nt, 500 nt.

In yet another preferred embodiment of the present invention, said step (a) is performed in vitro, with cell extracts or in vivo. Generally, suitable reaction conditions for treatment with restriction enzymes and DNA methyltransferases are known to the skilled person and are documented, for example, in standard textbooks of molecular biology (see e.g. Sambrook et al., "Molecular Cloning, A Laboratory Manual"; ISBN: 0879695765, CSH Press, Cold Spring Harbor, 2001). Suitable conditions for cofactor labelling mediated by M.HhaI are, e.g. 80 µM N-adenosylaziridine derivative, 11.3 nM double-stranded plasmid DNA, 380 nM M.HhaI in buffer (10 mM Tris hydrochloride, pH 7.4, 50 mM sodium chloride, 0.05 mM ethylenediaminetetraacetic acid and 2 mM β-mercaptoethanol). Incubation may be performed for 2 hours at 37° C.

When the methods of the present invention are carried in vitro a biological sample is isolated from an individual prior to analysis. The term "biological sample" relates to the specimen taken from the individual. Preferably, said specimen is taken from hair, skin, mucosal surfaces, body fluids, including blood, plasma, serum, urine, saliva, sputum, tears, liquor cerebrospinalis, semen, synovial fluid, amniotic fluid, breast milk, lymph, pulmonary sputum, bronchial secretion or stool.

The individual may be a human or an animal. Preferably, the individual is avian including turkey or hen, or the individual is a mammal including human, primate, rat, mouse, guinea pig, pig, cattle, cat or rabbit.

In a more preferred embodiment of the present invention, said nucleic acid molecule is DNA. Preferably, said DNA is chromosomal DNA.

In another more preferred embodiment of the present invention, the method further comprises prior to step (a) a step of treating the DNA with a restriction enzyme. Restriction enzymes may be selected from the group consisting of AatII, AccI, Acc65I, AciI, AclI, AfeI, AflII AflIII, AgeI, AhdI, AluI, AlwI, AlwNI, ApaI, ApaLI, ApoI, AscI, AseI, AsiSI, AvaI, AvaII, AvrII, BaeI, BamHI, BanI, BanII, BbsI, BbvI, BbvCI, BceAI, BcgI, BciVI, BclI, BfaI, BfrBI, BfuAI, BglI, BglII, BlpI, Bme1580I, BmgBI, BmrI, BpmI, BsaI, BsaAI, BsaBI, BsaHI, BsaJI, BsaWI, BsaXI, BseRI, BsgI, BsiEI, BsiHKAI, BsiWI, BslI, BsmI, BsmAI, BsmBI, BsmFI, BsoBI, Bsp1286I, BspCNI, BspDI, BspEI, BspHI, BspMI, BsrI, BsrBI, BsrDI, BsrFI, BsrGI, BssHII, BssKI, BssSI, BstAPI, BstBI, BstEII, BstF5I, BstNI, BstUI, BstXI, BstYI, BstZ17I, Bsu36I, BtgI, BtrI, BtsI, Cac8I, ClaI, DdeI, DpnI, DpnII, DraI, DraII, DrdI, EaeI, EagI, EarI, EciI, EcoNI, EcoO109I, EcoRI, EcoRV, FauI, Fnu4HI, FokI, FseI, FspI, HaeII, HaeIII, HgaI, HhaI, HinP1I, HincII, HindIII, HinfI, HpaI, HpaII, HphI, Hpy99I, Hpy188I, Hpy188III, HpyCH4III, HpyCH4IV, HpyCH4V, KasI, KpnI, MboI, MboII, MfeI, MluI, MlyI, MnlI, MscI, MseI, MslI, MspI, MspAII, MwoI, NaeI, NarI, NciI, NcoI, NdeI, NgoMIV, NheI, NlaIII, NlaIV, NotI, NruI, NsiI, NspI, PacI, PaeR7I, PciI, PflFI, PflMI, PleI, PmeI, PmlI, PpuMI, PshAI, PsiI, PspGI, PspOMI, PstI, PvuI, PvuII, RsaI, RsrII, SacI, SacI, SalI, SapI, Sau96I, Sau3AI, SbfI, ScaI, ScrFI, SexAI, SfaNI, SfcI, SfiI, SfoI, SgrAI, SmaI, SmlI, SnaBI, SpeI, SphI, SspI, StuI, StyI, SwaI, TaqI, TfiI, TliI, TseI, Tsp45I, Tsp509I, TspRI, Tth111I, XbaI, XcmI, XhoI, XmaI and XmnI.

In yet another more preferred embodiment of the present invention, said DNA molecule is immobilized on a solid support. Solid supports that may be employed in accordance with the invention include filter material, chips, wafers, microliter plates. Immobilization on the solid support may be achieved by different means including covalent coupling to an activated surface or by hybridization to nucleic acid molecules.

In another more preferred embodiment of the present invention said DNA molecule is coupled to the solid support by hybridizing the DNA molecule to an oligonucleotide which is attached to said solid support. Hybridization conditions may be of low, intermediate or high stringency. The term "stringent conditions", as used herein, is well known to the skilled artesian and corresponds to conditions of high stringency. Appropriate stringent hybridization conditions for each sequence may be established by a person skilled in the art by modifying parameters such as temperature, composition of the nucleic acid molecules, salt conditions etc.; see, for example, Sambrook et al., "Molecular Cloning, A Laboratory Manual"; CSH Press, Cold Spring Harbor, 1989 or Higgins and Hames (eds.), "Nucleic acid hybridization, a practical approach", IRL Press, Oxford 1985, see in particular the chapter "Hybridization Strategy" by Britten & Davidson, 3 to 15. Stringent hybridization conditions are, for example, conditions comprising overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/mL denatured, sheared salmon sperm DNA, followed by washing the filters in 0.1×SSC at about 65° C. Other stringent hybridization conditions are for example 0.2×SSC (0.03 M NaCl, 0.003 M sodium citrate, pH 7) at 65° C. In addition, to achieve even lower stringency, washes performed following stringent hybridization can be done at higher salt concentrations (e.g. 5×SSC). Note that variations in the above conditions may be accomplished through the inclusion and/or substitution of alternate blocking reagents used to suppress background in hybridization experiments. Typical blocking reagents include, but are not limited to, Denhardt's reagent, BLOTTO, heparin, denatured salmon sperm DNA, and commercially available proprietary formulations. The inclusion of specific blocking reagents may require modification of the hybridization conditions described above, due to problems with compatibility. Also contemplated are hybridization conditions of lower stringency. Changes in the stringency of hybridization and signal detection are, for example, accomplished through the manipulation of formamide concentration (lower percentages of formamide result in lowered stringency), salt conditions, or temperature. For example, lower stringency conditions include an overnight incubation at 37° C. in a solution comprising 6×SSPE (20×SSPE=3 M NaCl; 0.2 M $NaH_2PO_4$; 0.02 M EDTA, pH 7.4), 0.5% SDS, 30% formamide, 100 µg/mL salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

In another more preferred embodiment of the present invention, the methyltransferase is an orphan DNA methyltransferase or part of a bacterial restriction modification system.

In yet another more preferred embodiment of the present invention, said methyltransferase from a bacterial restriction modification system is selected from M.HhaI, M.TaqI, M.BseCI and M. SssI. The term "M.HhaI" refers to the DNA methyltransferase deposited in the Swissprot database under accession number P05102. The term "M.TaqI" refers to the DNA methyltransferase deposited in the Swissprot database under accession number P14385. The term "M.BseCI" refers to the DNA methyltransferase deposited in the Swissprot database under accession number P43423. However, any other methyltransferase with the same sequence specificity, i.e. with the same recognition sequence, or a reduced sequence specificity comprising only part of the recognition sequence of M.HhaI, M.TaqI or M.BseCI could be useful for the methods of the present invention.

In another more preferred embodiment of the present invention, (a) the N-adenosyl-aziridine derivative blocks restriction enzyme cleavage at the recognition sequence of the DNA methyltransferase; and (b) methylation is detected by testing whether the modification of the DNA by the N-adenosylaziridine derivative blocks cleavage mediated by a restriction enzyme at said recognition sequence. Any restriction enzyme and DNA methyltransferase mentioned in the present invention may be used when performing this method.

It has been observed by the inventor of the present invention that the presence of the N-adenosylaziridine derivative at the acceptor site of the recognition sequence blocks DNA cleavage by restriction enzymes with an overlapping or the same recognition sequence. Blocking restriction enzyme cleavage, as used herein, means preventing the restriction enzyme from cutting the DNA strands. Without being bound to theory, it is assumed that steric hindrance blocks accessibility of the recognition sequence so that the restriction enzyme can no longer bind to its target sequence in a productive manner. This observation can be exploited by assays which involve an initial labelling step with the N-adenosylaziridine derivative of the present invention and a subsequent cleavage step with a restriction enzyme. Naturally, the choice of the restriction enzyme depends on the particular DNA methyltransferase employed in the labelling step. As a general guideline, the recognition sequence of the restriction enzyme should be nearby the modified base. Preferably, the recognition sequence of the restriction enzyme comprises the modified base. More preferably, the recognition sequence of the DNA methyltransferase and the recognition sequence of the restriction enzyme are the same. The choice of particular combinations of restriction enzyme and DNA methyltransferase is obvious to the skilled person and needs no further explanation. Moreover, the labelling reaction performed by the DNA methyltransferase and the restriction enzyme cleavage may be performed under standard conditions.

In yet another more preferred embodiment of the present invention, (a) the N-adenosylaziridine derivative interferes with nucleic acid amplification at the recognition site of the methyltransferase; and (b) methylation is detected by testing whether amplification of the nucleic acid molecule at the recognition site of the methyltransferase has been retarded.

Retardation of amplification may be achieved by interfering with primer binding or with strand elongation during an amplification reaction.

The term "amplification" or "amplify" means increase in copy number. The person skilled in the art know various methods to amplify nucleic acid molecules, these methods may also be used in the present invention's method of diagnosing. Amplification methods include, but are not limited to, "polymerase chain reaction" (PCR), "ligase chain reaction" (LCR, EPA320308), "cyclic probe reaction" (CPR), "strand displacement amplification" (SDA, Walker et al., (1992) Nucleic Acid Res. 7, 1691-1696), "transcription based amplification systems" (TAS, Kwoh et al., (1989) Proc. Nat. Acad. Sci. USA 86, 1173; Gingeras et al., PCT Application WO 88/10315). Preferably, amplification of DNA is accomplished by using polymerase chain reaction (PCR) [Methods in Molecular Biology, Vol. 226 (Bartlett and Stirling, eds.): PCR protocols, 2nd edition; PCR Technology: Principles and Applications for DNA Amplification (Erlich, ed.), New York 1992; PCR Protocols: A guide to methods and applications (Innis et al., eds.), Academic Press, San Diego 1990]. Nucleic acid amplification methods may be particularly useful in cases when the sample contains only minute amounts of nucleic acid. If said nucleic acid is RNA, an RT-PCR might be performed. Subsequently, another amplification step involving PCR may be performed. Alternatively, if said nucleic acid contained in the sample is DNA. PCR may be performed.

The PCR, generally, consists of many repetitions of a cycle which consists of: (a) a denaturing step, which melts both strands of a DNA molecule; (b) an annealing step, which is aimed at allowing the primers to anneal specifically to the melted strands of the DNA molecule; and (c) an extension step, which elongates the annealed primers by using the information provided by the template strand. Generally, PCR can be performed for example in a 50 µL reaction mixture containing 5 µL of 10×PCR buffer with 1.5 mM $MgCl_2$, 200 µM of each deoxynucleoside triphosphate, 0.5 µL of each primer (10 µM), about 10 to 100 ng of template DNA and 1 to 2.5 units of Taq DNA Polymerase. The primers for the amplification may be labelled or be unlabelled. DNA amplification can be performed, e.g. with a model 2400 thermal cycler (Applied Biosystems, Foster City, Calif.): 2 min at 94° C., followed by 35 cycles consisting of annealing (30 s at 50° C.), extension (1 min at 72° C.), denaturing (10 s at 94° C.) and a final annealing step at 55° C. for 1 min as well as a final extension step at 72° C. for 5 min. However, the person skilled in the art knows how to optimize these conditions for the amplification of specific nucleic acid molecules or to scale down or increase the volume of the reaction mix.

A further method of nucleic acid amplification is the "reverse transcriptase polymerase chain reaction" (RT-PCR). This method is used when the nucleic acid to be amplified consists of RNA. The term "reverse transcriptase" refers to an enzyme that catalyzes the polymerization of deoxyribonucleoside triphosphates to form primer extension products that are complementary to a ribonucleic acid template. The enzyme initiates synthesis at the 3' end of the primer and proceeds toward the 5' end of the template until synthesis terminates. Examples of suitable polymerizing agents that convert the RNA target sequence into a complementary, copy-DNA (cDNA) sequence are avian myeloblastosis virus reverse transcriptase and *Thermus thermophilus* DNA polymerase, a thermostable DNA polymerase with reverse transcriptase activity marketed by Perkin Elmer. Typically, the genomic RNA/cDNA duplex template is heat denatured during the first denaturation step after the initial reverse transcription step leaving the DNA strand available as an amplification template. Suitable polymerases for use with a DNA template include, for example, *E. coli* DNA polymerase I or its Klenow fragment, T.sub.4 DNA polymerase, Tth polymerase, and Taq polymerase, a heat-stable DNA polymerase isolated from *Thermus aquaticus* and developed and manufactured by Hoffmann-La Roche and commercially available from Perkin Elmer. The latter enzyme is widely used in the amplification and sequencing of nucleic acids. The reaction conditions for using Taq DNA polymerase are known in the art and are described, e.g. in: PCR Technology, Erlich (1989, Stockton Press, New York; or in: Innis, Gelfand, Sninsky and White. 1990, PCR Protocols: A guide to methods and applications. Academic Press, New York. High-temperature RT provides greater primer specificity and improved efficiency. Copending U.S. patent application Ser. No. 07/746,121, filed Aug. 15, 1991, describes a "homogeneous RT-PCR" in which the same primers and polymerase suffice for both the reverse transcription and the PCR amplification steps, and the reaction conditions are optimized so that both reactions occur without a change of reagents. *Thermus thermophilus* DNA polymerase, a thermostable DNA polymerase that can function as a reverse transcriptase, can be used for all primer extension steps, regardless of template. Both processes can be done without having to open the tube to change or add reagents; only the temperature profile is adjusted between the first cycle (RNA template) and the rest of the amplification cycles (DNA template). The RT reaction can be performed, for example, in a 20 μL reaction mix containing: 4 μL of 5×ANV-RT buffer, 2 μL of oligo dT (100 μg/mL), 2 μL of 10 mM dNTPs, 1 μL total RNA, 10 units of AMV reverse transcriptase, and H2O to 20 μL final volume. The reaction may be, for example, performed by using the following conditions: The reaction is held at 70° C. for 15 minutes to allow for reverse transcription. The reaction temperature is then raised to 95° C. for 1 minute to denature the RNA-cDNA duplex. Next, the reaction temperature undergoes two cycles of 95° C. for 15 seconds and 60° C. for 20 seconds followed by 38 cycles of 90° C. for 15 seconds and 60° C. for 20 seconds. Finally, the reaction temperature is held at 60° C. for 4 minutes for the final extension step, cooled to 15° C., and held at that temperature until further processing of the amplified sample.

The term "primer" or "oligonucleotide", as used throughout the invention, refers to a short nucleic acid molecule from about 8 to about 30, eventually to about 50 nucleotides in length, whether natural or synthetic, capable of acting as a point of initiation of nucleic acid synthesis under conditions in which synthesis of a primer extension product complementary to a template nucleic acid strand is induced, i.e., in the presence of four different nucleoside triphosphates or analogues thereof and an agent for polymerisation (i.e., DNA polymerase or reverse transcriptase) in an appropriate buffer and at a suitable temperature. Preferably, a primer is a single-stranded oligodeoxyribonucleotide. The appropriate length of a primer depends on the intended use of the primer but typically ranges for PCR primers and primers used in sequencing reactions from 10 to 25 nucleotides. Short primer molecules generally require cooler temperatures to form sufficiently stable hybrid complexes with the template. A primer need not reflect the exact sequence of the template but must be sufficiently complementary to hybridize specifically with a template, provided its ability to mediate amplification is not compromised. "Hybridize" refers to the binding of two single-stranded nucleic acids via complementary base pairing, i.e. A to T (in RNA: U), G to C. The term "primer pair" refers to two primers that hybridize with the plus and minus strand, respectively, of a double-stranded nucleic acid molecule, and allow the amplification of e.g. DNA fragments, as for example in a PCR reaction. A primer can be labelled, if desired, by incorporating a compound detectable by spectroscopic, photochemical, biochemical, immunochemical, or chemical means. For example, useful labels include, but are not limited to, fluorescent dyes, electron-dense reagents, biotin, or small peptides for which antisera or monoclonal antibodies are available. A label can also be used to "capture" the primer, so as to facilitate a selection of amplified nucleic acid or fragments thereof. Carboxyfluorescein (FAM) and 6-carboxy-X-rhodamine (ROX) are preferred labels. However, other preferred labels include fluorochromes, e.g. fluorescein isothiocyanate (FITC), Texas Red, phycoerythrin, allophycocyanin, 6-carboxyfluorescein (6-FAM), 2',7'-dimethoxy-4',5'-dichloro-6-carboxyfluorescein (JOE), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc.

The label may also be a two stage system, where the primer is conjugated to biotin, haptens, etc. having a high affinity binding partner, e.g. avidin, specific antibodies, etc., where the binding partner is conjugated to a detectable label. The label may be conjugated to one or both of the primers.

During said method for diagnosing, a step of nucleic acid sequencing may be performed. Any methods known in the art may be used for sequencing. Preferably, the nucleic acid sequence is determined by a method based on the sequencing techniques of Sanger or Maxam/Gilbert (see for example: Methods in Molecular Biology, Vol. 167 (Graham and Hill, eds.): DNA sequencing protocols. 2nd edition, 2001; Galas and McCormack, Genomic Technologies: Present and Future. Caister Academic Press, Wymondham, UK, 2002).

In a preferred embodiment of the present invention, PCR is real-time PCR. In another preferred embodiment of the present invention, nucleic acid amplification is carried out by real-time PCR.

In yet another more preferred embodiment of the present invention, (a) the N-adenosylaziridine derivative contains a fluorescent label; and (b) methylation is detected by measuring the presence or amount of fluorescence in said nucleic acid molecule. Said N-adenosylaziridine derivative may be labelled with any of the fluorescent labels mentioned in the present invention or known to the skilled artisan. In accordance with the present invention, Alexa, BODIPY, fluorescein, rhodamine, Texas red, a cyanine fluorophore or a derivative thereof are particularly preferred labels.

"Measuring the presence or amount of fluorescence" means assessing whether or not or how much fluorescence can be detected by fluorescence spectroscopy.

In another more preferred embodiment of the present invention, (a) nucleic acid molecules modified at the methyltransferase recognition sequence are purified by affinity purification; and (b) the N-adenosylaziridine derivative contains an affinity tag.

Nucleic acid molecules may be purified by using a compound capable of specifically binding to the label of the N-adenosylaziridine derivative of the present invention. In that case the label corresponds to or comprises an affinity tag. An affinity tag may be combined with one or more fluorescent labels. Preferably, the compound capable of binding to the label or affinity tag is an antibody, a protein, a peptide or an aptamer, wherein binding of these compounds is specific. The affinity tag may be an epitope such as the flag-tag, c-myc-tag, HA-tag, digoxygenin or dinitrophenol. Alternatively, the affinity tag may be an artificial peptide such as the His tag. "His tags" may be selected from $His_4$, $His_5$, $His_6$, $His_7$, $His_8$, $His_9$, $His_{10}$, $His_{11}$, $His_{12}$, $His_{13}$, $His_{14}$, $His_{15}$. Moreover, the affinity tag may be biotin, strep-tag, glutathione, nickel-nitrilotriacetic acid (NTA) or maltose. If the affinity tag is a "His tag", nickel coupled to a solid support may be used for purification. If the affinity tag is an epitope, an antibody-affinity coupled to a solid support may be used for purification. If the affinity tag is biotin or strep-tag, avidin or streptavidin or the like bound to a solid support may be used for purification. If the affinity tag is glutathione, glutathione transferase (GST) bound to a solid support may be used for purification. If the affinity tag is maltose, maltose binding protein bound to a solid support may be used for purification. If the affinity tag is nickel-nitrilotriacetic acid (NTA), a peptide containing several histidine residues bound to a solid support may be used for purification.

Affinity purification generally involves the separation of molecules in solution (mobile phase) based on differences in binding interaction with a ligand that is immobilized to a stationary material (solid phase). A support or matrix in affinity purification is any material to which a ligand may be covalently attached. Typically, the material to be used as an affinity matrix is insoluble in the system in which the target molecule is found. Usually, but not always, the insoluble matrix is solid. Hundreds of substances have been described and employed as affinity matrices. Useful affinity supports are those with a high surface area to volume ratio, chemical groups that are easily modified for covalent attachment of ligands, minimal nonspecific binding properties, good flow characteristics and mechanical and chemical stability. Preferred solid supports are agarose, sepharose and polystyrene beads.

Preferably, affinity purification is performed by using biotin, digoxygenin, glutathione or nickel-nitrilotriacetic acid (NTA) as the affinity tag of the N-adenosylaziridine derivative of the present invention.

In another more preferred embodiment of the present invention, the N-adenosyl-aziridine derivative is added to a cytosine residue and cannot be added to a 5-methylcytosine residue in DNA.

In a preferred embodiment of the present invention, the method comprises after step (a) the additional step of sequencing the DNA molecule. Any methods known in the art may be used for sequencing. Preferably, the nucleic acid sequence is determined by a method based on the sequencing techniques of Sanger or Maxam/Gilbert (see for example: Methods in Molecular Biology, Vol. 167 (Graham and Hill, eds.): DNA sequencing protocols. $2^{nd}$ edition, 2001; Galas and McCormack, Genomic Technologies: Present and Future. Caister Academic Press, Wymondham, UK, 2002).

In another preferred embodiment of the present invention, said detectable cofactor is detected by (a) an antibody specifically binding to said detectable cofactor or by (b) avidin or streptavidin specifically binding to said detectable cofactor.

The term "antibody", as used throughout the invention, refers to monoclonal antibodies, polyclonal antibodies, chimeric antibodies, single chain antibodies, or a fragment thereof. Preferably the antibody is specific for its epitope. The antibodies may be humanized antibodies, synthetic antibodies, antibody fragments, such as Fab, F(ab2)', Fv or scFv fragments etc., or a chemically modified derivative of any of these. Monoclonal antibodies can be prepared, for example, by the techniques as originally described in Köhler and Milstein, (1975) Nature 256, 495, and Galfré, (1981) Meth. Enzymol. 73, 3, which comprise the fusion of mouse myeloma cells to spleen cells derived from immunized mammals with modifications developed by the art. Furthermore, antibodies or fragments thereof can be obtained by using methods which are described, e.g. in Harlow and Lane "Antibodies, A Laboratory Manual", CSH Press, Cold Spring Harbor, 1998. When derivatives of said antibodies are obtained by the phage display technique, surface plasmon resonance as employed in the BIAcore system can be used to increase the efficiency of phage antibodies which bind to an epitope to be analyzed (Schier, (1996) Human Antibodies Hybridomas 7, 97-105; Malmborg, (1995) J. Immunol. Methods 183, 7-13). The production of chimeric antibodies is described, for example, in WO89/09622.

Antibodies may be labelled, wherein the label may be any of the labels mentioned in the present invention.

Finally, in another preferred embodiment of the present invention, the identity of said DNA molecule is determined by DNA sequencing, hybridization, Maldi-T of or analysis of nucleoside composition by enzymatic fragmentation and chromatography.

The present invention also relates to the use of the methods of the present invention for the diagnosis or prognosis of a disease state associated with increased or decreased DNA methylation, wherein said disease state is cancer or ICF syndrome. Preferably, the diagnosis is performed on a sample obtainable from a patient.

The term "increased or decreased methylation" refers to alterations of the methylation status of chromosomal DNA when the DNA of a healthy individual is compared with the DNA of an individual affected from the disease. According to the teaching of the present invention, alterations in the methylation status of chromosomal DNA can reflect an alteration of gene expression. In fact, in many cases the changes in the methylation status of the DNA contribute to an increased or decreased transcription. Altered methylation patterns can be tightly coupled to particular disease states so that the diagnosis of an altered methylation pattern within chromosomal DNA may be used as a diagnostic or prognostic marker for the disease.

Cancers which may be diagnosed with the teaching of the present invention include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias.

The term "ICF syndrome", refers to a disease characterized by immunodeficiency, centromeric region instability and facial anomalies. ICF syndrome is a unique DNA methylation deficiency disease diagnosed by chromosomal anomalies, especially in the vicinity of the centromeres of chromosomes 1, 9 and 16 (Chr 1 and Chr 16) in mitogen-stimulated lymphocytes. These aberrations include decondensation of centromere-adjacent heterochromatin, multiradial chromosomes with up to 12 arms, and whole-arm deletions. At the molecular level, one of the most consistent features of ICF syndrome is the hypomethylation of juxtacentromeric repeat sequences on chromosomes 1, 9 and 16 (Jeanpierre et al., (1993) Hum. Mol. Genet. 2, 731-735). Hence the hypomethylated DNA regions may be analyzed and a diagnostic method be based thereon.

The cofactor of the present invention, is the N-adenosylaziridine derivative represented by formula (I),

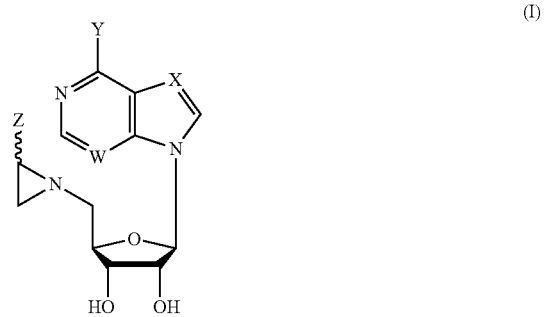

(I)

wherein
W is selected from N and CH,
X is N or $CR^1$,
Y is $NH_2$ or $NHR^2$,
Z is H, $R^3$ or $CH_2CH(COOH)(NH_2)$, with the proviso that
if X is $CR^1$, Y is $NH_2$ and Z is H or $CH_2CH(COOH)(NH_2)$,
if X is N and Y is $NHR^2$, Z is H or $CH_2CH(COOH)(NH_2)$,
if X is N and Y is $NH_2$, Z is $R^3$,
$R^1$ is selected from $—(CH_2)_nR^4$, $—(CH=CH)_m(CH_2)_nR^4$, $—(CH_2)_o(CH=CH)_m(CH_2)_nR^4$, $—(C≡C)_m(CH_2)_nR^4$, $—(C≡C)_m(C_6H_4)_o(CH_2)_nR^4$, $—(C_6H_4)_m(CH_2)_nR^4$, $—CO(CH_2)_nR^4$ and $—S(CH_2)_nR^4$;
$R^2$ is selected from $—(CH_2)_nR^4$, $—(C_6H_4)_m(CH_2)_nR^4$, $—CO(C_6H_4)_m(CH_2)_nR^4$ and $—CO(CH_2)_nR^4$;
$R^3$ is selected from $—(CH_2)_nR^4$, $—(CH=CH)_m(CH_2)_nR^4$, $—(C≡C)_m(CH_2)_nR^4$, $—(C_6H_4)_m(CH_2)_nR^4$ and $—CONH(CH_2)_nR^4$;
$R^4$ is selected from $—NHR^5$, $—NHCO(CH_2)_pSR^5$, $—SR^5$, $—OR^5$, $—O(C_2H_5O)_n(C_2H_5)NHR^5$, $—CH_2NHNHR^5$, $—NHCOCH(CH_2SH)NHR^5$ and $—CONHR^5$;
$R^5$ is selected from fluorophores, affinity tags, crosslinking agents, chromophors, proteins, peptides, amino acids which may optionally be modified, nucleotides, nucleosides, nucleic acids, carbohydrates, lipids, PEG, transfection reagents, beads, intercalating agents, nucleic acid cleaving reagents and nanoparticles (e.g. gold cluster)
n, m, o and p are independently selected from 0 or an integer from 1 to 5000.

Preferably $R^1$ is selected from $—(CH_2)_nR^4$, $—(CH=CH)_m(CH_2)_nR^4$, $—(C≡C)_m(CH_2)_nR^4$, $—(C≡C)_m(C_6H_4)_o(CH_2)_nR^4$ and $—(C_6H_4)_m(CH_2)_nR^4$, more preferably $R^1$—$(CH_2)_nR^4$ or $—(C≡C)_m(CH_2)_nR^4$.

$R^2$ is preferably selected from $—(CH_2)_nR^4$ and $—(C_6H_4)_m(CH_2)_nR^4$, more preferably $—(CH_2)_nR^4$.

$R^3$ is preferably selected from $—(CH_2)_nR^4$ and $—CONH(CH_2)_nR^4$, more preferably $—(CH_2)_nR^4$.

Preferably $R^4$ is selected from $—NHR^5$, $—NHCO(CH_2)_pSR^5$, and $—O(C_2H_5O)_n(C_2H_5)NHR^5$, more preferably $R^4$ is $—NHR^5$.

$R^5$ is preferably selected from fluorophores, affinity tags, crosslinking agents, peptides, nucleic acids, carbohydrates, lipids, transfection reagents, intercalating agents, nucleic acid cleaving reagents and nanoparticles (e.g gold cluster), more preferably affinity tags.

n is preferably from 0 or an integer from 1 to 100, more preferably 1, 3 and 4. m is preferably an integer from 1 to 10, more preferably 1. o is preferably an integer from 1 to 10, more preferably 1. p is preferably an integer from 1 to 10, more preferably 3.

According to a preferred embodiment, the cofactor of formula (I) is selected from

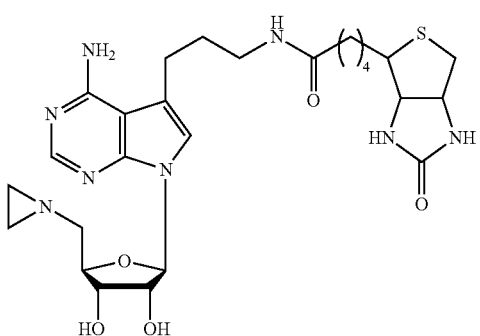

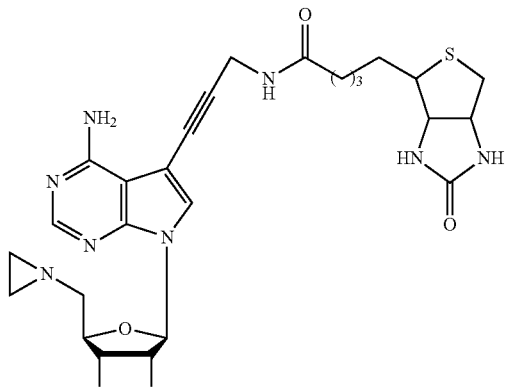

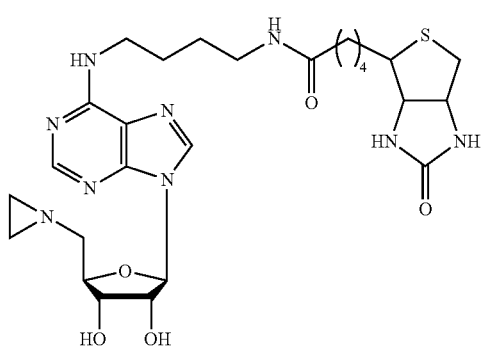

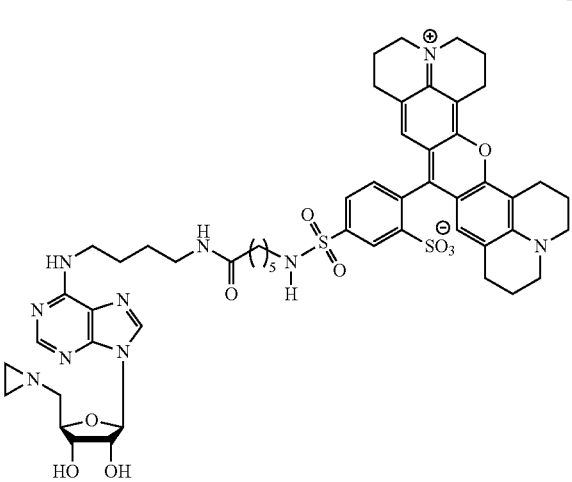

In a preferred embodiment of the present invention, said fluorophore is Alexa, BODIPY, coumarin, dansyl, fluorescein, mansyl, pyrene, rhodamine, Texas red, TNS, a cyanine fluorophore or a derivative thereof or any other label mentioned in the specification of the present invention.

In another preferred embodiment of the present invention, said affinity tag is a peptide tag, biotin, maltose, nickel-nitrilotriacetic acid (NTA), digoxygenin or dinitrophenol.

In a more preferred embodiment of the present invention, said peptide tag is his-tag or a tag with metal chelating properties, strep-tag, flag-tag, c-myc-tag, HA-tag, epitopes or glutathione. Binding partners attached to a solid support can be used for affinity purification of nucleic acid molecules or (poly)peptides labelled with the N-adenosylaziridine derivative of the present invention. Preferably, the peptide tag is his-tag or strep-tag.

The term "tag with metal chelating properties" relates to a tag which confers binding of the N-adenosylaziridine derivative after covalent attachment to the biomolecule to a matrix used in Immobilized Metal Ion Affinity Chromatography (IMAC). The IMAC technique developed by Porath et al. (Porath et al., (1975) Nature 258, 598-599) is based on the interaction between certain protein superficial residues (histidines, cysteines, and in a lower degree tryptophans) and cations from transition metals which form chelates with polycarboxylic ligands. Typical conditions are described in the art and are known to the skilled person (Porath, (1992) Protein Expression and Purification 3, 263-281; Hemdan, and Porath, (1985) Journal of Chromatography 323, 255-264; Porath and Hansen, (1991) Journal of Chromatography 550, 751-764).

The term "strep-tag" relates to an 8 amino acid streptavidin binding sequence. This sequence was found through the systematic screening of random peptide libraries in order to identify a peptide binding sequence with optimal affinity tag properties (Schmidt and Skerra, (1993) Prot. Engineering 6, 109-122). When attached to the N-adenosylaziridine derivative of the present invention, modified nucleic acid molecules or (poly)peptides can be affinity purified, e.g. by using a gravity-flow column with a matrix containing StrepTactin, Streptavidin, Avidin or the like. Such matrices are commercially available from, e.g. Sigma-Genosys/The Woodlands (Tex., USA) or IBA/Goettingen (Germany).

The term "flag-tag" relates to an 8 amino acid peptide which binds to an anti-flag antibody. When attached to the N-adenosylaziridine derivative of the present invention, modified nucleic acid molecules or (poly)peptides can be affinity purified, e.g. by using a gravity-flow column with a matrix containing an immobilized anti-flag antibody. Such matrix is commercially available from, e.g. Sigma-Aldrich.

The term "c-myc-tag" relates to a 10 amino acid peptide which binds to an anti-c-myc antibody. When attached to the N-adenosylaziridine derivative of the present invention, modified nucleic acid molecules or (poly)peptides can be affinity purified, e.g. by using a gravity-flow column with a matrix containing an immobilized anti-c-myc antibody. Such matrix is commercially available from, e.g. Pierce Biotechnology (IL, USA).

The term "HA-tag" relates to 9 amino acid peptide which is derived from the surface hemagglutinin of influenza virus and binds to an anti-HA antibody. When attached to the N-adenosylaziridine derivative of the present invention, modified nucleic acid molecules or (poly)peptides can be affinity purified, e.g. by using a gravity-flow column with a matrix containing immobilized anti-HA antibody.

The term "glutathione" relates to the tripeptide L-gamma-glutamyl-L-cysteinylglycine which binds to glutathione transferase (GST). When attached to the N-adenosyl-aziridine derivative of the present invention, modified nucleic acid molecules or (poly)peptides can be affinity purified, e.g. by using a gravity-flow column with a matrix containing immobilized glutathione transferase.

In another preferred embodiment of the present invention said crosslinking agent is maleimide, iodacetamide, or a derivative thereof or an aldehyde derivative, or a photocrosslinking agent. Preferably, the crosslinking agent is a photocrosslinking agent.

In a more preferred embodiment of the present invention, said photocrosslinking agent is arylazide, a diazo compound, psoralen or a benzophenone compound. Preferably, the photocrosslinking agent is psoralen.

In another preferred embodiment of the present invention, said nucleic acid cleaving reagent is iron-EDTA, acridine or a derivative thereof or a rhodium complex.

The present invention also relates to a complex of the cofactor of the present invention and a methyltransferase which normally uses S-adenosyl-L-methionine (AdoMet) as a cofactor.

In a preferred embodiment of the present invention, said methyltransferase normally transfers the methyl residue of S-adenosyl-L-methionine (AdoMet) onto a nucleic acid molecule or a (poly)peptide.

In a preferred embodiment of the present invention, said methyltransferase is an orphan DNA methyltransferase or part of a restriction modification system of a bacterium.

Said DNA methyltransferase may be selected from M.AacDam, M.AatII, M.AbaORFDP, M.AbaORFKP, M.AbrI, M.AccI, M.AccIII, M.AciI, M.AcII, M.AcuI, M.Afa22MI, M.AflIII, M.AflIIII, M.AgeI, M.AhdI, M.AhyBP, M.AlaK2I, M.AluI, M.AlwI, M.Alw26I, M.ApaI, M.ApaLI, M.ApeKI, M.ApoI, M.AquI, M.AscI, M.AseI, M.AseII, M.AsiSI, M.AspCNI, M.AtuCI, M.AtuCORF1997P, M.AtuDORF794P, M.AtuDORF3839P, M.AvaI, M.AvaII, M.AvaIII, M.AvaIVP, M.AvaV, M.AvaVI, M.AvaVII, M.AvaVIII, M.AvaIX, M.AvaORF3700P, M.AvaORF7270P, M.AvrI, M.AvrII, M.BabI, M.BaeI, M.BaII, M.BamHI, M.BamHIHI, M.BanI, M.BanII, M.BanIII, M.BatAORF3814P, M.BatA581ORF3846P, M.Bbu297I, M.BbvI, M1.BbvCI, M2.BbvCI, M.BbvSI, M1.BccI, M2.BccI, M.Bce1247I, M1.BceAI, M2.BceAI, M.Bce14579ORF939P, M.BceSORF365P, M.BceSORF4605P, M1.BceSORF5606P, M2.BceSORF5606P, M.Bcep1P, M.Bcep43ORFAP, M.BchI, M.BclI, M1.BcnI, M2.BcnI, M1.BcoKI, M2.BcoKI, M.Bcs139P, M.BdiI, M.BepI, M1.BfaI, M2.BfaI, M.BfaORFC157P, M1.BfuAI, M2.BfuAI, M.BgII, M.BgIII, M1.BhaI, M2.BhaI, M.BhaII, M.BjaORF2509P, M.BloNORF564P, M.BloNORF1473P, M.BlpI, M.BmaI, M.BmaPhiE125ORF56P, M.Bme216I, M.BmeLORF1444P, M.BmeTI, M1.BmrI, M2.BmrI, M.BnaI, M.BpmI, M1.Bpu10I, M2.Bpu10I, M1.BsaI, M2.BsaI, M.BsaAI, M.BsaJI, M.BsaWI, M1.BscGI, M2.BscGI, M.Bse634I, M.BseCI, M.BseDI, BseMII, BseRI, M.BseRI, M.BseYI, BsgI, M.BsgI, M.BsiWI, M.BsII, M1.BsmI, M2.BsmI, M.BsmAI, M.BsmBI, M.BsoBI, M.BspI, M.Bsp6I, M.Bsp50I, M.Bsp98I, M.Bsp106I, M.Bsp143II, BspCNI, M.BspCNI, M.BspEI, M.BspHI, M.BspIS4I, M.BspKT6I, BspLU11III, M1.BspLU11III, M2.BspLU11III, M1.BspMI, M2.BspMI, M.BspMII, M.BspRI, M.BspST5I, M1.BsrI, M2.BsrI, M1.BsrBI, M2.BsrBI, M.BsrFI, M.BssHI, M.BssHII, M.BssSI, M.BstI, M.BstEII, M.BstEIII, M1.BstF5I, M2.BstF5I, M3.BstF5I, M4.BstF5I, M.BstGII, M.BstLVI, M.BstNI, M.BstNBI, M.BstVI, M.BstXI, M.BstYI, M.Bsu15I, M.Bsu36I, M.Bsu6633I, M.BsuBI, M.BsuEII, M.BsuFI, M.Bsu1330ORF491P, M.BsuRI, M.BthIPS78, M.BthVORF4625P, M.BusLBORFC747P; M.BusLBORFC755P, M.Cac8I, M.Cac824I, M.Cac824ORF3358P, M.CauJORFC101P, M.CauJORFC102P, M.CauJORFC103P, M.CauJORFC104P, M.CauJORFC107P, M.CauJORFC110P, M.CauJORFC111P, M.CboI, M.CcrMI, M.Cdi630I, M.CdiCD6I, M.CdiCD6II, M.Cdi630ORFC898P, M.CefORF1493P, M.CeqI, M.CfrI, M.Cfr6I, M.Cfr9I, M.Cfr10I, M.Cfr13I, M.Cfr42I, M.CfrAI, M.CfrBI, M.CgII, M.CgIASI, M.CgILP6P, M.CjeNI, M.Cje81116ORFBP, M.Cje81116ORFCP, M.ClaI, M.Csp6I, M.Csp68KI, M.Csp68KIV, M.Csp68 KV, M.CteEORF387P, M.CthORFS26P, M.CthORFS34P, M.CthORFS93P, M.CviAI, M.CviAII, M.CviAIV, M.CviBI, M.CviBII, M.CviBIII, M.CviJI, M.CviORF5P, M.CviORF2111P, M.CviPI, M.CviQI, M.CviQII, M.Cvi- QIII, M.CviQIVP, M.CviQVP, M.CviQVI, M.CviQVII, M.CviQVIIIP, M.CviQIXP, M.CviQXP, M.CviQXI, M.CviRI, M.CviRII, M.CviSI, M.CviSII, M.CviSIII, M.CviSIVP, M.CviSVP, M.CviSVIP, M.CviTI, M.DdeI, DhaORFC135P, M1.DpnII, M2.DpnII, M.DraI, M.DraII, M.DraIII, M.DsaV, M.DvuORF19P, M.DvuORF2842P, M.EacI, M.EaeI, M.EagI, M1.EarI, M2.EarI, M.EcaI, M.Ecl18kI, M.Eco32I, M.Eco47II, M.Eco47III, M.Eco56I, Eco57I, M.Eco57I, M.Eco64I, M.Eco72I, M.Eco88I, M.Eco98I, M.Eco105I, M.Eco147I, M.Eco231I, M.Eco255I, M.Eco536P, M.Eco1639P, M.Eco1831P, M.Eco248534P, M.EcoAI, M.EcoBI, M.EcoCFTDamP, M.EcoCFTDam2P, M.EcoCFTDam3P, M.EcoCFTDcmP, M.EcoDI, M.EcoDR2, M.EcoDR3, M.EcoDXXI, M.Eco67Dam, M.EcoEI, M.EcoHI, M.EcoHK31I, M.EcoKI, M.EcoKII, M.EcoKDam, M.EcoKDcm, M.EcoKO157DamP, M.EcoKO157Dam2P, M.EcoKO157Dam3P, M.EcoKO157DcmP, M.EcoKO157ORF1953P, M.EcoLahn1P, M.EcoLahn3P, M.EcoNI, M.EcoNi12P, M.EcoO109I, M.EcoO157DamP, M.EcoO157DcmP, M.EcoO157ORF1454P, M.EcoO157ORF2389P, M.EcoO157ORF3349P, M.Eco536ORF3P, M.EcoPI, M.EcoP15I, M.EcoP1Dam, M.EcoPhi4795DamP, M.EcoRI, M.EcoRII, M.EcoRV, M.EcoR124I, M.EcoR124II, M.EcoRD2, M.EcoRD3, M.EcoStx1DamP, M.EcoStx2DamP, M.EcoT22I, M.EcoT38I, M.EcoT1Dam, M.EcoT2Dam, M.EcoT4Dam, M.EcoVIII, M.EcoVT2Dam, M.EcoWphiP, M.Eco29kI, M.EcopHSHP, M.EcopHSH2P, M.EcoprrI, M.EfaHGSORFHP, M.EphP1ORF1P, M.EsaBC1I, M.EsaBC3I, M.EsaBC4I, M.EsaBS1I, M.EsaBS9I, M.EsaDix1I, M.EsaDix2I, M.EsaDix3I, M.EsaDix4I, M.EsaDix5I, M.EsaDix6I, M.EsaDix7I, M.EsaLHCI, M.EsaLHCIII, M.EsaRM1P, M.EsaRM13P, M.EsaRM16P, M.EsaRM17P, M.EsaRM21P, M.EsaRM38P, M.EsaRM61P, M.EsaRM63P, M.EsaRM65P, M.EsaRM67P, M.EsaRM69P, M1.EsaS1I, M2.EsaS1I, M.EsaS3I, M.EsaS4I, M.EsaS6I, M.EsaS7I, M.EsaS8I, M.EsaSS2P, M.EsaSS5P, M.EsaSS12P, M.EsaSS13P, M.EsaSS15P, M.EsaSS16P, M.EsaSS18P, M.EsaSS19P, M.EsaSS22P, M.EsaSS30P, M.EsaSS31P, M.EsaSS35P, M.EsaSS36P, M.EsaSS40P, M.EsaSS43P, M.EsaSS47P, M.EsaSS48P, M.EsaSS49P, M.EsaSS52P, M.EsaSS55P, M.EsaSS57P, M.EsaSS67P, M.EsaSS69P, M.EsaSS70P, M.EsaSS71P, M.EsaSS72P, M.EsaSS73P, M.EsaSS74P, M.EsaSS75P, M.EsaSS76P, M.EsaSS79P, M.EsaSS81P, M.EsaSS83P, M.EsaSS87P, M.EsaSS88P, M.EsaSS90P, M.EsaSS96P, M.EsaSS97P, M.EsaSS103P, M.EsaSS104P, M.EsaSS105P, M.EsaSS106P, M.EsaSS107P, M.EsaSS108P, M.EsaSS109P, M.EsaSS110P, M.EsaSS111P, M.EsaSS113P, M.EsaSS117P, M.EsaSS120P, M.EsaSS123P, M.EsaSS126P, M.EsaSS130P, M.EsaSS131P, M.EsaSS134P, M.EsaSS136P, M.EsaSS137P, M.EsaSS144P, M.EsaSS145P, M.EsaSS150P, M.EsaSS153P, M.EsaSS154P, M.EsaSS155P, M.EsaSS156P, M.EsaSS160P, M.EsaSS163P, M.EsaSS165P, M.EsaSS167P, M.EsaSS169P, M.EsaSS170P, M.EsaSS172P, M.EsaSS174P, M.EsaSS177P, M.EsaSS181P, M.EsaSS182P, M.EsaSS186P, M.EsaSS187P, M.EsaSS192P, M.EsaSS195P, M.EsaSS200P, M.EsaSS214P, M.EsaSS215P, M.EsaSS216P, M.EsaSS218P, M.EsaSS221P, M.EsaSS222P, M.EsaSS223P, M.EsaSS225P, M.EsaSS228P, M.EsaSS237P, M.EsaSS238P, M.EsaSS241P, M.EsaSS244P, M.EsaSS245P, M.EsaSS246P, M.EsaSS247P, M.EsaSS254P, M.EsaSS259P, M.EsaSS264P, M.EsaSS266P, M.EsaSS268P, M.EsaSS269P, M.EsaSS270P, M.EsaSS275P, M.EsaSS278P, M.EsaSS281P, M.EsaSS282P, M.EsaSS283P, M.EsaSS289P, M.EsaSS297P, M.EsaSS302P, M.EsaSS303P, M.EsaSS305P, M.EsaSS315P, M.EsaSS317P, M.EsaSS318P, M.EsaSS319P, M.EsaSS323P, M.EsaSS326P, M.EsaSS328P, M.EsaSS329P, M.EsaSS334P, M.EsaSS335P, M.EsaSS336P, M.EsaSS51DamP, M.EsaSS65DamP, M.EsaSS138DamP, M.EsaSS198DamP, M.Esp3I, M.Esp1396I, M.EspRB49DamP, M.FauI, M.FnuDI, M.FnuDII, M.FnuDIII, M.Fnu4HI, M.FnuVDamP, M.FokI, M.FseI, M.FspI, M.FssI, M.GmeORFC6P, M.GmeORFC16P, M.GsuI, M.GviDamP, M.H2I, M.HaeII, M.HaeIII, M.HapII, M.HduDamP, M1.HgaI, M2.HgaI, M.HgiAI, M.HgiBI, M.HgiCI, M.HgiCII, M.HgiDI, M.HgiDII, M.HgiEI, M.HgiGI, M.HhaI, M.HhaII, M.HheORF238P, M.HheORF1050P, M.HheORF1244P, M.HheORF1445P, M.Hin1II, M.HinB231ORFDP, M.HinHP1Dam, M.HinHP2Dam, M.HinP1I, M.HincII, M.HindI, M.HindIII, M.HindIII, M.HindV, M.HindDam, M.HinfI, M.HinfIII, M.HjaI, M.HpaI, M.HpaII, M1.HphI, M2.HphI, M.HpyI, M.Hpy8I, M.Hpy87AP, M.Hpy99I, M.Hpy99II, M.Hpy99III, M.Hpy99IV, M1.Hpy99V, M2.Hpy99VP, M.Hpy99VI, M.Hpy99VIII, M.Hpy99IX, M.Hpy99X, M.Hpy99XI, M.Hpy166IV, M.Hpy178IP, M.Hpy188I, M.Hpy188II, M.Hpy188III, M.Hpy788606P, M.Hpy788845P, M.Hpy788849P, M.Hpy789115P, M.Hpy789117P, M.Hpy789137P, M.Hpy789145P, M.Hpy790101P, M.Hpy959772P, M.HpyAI, M1.HpyAII, M2.HpyAII, M.HpyAIII, M.HpyAIV, M.HpyAV, M1.HpyAVI, M2.HpyAVI, M.HpyAVII, M.HpyAVIII, M.HpyAIX, M.HpyAX, M.Hpy87AI, M.HpyAORF263P, M.HpyAORF369P, M.HpyAORF481P, M.HpyAORF483P, M1.HpyC1I, M2.HpyC1I, M.HpyCH4IV, M.HpyCH4V, M.HpyCR2ORF1P, M.HpyCR2ORF3P, M1.HpyCR4RM1P, M2.HpyCR4RM1P, M.HpyCR9RM1P, M.HpyCR9RM2P, M.HpyCR14RM1P, M.HpyCR14RM2P, M.HpyCR15RM2P, M.HpyCR16RM1P, M.HpyCR29RM1P, M.HpyCR29RM2P, M.HpyCR35RM1P, M.HpyCR35RM2P, M1.HpyCR38RM1P, M2.HpyCR38RM1P, M.HpyCR38RM2P, M.HpyF17I, M.Hpy99ORF430P, M.Hpy99ORF433P, M.Hpy99ORF846P, M.Hpy99ORF1012P, M.HspNORF1543P, M.KasI, M.KpnI, M.Kpn2I, M.KpnAI, M.KpnBI, M.Kpn19097Dam, M.Kpn19097Dam2P, M.Kpn19097ORFFP, M.Kpn2kI, M.Lci22RP, M.LinFORF11323P, M.LinFORF12222P, M.LinFORF12737P, M.LinLORF903P, M.LinLORF1547P, M.LinLORF2668P, M1.LlaAI, M2.LlaAI, M.LlaCI, M.LlaDI, M.LlaDII, M1.LlaDCI, M2.LlaDCHI, M.LlaKR2I, M.LmoAP, M.LmoEORF470P, M.LmoFORF327P, M.Lmo19115ORF1P, M.Lsp1109I, M.MamI, M1.MboI, M2.MboI, M1.MboII, M2.MboII, M.Mca43617ORFAP, M.Mca43617ORFBP, M1.Mca43617ORFDP, M2.Mca43617ORFDP, M.Mca43617ORFJP, M.MfeI, M.MjaI, M.MjaII, M.MjaIII, M.MjaIVP, M.MjaV, M.MjaVI, M.MloORFmlr7520P, M.MluI, M.MlyI, M.MmaMORFC174P, M.MmaSORF735P, M.MmeI, M.MmeII, M.MmoORF950P, M.MmoORF3450P, M.MmyIP, M.MmySCORF186P, M.MmySCORF216P, M.MmySCORF950P, M1.MnlI, M2.MnlI, M.MpeORF1230P, M1.MpeORF1780P, M2.MpeORF1780P, M.MpeORF4940P, M.MpeORF9800P, M.MpuCORF430P, M.MscI, M.MseI, M.MsmChe9cORF76P, M.MsmChe9cORF77P, M.MsmChe9cORF80P, M.MsmcdP, M.MsmomegaORF127P, M.MspI, M.MspAII, M.MspSD10I, M.MthFI, M.MthTI, M.MthZI, M.MunI, M.MvaI, M.Mva1269I, M.MwoI, M.NaeI, M.NarAORFC306P, M.NcoI, M.NdeI, M.NdeII, M.Ngo18785P, M.Ngo185840P, M.Ngo185841P, M.NgoAI, M.NgoAII, M.NgoAIII, M.NgoAIV, M.NgoAV, M.NgoAVIIP, M.NgoAXIP, M.NgoAORFC708P, M1.NgoAORFC717P, M2.NgoAORFC717P, M.NgoBI, M.NgoBII, M.NgoBIIIP, M.NgoBIVP, M.NgoBV, M1.NgoBVIII, M2.NgoBVIII, M.NgoBIX, M.NgoBXII, M.NgoDIII, M.NgoEI, M.NgoFVII, M.NgoGI, M.NgoGII, M.NgoGIII, M.NgoGIVP, M.NgoGV, M.NgoHIP, M.NgoHIIP, M.NgoHIIIP, M.NgoHIVP, M.NgoHVP, M.NgoHVIP; M.NgoHVIIP, M.NgoHVIII, M.NgoKVIP, M.NgoLIP, M.NgoLII, M.NgoLIIIP, M.NgoLIVP, M.NgoLVP, M.NgoMI, M.NgoMII, M.NgoMIII, M.NgoMIV, M.NgoMV, M.NgoMVIII, M.NgoMXV, M.NgoNIP, M.NgoNII, M.NgoNIIIP, M.NgoNIVP, M.NgoNVP, M.NgoPIP, M.NgoPII, M.NgoPIII, M.NgoPIVP, M.NgoPVP, M.NgoQIP, M.NgoQIIP, M.NgoQIIIP, M.NgoQIVP, M.NgoQVP, M.NgoSIP, M.NgoSII, M.NgoSIIIP, M.NgoSIVP, M.NgoSVP, M.NgoTIP, M.NgoTII, M.NgoTIIIP, M.NgoTIVP, M.NgoTVP, M.Ngo125VIIP, M.NlaI, M.NlaIII, M.NlaIV, M.NlaX, M.NlaL17IRFAP, M.NmaPhiCh1I, M.NmeAORF1453P, M.NmeAORF1500P, M1.NmeBI, M2.NmeBI, M.NmeBF13P, M.NmeBORF1033P, M.NmeBORF1290P, M.NmeSI, M.NmeST1117ORF1P, M.NmepNLE1P, M.NpuORFC221P, M.NpuORFC222P, M.NpuORFC224P, M.NpuORFC226P, M.NpuORFC228P, M.NpuORFC230P, M.NpuORFC231P, M.NpuORFC234P, M.NsiI, M.NspI, M.NspIII, M.NspV, M.NspHI, M.OihORF3333P, M.OihORF3336P, M.OkrAI, M.Pac25I, M.PaeI, M.PaeIMORF3201P, M.PaeMSHORF1P, M.Pae2164ORF7P, M.PaeR7I, M.PfIMI, M.PgiI, M.PhaI, M.PhiBssHII, M.PhiMx8I, M.Phi3TI, M.Phi3TII, M.PhoI, M.PhoII, M.PhoWORFBP, M.PhsOYDam1P, M.PhsOYDam2P, M.PhsOYDam3P, M.PhsOYDam4P, M.PhsOYDam5P, M.PleI, M.PleLFBORF8P, M.PluTDamP, M.PluTDcmP, M.PluTORF600P, M.PluTORF2710P, M.PluTORF2942P, M.Pmi16525DamP, M.Pmi16525Dam2P, M.Pmi16525ORFDP, M.PmuADam, M.PmuDam, M.Ppu21I, M.Ppu111I, M.Ppu1253I, M.PpuMI, M.PshAI, M.PspGI, M.PspPI, M.PstI, M.PvuI, M.PvuII, M.PvuRts1DamP, M.PvuRts1Dam2P, M.RcoORF690P, M.ReuORF325P, M.Rho11sI, M.Rho11sII, M.Rle39BI, M.RmeADam, M.RpaORF1026P, M.RpapRPA4P, M.Rrh4273I, M.RruMORFS5P, M.RruMORFS15P, M.RsaI, M.RshI, M.RshIII, M.RsrI, M.RsrII, M.SPBetaI, M.SPRI, M.SacI, M.SacII, M.SalI, M2.5apI, M.Sau96I, M.Sau3239I, M.Sau6782I, M.Sau3AI, M.SauLPI, M.SbaI, M.SbfI, M.Sbo13I, M.ScaI, M1.5crFI, M2.5crFI, M.SduI, M.SenPI, M.SenPhiE15P, M.SenPhiE15DamP, M.SenpCI, M.SeqORFC57P, M.SeqORFC272P, M.SeqORFC448P, M.SfaNI, M.SfeI, M.SfiI, M.Sfl2DamP, M.Sfl2DcmP, M.Sfl2ORF3300P, M.SflSf6DamP, M.SflTDamP, M.SflTDcmP, M.SflTORF3517P, M.Sfl2aI, M.SfoI, M.Sho27844P, M.SinI, M.SmaI, M.SmaII, M.SmapR478DcmP, M.SmapR478ORF272P, M.SmeIP, M1.SmuUORF504P, M2.5muUORF504P, M.SnaBI, M.SonDamP, M.SonORF4P, M.SpeI, M.SphI, M.Spn526P, M.Spn6BI, M1.Spn19FORF24P, M2.5pn19FORF24P, M.Spn19FORF927P, M.SpnHGORF4P, M.SpnORF1431P, M.SpnORF1849P, M.SpnRORF1287P, M.SpomI, M.SptAI, M.SscL1I, M.Sse9I, M.Ssl1I, M.SsoI, M.SsoII, M.Ssp6803I, M.Ssp6803ORF729P, M.Ssp6803ORF1803P, M.SspPhiBt1P, M.SssI, M.SstI, M.Ssu211I, M.Ssu212I, M1.Ssu2479I, M2.Ssu2479I, M1.Ssu4109I, M2.Ssu4109I, M1.Ssu4961I, M2.Ssu4961I, M1.Ssu8074I, M2.Ssu8074I, M1.Ssu11318I, M2.Ssu11318I, M1.SsuDAT1I, M2.SsuDAT1I, M.Sth368I, M.SthSt8IP, M.StsI, M.StyI, M.StyCDamP, M.StyCDam2P, M.StyCDam3P, M.StyCDam4P, M.StyCDcmP, M.StyD4I, M.StyDam, M.StyDam2P, M.StyDam3P, M.Sty1344Dam, M.Sty14028Dam, M.StyHCM1ORF187P, M.StyLTI, M.StyLTIII, M.StyLT2Dam, M.StyLT2DcmP, M.StyLT2FelsDamP, M.StyR27ORF154P, M.StySJI, M.StySKI, M.StySPI, M.StySQI, M.StySopEDamP, M.StyTDamP, M.StyTDam2P, M.StyTDam3P, M.StyTDam4P, M.StyTDcmP, M.SuaI, M.TaeII, M.TaqI, M.TdeII, M.TdeIII, M.TdeORF706P, M.TelBORF1578P, M.TelBORF1640P, M.TelBORF1878P, M1.TerORFS1P, M2.TerORFS1P, M.TerORFS14P, M.TerORFS18P, M.TerORFS62P, M.TerORFS122P, M.TfiTok6A1I, M.ThaI, M.ThaII, M.ThaIII, M.TliI, M.TmaI, M.TpaI, M.TrsKTI, M.TrsSI, M.TrsTI, M.TseI, M.Tsp32I, M.Tsp45I, M.Tsp509I, M.TspRI, M.Tth111I, Tth111II, M.TthHB8I, M.TthHB27P, M.TthHB27ORF41P, M.TvoORF849P, M.TvoORF1192P, M.TvoORF1400P, M.TvoORF1413P, M.TvoORF1416P, M.TwhORF771P, M.TwhTORF783P, M.Uba580P, M.Ucr1P, M.Van91II, M.VchADamP, M.Vch569BdamP, M.Vch0395Dam, M.VchK139I, M.VpaRDamP, M.VspI, M.VvuDamP, M.VvuYDamP, M.WsuORF1405P, M.WsuORF1930P, M.XamI, M.XaxCORF2436P, M.XbaI, M.XcmI, M.XcyI, M.XfaAORFC345P, M.XfaAORFC348P, M.XfaOORFC725P, M.XfaORF1804P, M.XfaTORF577P, M.XfaTORF1062P, M.XfaTORF1607P, M.XhoI, M.XhoI, M.XmaI, M.XmaIII, M.XmnI, M.XorII, M.XphI, M.YenI, M.YenSDamP, M.YenSORFC666P, M.YenWI, M.YpeDamP, M.YpeKDamP, M.YpeKORF2224P, M.YpeKORF3792P, M.YpeMDamP, M.YpeMORF1932P, M.YpeMORF3790P, M.YpeORF391P, M.YpeORF2088P, M.YpsDam.

In more preferred embodiment of the present invention, the methyltransferase is selected from the group consisting of the DNA methyltransferases M.HhaI, M.TaqI, M.BseCI and M.SssI.

The present invention also relates to a kit comprising the cofactor of the present invention and a methyltransferase as defined in the present invention or the complex of the present invention. The various compounds of the kit may be packed in one or more containers, optionally dissolved in suitable buffer for storage. A leaflet with instructions for use may be added.

The present invention also relates to a pharmaceutical composition comprising the cofactor of the present invention or the complex of the present invention and optionally a pharmaceutically acceptable carrier.

The present invention also relates to a diagnostic composition comprising the cofactor of the present invention or the complex of the present invention.

The primary solvent of the diagnostic composition is aqueous in nature. In addition, the composition may contain other ingredients or carrier for modifying or maintaining the pH, osmolarity, viscosity, clarity, color, sterility, stability, rate of dissolution, or odor of the formulation. Similarly, the composition may contain still other pharmacologically acceptable ingredients for modifying or maintaining the stability, rate of dissolution, release, or absorption of the diagnostic composition. Once the diagnostic composition has been formulated, it may be stored in sterile vials as a solution, suspension, gel, emulsion, solid, or dehydrated or lyophilized powder. Such formulations may be stored either in ready to use form or requiring reconstitution immediately prior to use.

The present invention also relates to the use of the cofactor of the present invention or the complex of the present invention for detecting sequence-specific methylation in DNA molecules. Typical uses are methods according to the teaching of the present invention such as the methods described herein.

The present invention also relates to the use of the cofactor of the present invention or the complex of the present invention for the diagnosis of a disease associated with increased or decreased DNA methylation.

The term "disease-associated with increased or decreased DNA methylation", as used herein, particularly refers to diseases such as cancer or ICF syndrome.

The present invention also relates to the use of the cofactor of the present invention or the complex of the present invention for the preparation of a diagnostic composition for the diagnosis of a disease associated with increased or decreased DNA methylation.

In a preferred embodiment of the present invention, said disease is cancer or ICF syndrome.

Preferably, the cancer is selected from the group consisting of breast cancer, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma or adenoma.

The invention is further illustrated by the following examples without being restricted by the examples:

EXAMPLES

Example 1

M.HhaI-Catalysed Coupling of Biotinylated Aziridine Cofactor 1 (A), 2 (B) and 3 (C) with the Duplex Oligodeoxynucleotide I-II Aziridine cofactors 1 and 2 with a biotin group attached to the 7 position or the aziridine cofactor 3 with a biotin group attached to the 6 position of the adenine ring are good substrates for M.HhaI (scheme 1). This is demonstrated in FIG. 1.

Solutions (400 µL) of aziridine cofactor 1, 2 or 3 (32 nmol, 80 µM), duplex oligodeoxynucleotide I-II (4 nmol, 10 µM) and M.HhaI (4.4 nmol, 11 µM) in buffer (10 mM Tris hydrochloride, pH 7.4, 50 mM sodium chloride, 0.05 mM ethylenediaminetetraacetic acid and 2 mM β-mercaptoethanol) were incubated at 37° C. The progress of the coupling reactions was monitored by anion exchange HPLC (Poros 10 HQ, 10 µm, 4.6×10 mm, Applied Biosystems). Compounds were eluted with aqueous potassium chloride (0.2 M for 5 min, followed by linear gradients to 0.4 M in 5 min, to 0.6 M in 20 min and to 1 M in 5 min) in Tris hydrochloride buffer (10 mM, pH 7.6) at a flow of 4 mL/min. Directly after mixing 1, 2 or 3 with I-II and M.HhaI compounds with smaller retention times were observed with 1 and 2 in addition to the starting duplex I-II. After different incubation times almost complete conversion to these new compounds was observed with all three cofactors and no formation of a new compound occurred in parallel control experiments without M.HhaI (not shown). These new compounds are assigned to non-covalent protein-DNA complexes between M.HhaI and the coupling products $I^1$-II, $I^2$-II and $I^3$-II based on their UV absorption ratio at 260 nm and 280 nm. The coupling products $I^1$-II, $I^2$-II and $I^3$-II were released from their protein-DNA complexes by incubation at 65° C. for 30 min and slightly smaller retention times were observed for the modified duplexes $I^1$-II, $I^2$-II and $I^3$-II compared with the starting duplex I-II.

The presence and functionality of biotin groups in $I^1$-II, $I^2$-II and $I^3$-II were verified by addition of streptavidin. Residual aziridine cofactors 1, 2 or 3 were first removed from the labelled duplexes $I^1$-II, $I^2$-II or $I^3$-II by gel filtration using NAP-5 columns (Amersham Biosciences, Freiburg, Germany) according to the instructions of the supplier. Afterwards, streptavidin (25 µg) was added to the solutions (25 µL, 0.25 nmol $I^1$-II, $I^2$-II or $I^3$-II) and incubation was performed at 37° C. for 30 min. Anion exchange HPLC (see above) revealed new major compounds with small retention times which is in accordance with the formation of complexes between streptavidin and the biotinylated duplexes $I^1$-II, $I^2$-II and $I^3$-II. In addition to these complexes, small amounts of starting duplex I-II were observed in all three cases which demonstrates that only the product duplexes can tightly interact with streptavidin.

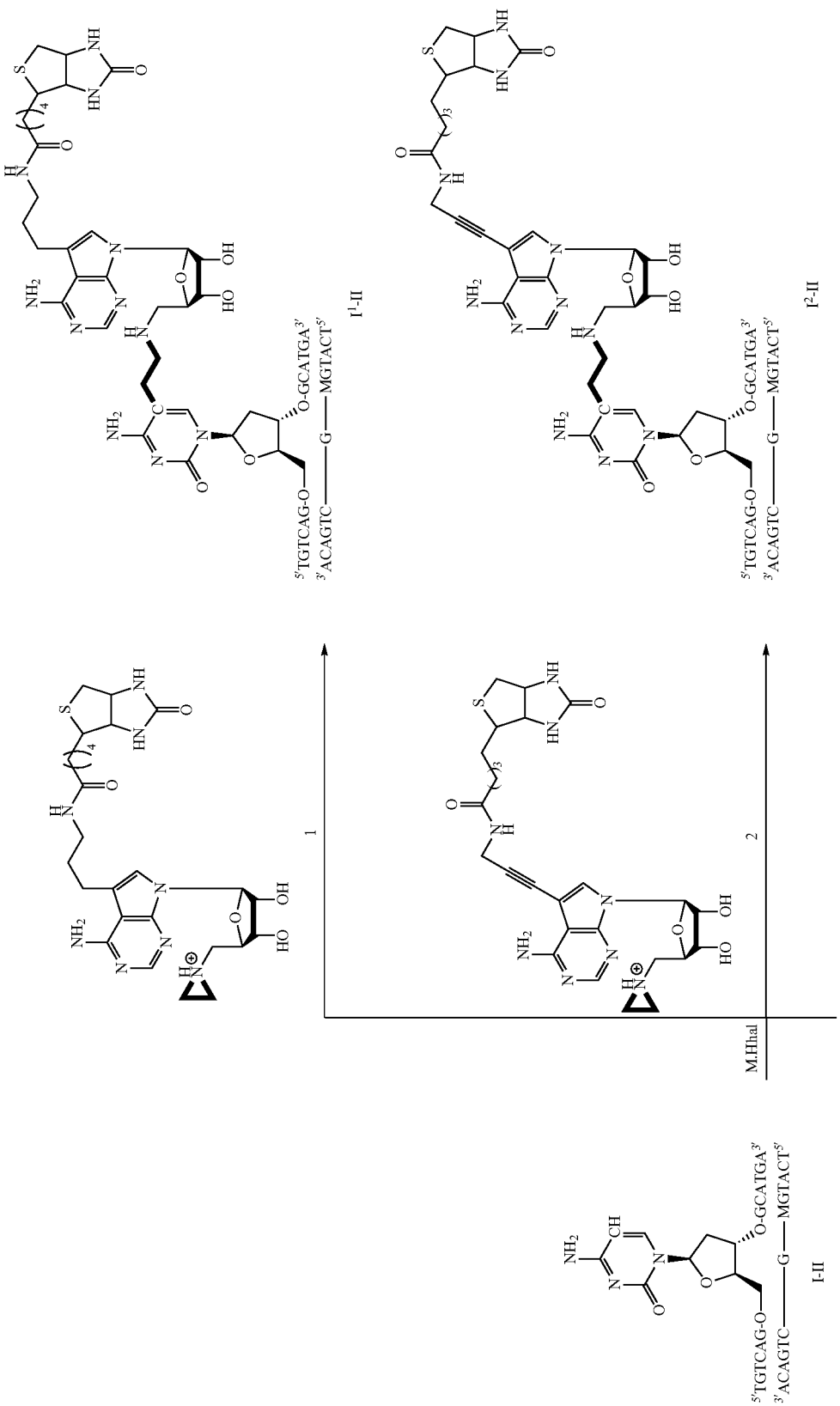
Scheme 1: M.HhaI-catalysed coupling of biotinylated aziridine cofactors 1, 2 and 3 with the short duplex oligodeoxynucleotide I-II (M = 5-methyl-2'-deoxycytidine):

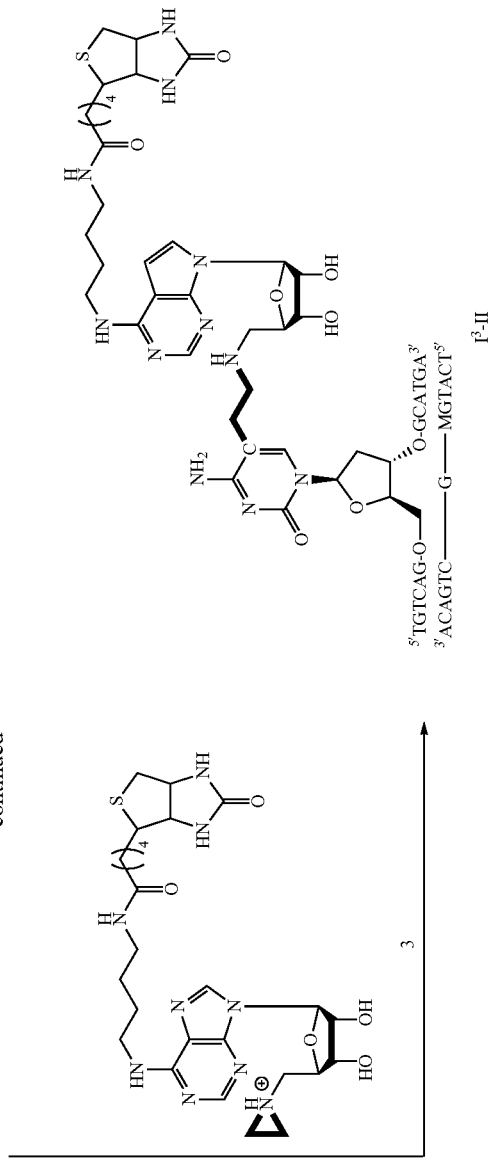

Example 2

Specific Detection of DNA Methylation

Figure 2:
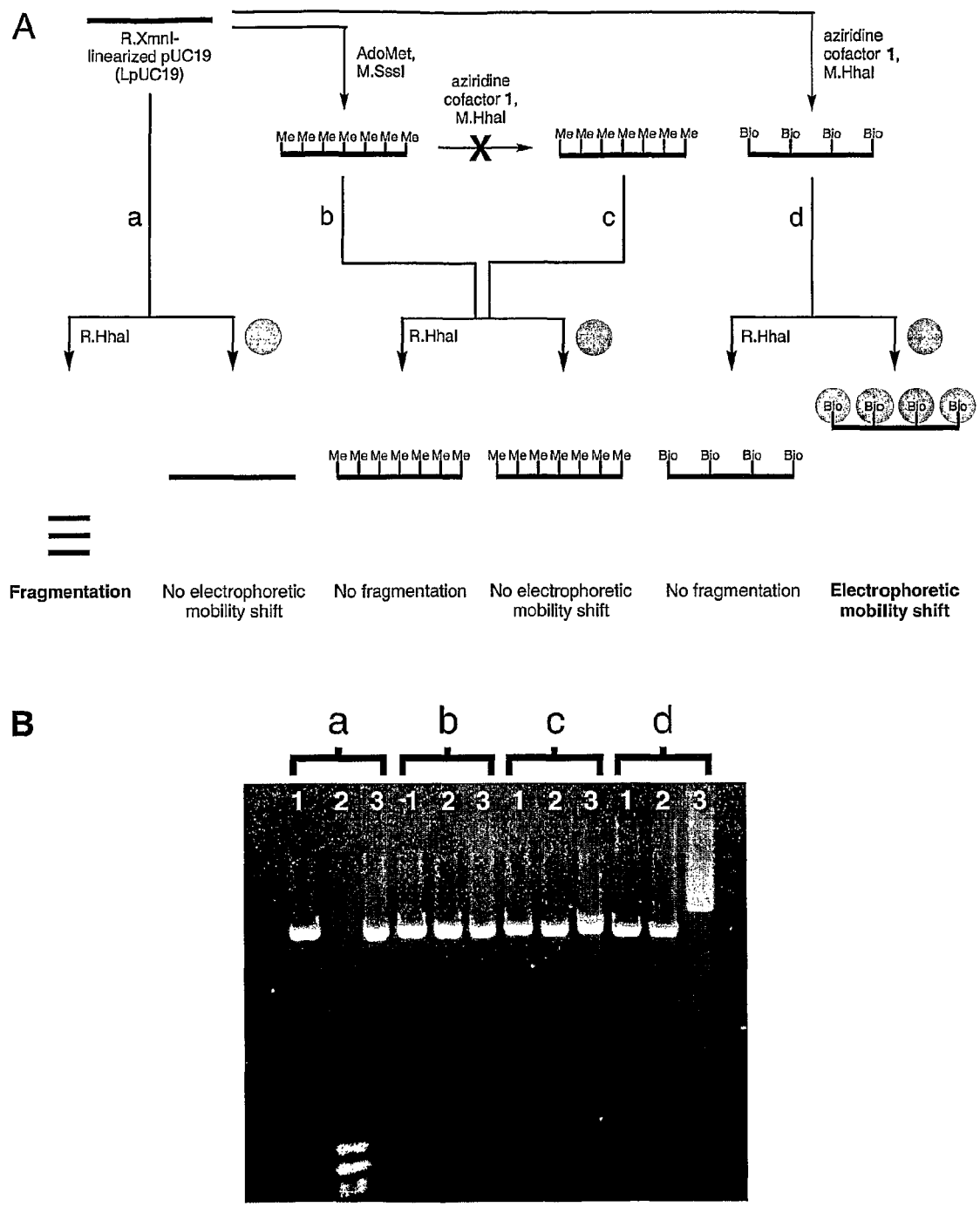
FIG. 2: Detection of CpG-methylation using aziridine cofactor 1 and M.HhaI. A: Reaction scheme (grey sphere=streptavidin); B: Agarose gel after electrophoresis of unmodified (a), CpG-methylated (b), CpG-methylated and with 1 and M.HhaI treated (c) and biotin labelled (d) linearized pUC19 plasmid DNA (LpUC19). Lanes 1: Plasmid DNA (a), (b), (c) or (d); Lanes 2: Plasmid DNA (a), (b), (c) or (d) incubated with R.HhaI; Lanes 3: Plasmid DNA (a), (b), (c), or (d) incubated with streptavidin.

The reaction with aziridine cofactor 1 and M.HhaI was used to specifically detect DNA methylation of plasmid DNA (FIG. 2). Experiments were performed with R.XmnI-linearized plasmid pUC19 DNA (LpUC19). Cytosine residues within the 5'-CG-3' DNA sequences (CpG-motives) of LpUC19 were methylated using the DNA (cytosine-5)-methyltransferase M.SssI and the natural cofactor AdoMet. Non- and CpG-methylated LpUC19 were treated with biotinylated aziridine cofactor 1 and M.HhaI, which can only alkylate the first cytosine residue within the 5'-GCGC-3' DNA sequence if this residue is not blocked by methylation of the inner CpG-motive. The different plasmids where then analyzed by treatment with the restriction endo-nuclease R.HhaI (5'-GCGC-3' recognition sequence) or streptavidin (tight binding to the biotin group) leading to fragmentation, no reaction or an electrophoretic mobility shift (FIG. 2A). Methylation-sensitive enzymatic biotinylation of linearized plasmid DNA LpUC19 is demonstrated by agarose gel electrophoresis (FIG. 2B).

A. Linearization of pUC19 Plasmid DNA

Linearization of pUC19 plasmid DNA (10 µg) was carried out with the restriction endonuclease R.XmnI (100 U) in buffer (40 µL, 10 mM Tris hydrochloride, pH 7.9, 10 mM magnesium chloride, 50 mM sodium chloride, 1 mM 1,4-dithiothreitol and 1 mg/mL bovine serum albumin) and incubation at 37° C. for 1 h.

B. CpG-Methylation

CpG-methylation of linearized pUC19 plasmid DNA LpUC19 (6 µg, from A.) was carried out with M.SssI (2.4 µg) and AdoMet (160 µM) in buffer (40 µL, 10 mM Tris hydrochloride, pH 7.9, 6 mM magnesium chloride, 50 mM sodium chloride, 1 mM 1,4-dithiothreitol and 0.6 mg/mL bovine serum albumin) at 37° C. for 1 h. The reaction was stopped by heating to 65° C. for 20 min. Methylated LpUC19 was purified using the QIAquick PCR Purification Kit (QIAGEN GmbH, Hilden, Germany) according to the instructions of the supplier and eluted with Tris hydrochloride buffer (10 mM, pH 8.5).

C. Treatment with Aziridine Cofactor 1 and M.HhaI

Non- and CpG-methylated LpUC19 plasmid DNA (2 µg each, from A. or B.), aziridine cofactor 1 (80 µM) and M.HhaI (38 µmol) in buffer (100 µL, 10 mM Tris hydro-chloride, pH 7.4, 50 mM sodium chloride, 0.05 mM ethylenediaminetetraacetic acid and 2 mM β-mercaptoethanol) were incubated at 37° C. for 2 h and then at 65° C. for 20 min. Plasmid DNA was purified using the QIAquick PCR Purification Kit (QIAGEN GmbH, Hilden, Germany) and eluted with Tris hydrochloride buffer (10 mM, pH 8.5).

D. Analysis by Restriction Endonuclease Protection

Samples (10 µL) of unmodified (A.), methylated (B. or C.) or biotinylated (C.) LpUC19 plasmid DNA (200 ng) in buffer (10 mM Tris hydrochloride, pH 7.9, 10 mM magnesium chloride, 50 mM sodium chloride, 1 mM 1,4-dithiothreitol and 1 mg/mL bovine serum albumin) were incubated with R.HhaI (2 U) at 37° C. for 1 h. DNA fragmentation was analyzed by agarose gel electrophoresis (1% agarose gel). Fragmentation by R.HhaI occurred only with unmodified LpUC19 (A.) while methylated (B. or C.) or biotinylated (C.) LpUC19 were protected against cleavage by R.HhaI (FIG. 2B, Lanes 2). This result confirms complete modifications of LpUC19.

E. Functional Biotinylation Analysis by Binding of Streptavidin

Samples (10 µL) of unmodified (A.), methylated (B. or C.) or biotinylated (C.) LpUC19 plasmid DNA (200 ng) in Tris hydrochloride buffer (10 mM, pH 8.5) were incubated with streptavidin (5 µg) at 37° C. for 1 h. Binding of steptavidin was analyzed by an electrophoretic mobility shift assay using agarose gel electrophoresis (1% agarose gel). In the presence of streptavidin (FIG. 2B, Lanes 3) a reduced electrophoretic mobility caused by the binding of streptavidin was only observed with biotinylated LpUC19 (C.) whereas unmodified LpUC19 (A.), methylated LpUC19 (B.) or methylated LpUC19 treated with aziridine cofactor 1 and M.HhaI (C.) did not change their electrophoretic mobility. This result clearly confirms that the labelling reaction with aziridine cofactor 1 and M.HhaI is sequence-specific and blocked by CpG-methylation. Thus, this system can be used to distinguish between non- and CpG-methylated DNA sequences.

Example 3

Synthesis of Aziridine Cofactor 1

The synthesis of cofactor 1 was carried out as shown in scheme 2. Details of the synthesis are given below (the IUPAC numbering for purines is used).

Scheme 2: Synthesis of aziridine cofactor 1.

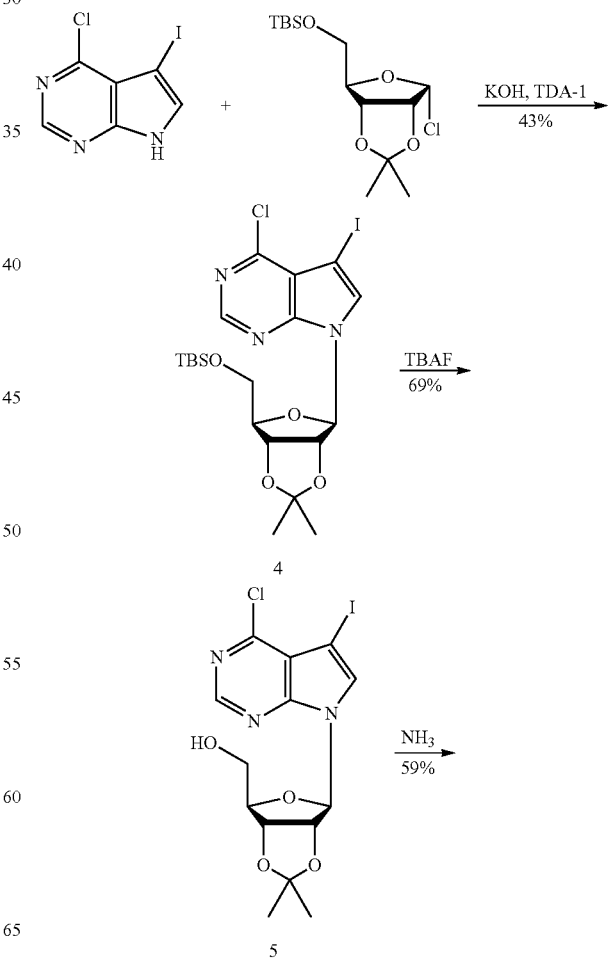

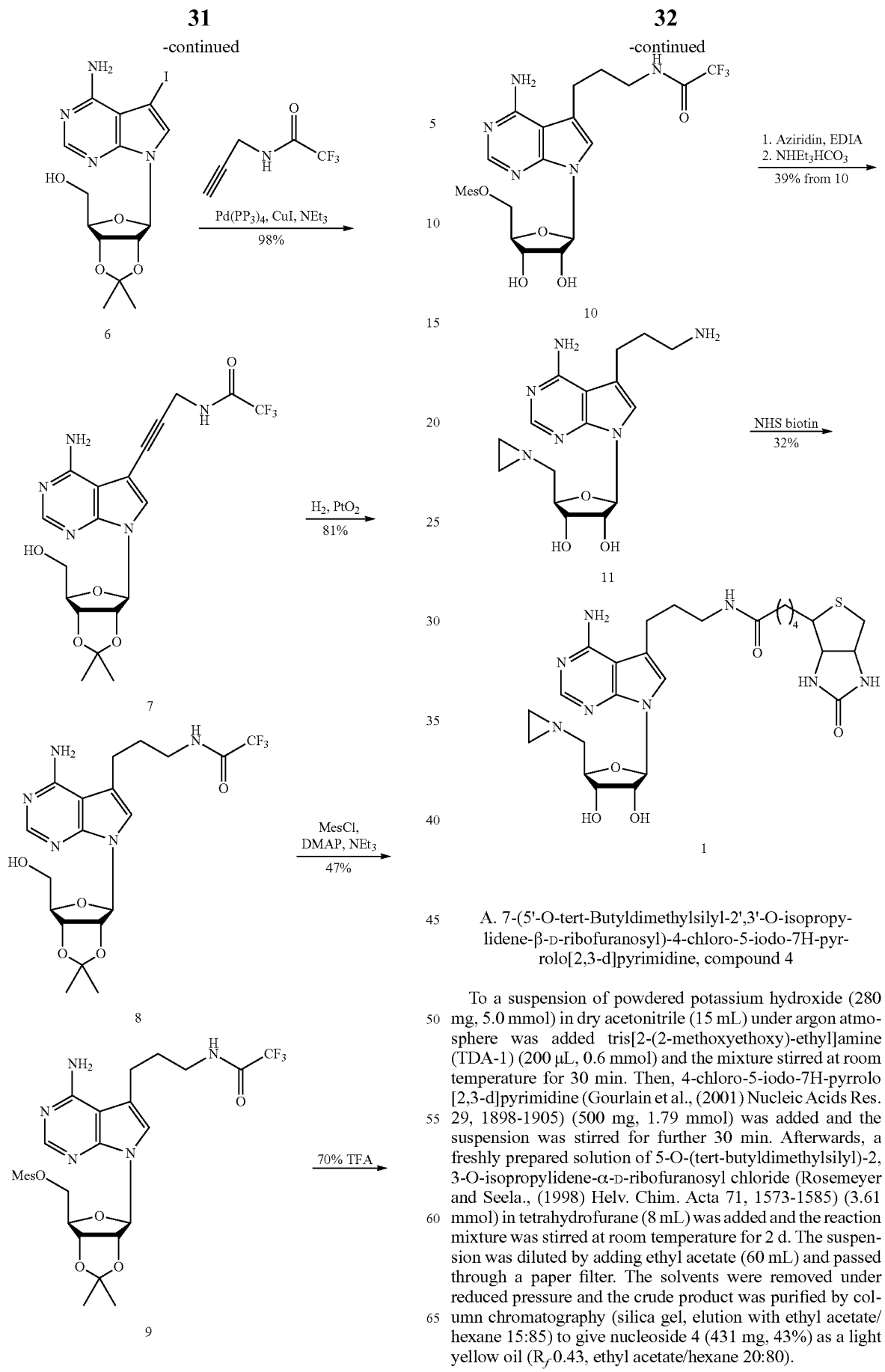

A. 7-(5'-O-tert-Butyldimethylsilyl-2',3'-O-isopropylidene-β-D-ribofuranosyl)-4-chloro-5-iodo-7H-pyrrolo[2,3-d]pyrimidine, compound 4

To a suspension of powdered potassium hydroxide (280 mg, 5.0 mmol) in dry acetonitrile (15 mL) under argon atmosphere was added tris[2-(2-methoxyethoxy)-ethyl]amine (TDA-1) (200 μL, 0.6 mmol) and the mixture stirred at room temperature for 30 min. Then, 4-chloro-5-iodo-7H-pyrrolo[2,3-d]pyrimidine (Gourlain et al., (2001) Nucleic Acids Res. 29, 1898-1905) (500 mg, 1.79 mmol) was added and the suspension was stirred for further 30 min. Afterwards, a freshly prepared solution of 5-O-(tert-butyldimethylsilyl)-2,3-O-isopropylidene-α-D-ribofuranosyl chloride (Rosemeyer and Seela., (1998) Helv. Chim. Acta 71, 1573-1585) (3.61 mmol) in tetrahydrofurane (8 mL) was added and the reaction mixture was stirred at room temperature for 2 d. The suspension was diluted by adding ethyl acetate (60 mL) and passed through a paper filter. The solvents were removed under reduced pressure and the crude product was purified by column chromatography (silica gel, elution with ethyl acetate/hexane 15:85) to give nucleoside 4 (431 mg, 43%) as a light yellow oil ($R_f$ 0.43, ethyl acetate/hexane 20:80).

¹H-NMR (500 MHz, CDCl₃): δ=0.12 (s, 3H, SiCH₃a), 0.12 (s, 3H, SiCH₃b), 0.92 (s, 9H, SiC(CH₃)₃), 1.38 (s, 3H, isopropylidene-CH₃a), 1.65 (s, 3H, isopropylidene-CH₃b), 3.81 (dd, ²J=11.29 Hz, ³J=3.05 Hz, 1H, H5' a), 3.92 (dd, ²J=11.60 Hz, ³J=2.75 Hz, 1H, H5' b), 4.40 (q, ³J=2.75 Hz, 1H, H4'), 4.90 (dd, ³J=2.44 Hz, ³J=6.10 Hz, 1H, H3'), 4.94 (dd, ³J=3.05 Hz, ³J=6.10 Hz, 1H, H2'), 6.43 (d, ³J=3.05 Hz, 1H, H1'), 7.78 (s, 1H, H6), 8.65 (s, 1H, H2); ¹³C-NMR (100 MHz, CDCl₃): δ=−5.379 (SiCH₃a), −5.219 (SiCH₃b), 18.427 (SiC(CH₃)₃), 25.376 (isopropylidene-CH₃a), 25.983 (SiC(CH₃)₃), 27.318 (isopropylidene-CH₃b), 52.125 (C5), 63.481 (C5'), 80.785 (C4'), 85.383 (C3'), 86.194 (C2'), 90.769 (C1'), 114.020 (ispropylidene-C(CH₃)₂), 117.237 (C9), 131.886 (C6), 150.252 (C2), 150.859 (C8), 152.399 (C4).

B. 4-Chloro-5-iodo-7-(2',3'-O-isopropylidene-β-D-ribofuranosyl)-7H-pyrrolo-[2,3-d]-pyrimidine, compound 5

A solution of nucleoside 4 (348 mg, 0.61 mmol) in tetrahydrofurane (10 mL) was cooled to 0° C. After addition of tetrabutylammonium fluoride (TBAF) (291 mg, 0.92 mmol) the reaction mixture was stirred at 0° C. for 2 h. The reaction mixture was allowed to warm up to room temperature and the solvent was removed under reduced pressure. The residue was dissolved in ethyl acetate (10 mL) and the organic layer was washed with water (2 mL) and brine (2 mL). The organic layer was dried over magnesium sulfate, filtered and the solvent was removed under reduced pressure. Purification by column chromatography (silica gel, elution with ethyl acetate/hexane 40:60) gave the desired compound 5 (192 mg, 69%) as a light yellow foam (R_f 0.23, ethyl acetate/hexane 40:60).

¹H-NMR (500 MHz, CDCl₃): δ=1.37 (s, 3H, isopropylidene-CH₃a), 1.64 (s, 3H, isopropylidene-CH₃b), 3.81 (t, ²J=³J=10.68 Hz, 1H, H5' a), 3.95 (dd, ²J=12.51 Hz, ³J=1.83 Hz, 1H, H5' b), 4.47-4.49 (m, 1H, H4'), 4.76 (d, ³J=10.07 Hz, 1H, 5'-OH), 5.09 (dd, ³J=2.14, ³J=6.10, 1H, H3'), 5.19 (dd, ³J=4.88 Hz, ³J=6.10 Hz, 1H, H2'), 5.88 (d, ³J=4.88 Hz, 1H, H1'), 7.51 (s, 1H, H6), 8.63 (s, 1H, H2); ¹³C-NMR (75 MHz, CDCl₃): δ=25.298 (isopropylidene-CH₃a), 27.542 (isopropylidene-CH₃b), 51.941 (C5), 63.085 (C5'), 81.162 (C4'), 83.279 (C3'), 85.762 (C2'), 94.582 (C1'), 114.436 (isopropylidene-C(CH₃)₂), 118.719 (C9), 134.551 (C6), 149.558 (C2), 150.597 (C8), 153.674 (C4); ESI-MS m/z (relative intensity): 452.3 (9) [M+H]⁺, 280.5 (100) [4-chloro-5-iodo-7H-pyrrolo[2,3-d]pyrimidine+H]⁺.

C. 4-Amino-5-iodo-7-(2',3'-O-isopropylidene-β-D-ribofuranosyl)-7H-pyrrolo-[2,3-d]-pyrimidine, compound 6

A solution of nucleoside 5 (981 mg, 2.17 mmol) in methanol (80 mL) was cooled to 0° C. and saturated with gaseous ammonia. A pre-cooled autoclave was filled with the solution, sealed and heated to 80-85° C. overnight. The autoclave was allowed to cool to room temperature, the solution was removed and the solvent was evaporated under reduced pressure. The crude product was purified by column chromatography (silica gel, elution with methanol/methylene chloride 5:95) to give nucleoside 6 (557 mg, 59%) as a light yellow foam (R_f 0.21, methanol/methylene chloride 5:95).

¹H-NMR (400 MHz, [D₆]DMSO): δ=1.31 (s, 3H, isopropylidene-CH₃a), 1.53 (s, 3H, isopropylidene-CH₃b), 3.49-3.59 (m 2H, H5'), 4.10-4.13 (m, 1H, H4'), 4.90 (dd, ³J=3.02 Hz, ³J=6.32 Hz, 1H, H3'), 5.11 (dd, ³J=3.29 Hz, ³J=6.31 Hz, 1H, H2'), 5.16 (t, ³J=5.49 Hz, 1H, 5'-OH), 6.19 (d, ³J=3.30 Hz, 1H, H1'), 6.76 (s, br, 2H, NH₂), 7.69 (s, 1H, H6), 8.12 (s, 1H, H2); ¹³C-NMR (75 MHz, [D₆]DMSO): δ=25.678 (isopropylidene-CH₃a), 27.589 (isopropylidene-CH₃b), 52.837 (C5), 62.046 (C5'), 81.432 (C3'), 84.025 (C2'), 85.985 (C4'), 89.276 (C1'), 103.665 (C9), 113.659 (isopropylidene-C(CH₃)₂), 127.810 (C6), 150.218 (C8), 152.653 (C2), 157.761 (C4); ESI-MS m/z (relative intensity): 433.2 (100) [M+H], 261.5 (8) [4-Amino-5-iodo-7H-pyrrolo[2,3-d]-pyrimidine+H].

D. 4-Amino-7-(2',3'-O-isopropylidene-β-D-ribofuranosyl)-5-[1''-(3''-trifluoro-acetamido)prop-1-ynyl]-7H-pyrrolo[2,3-d]pyrimidine, compound 7

To a solution of 6 (295 mg, 0.68 mmol) in dry dimethylformamide (10 mL) under argon atmosphere were added copper(I) iodide (39.4 mg, 0.21 mmol), 3-trifluoro-acetamido-prop-1-in (Trybulski et al., (1993) J. Med. Chem. 36, 3533-3541) (1.05 g, 6.95 mmol), triethylamine (290 µL, 2.08 mmol) and tetrakis(triphenylphosphine)-palladium (118 mg, 0.10 mmol). The reaction mixture was stirred at room temperature overnight. Then, the reaction was quenched by adding Dowex 1×8 resin (1.3 g, loaded with hydrogencarbonate) and methanol/methylene chloride (1:1 mixture, 15 mL). After stirring at room temperature for 40 min the mixture was filtrated through Celite and the solvent was removed under reduced pressure. The crude product was purified by column chromatography (silica gel, elution with methanol/methylene chloride 7:93) to give nucleoside 7 (305 mg, 98%) as a light yellow foam (R_f 0.23, methanol/methylene chloride 7:93).

¹H-NMR (400 MHz, [D₆]DMSO): δ=1.31 (s, 3H, isopropylidene-CH₃a), 1.53 (s, 3H, isopropylidene-CH₃b), 3.51-3.57 (m, 2H, H5'), 4.13-4.16 (m, 1H, H4'), 4.32 (d, ³J=5.22 Hz, 2H, H3''), 4.91 (dd, ³J=2.75 Hz, ³J=6.04 Hz, 1H, H3'), 5.12 (dd, ³J=3.30 Hz, ³J=6.05 Hz, 1H, H2'), 5.17, (t, ³J=5.36 Hz, 1H, 5'-OH), 6.19 (d, ³J=3.30 Hz, 1H, H1'), 7.95 (s, 1H, H6), 8.14 (s, 1H, H2), 10.10 (t, ³J=5.22 Hz, 1H, 3''—NH); ¹³C-NMR (100 MHz, [D₆]DMSO): δ=25.125 (isopropylidene-CH₃a), 27.029 (isopropylidene-CH₃b), 29.882 (C3''), 61.486 (C5'), 75.846 (C2''), 80.914 (C3'), 83.554 (C2'), 85.579 (C4'), 86.892 (C1''), 88.948 (C1'), 94.417 (C5), 102.049 (C9), 112.912 (isopropylidene-C(CH₃)₂), 115.624 (q, ¹J=286 Hz, CF₃), 126.825 (C6), 149.075 (C8), 152.717 (C2), 156.070 (q, ²J=36.4 Hz, COCF₃), 157.299 (C4); ¹⁹F-NMR (376 MHz, [D₆]DMSO): δ=−69.72 (CF₃); ESI-MS m/z (relative intensity): 456.4 (12) [M+H]⁺, 284.4 (100) [4-amino-541'-(3'-trifluoroacetamido)prop-1-ynyl]-7H-pyrrolo[2,3-d]pyrimidine+H]⁺.

E. 4-Amino-7-(2',3'-O-isopropylidene-β-D-ribofuranosyl)-5-[1''-(3''-trifluoro-acetamido)propyl]-7H-pyrrolo[2,3-d]pyrimidine, compound 8

To a solution of nucleoside 7 (305 mg, 0.67 mmol) in methanol (75 mL) was added platinum(IV) oxide (10 mg, 44 µmol) and hydrogen gas was bubbled through the solution at room temperature for 5 h. The catalyst was removed by filtration through Celite and washed with methanol. The solvent was removed under reduced pressure and the crude product purified by column chromatography (silica gel, elution with methanol/methylene chloride 5:95). Nucleoside 8 (248 mg, 81%) was obtained as a light yellow solid (R_f 0.30, methanol/methylene chloride 5:95).

¹H-NMR (400 MHz, [D₆]DMSO): δ=1.31 (s, 3H, isopropylidene-CH₃a), 1.53 (s, 3H, isopropylidene-CH₃b), 1.75-1.82 (m, 2H, H2''), 2.75-2.79 (m, 2H, H1''), 3.25-3.30 (m, 2H, H3''), 3.48-3.58 (m, 2H, H5'), 4.06-4.09 (m, 1H, H4'), 4.88

(dd, $^3J=3.02$ Hz, $^3J=6.32$ Hz, 1H, H3'), 5.11 (dd, $^3J=3.57$ Hz, $^3J=6.32$ Hz, 1H, H2'), 5.16 (t, $^3J=5.64$ Hz, 1H, 5'-OH), 6.14 (d, $^3J=3.84$ Hz, 1H, H1'), 6.65 (s, br, 2H, NH$_2$), 7.14 (s, 1H, H6), 8.04 (s, 1H, H2), 9.43 (t, $^3J=5.36$ Hz, 3"—NH); $^{13}$C-NMR (75 MHz, [D$_6$]DMSO): δ=23.529 (C2"), 25.695 (isopropylidene-CH$_3$a), 27.622 (isopropylidene-CH$_3$b), 29.756 (C1"), 29.258 (C3"), 62.141 (C5'), 81.527 (C3'), 83.620 (C2'), 85.421 (C4'), 89.070 (C1'), 102.459 (C9), 113.698 (isopropylidene-C(CH$_3$)$_2$), 116.859 (q, $^1J=226.7$ Hz, CF$_3$), 115.348 (C5), 120.051 (C6), 150.858 (C8), 151.691 (C2), 156.696 (q, $^2J=35.7$ Hz, COCF$_3$), 157.838 (C4); $^{19}$F-NMR (376 MHz, [D$_6$]DMSO): δ=−74.74 (CF$_3$); ESI-MS: m/z (relative intensity): 460.4 (88) [M+H], 288.5 (100) [4-amino-5-[1'-(3'-trifluoroacetamido)propyl]-7H-pyrrolo[2,3-c]pyrimidine+H]$^+$.

F. 4-Amino-7-(2',3'-O-isopropylidene-5'-O-mesyl-β-D-ribofuranosyl)-5-[1"-(3"-trifluoroacetamido)propyl]-7H-pyrrolo[2,3-d]pyrimidine, compound 9

To a solution of nucleoside 8 (72 mg, 157 μmol) in dry methylene chloride (7 mL) under argon atmosphere were added dimethylaminopyridine (DMAP) (20 mg, 164 μmol) and triethylamine (66 μL, 474 μmol) and the mixture was cooled to 0° C. in an ice bath. Methanesulfonyl chloride (MesCl) (40 μL, 515 μmol) was slowly added and the reaction mixture was stirred at 0° C. for 2 h. Then, the reaction was quenched by adding an ice-cold, saturated sodium hydrogencarbonate solution (1 mL) and the organic phase was removed. The aqueous layer was extracted with ice-cold chloroform (3×2 mL) and the combined organic layers were dried over magnesium sulfate. After filtration the solvent was removed under reduced pressure and the crude product was purified by column chromatography (silica gel, methanol/methylene chloride 7:93) to give nucleoside 9 (40 mg, 47%) as a light yellow solid (R$_f$ 0.47, methanol/methylene chloride 10:90).

$^1$H-NMR (400 MHz, [D$_6$]DMSO): δ=1.33 (s, 3H, isopropylidene-CH$_3$a), 1.54 (s, 3H, isopropylidene-CH$_3$b), 1.77-1.81 (m, 2H, H2"), 2.77 (t, $^3J=7.42$ Hz, 2H, H1"), 3.12 (s, 3H, mesyl-CH$_3$), 3.24-3.32 (m, 2H, H3"), 4.31-4.35 (m, 2H, H5'), 4.38-4.42 (m, 1H, H4'), 4.99 (dd, $^3J=2.75$ Hz, $^3J=6.32$ Hz, 1H, H3'), 5.23 (dd, $^3J=3.02$ Hz, $^3J=6.32$ Hz, 1H, H2'), 6.23 (d, $^3J=3.02$ Hz, 1H, H1'), 6.68 (s, br, 2H, NH$_2$), 7.13 (s, 1H, H6), 8.07 (s, 1H, H2), 9.42 (t, br, 1H, 3"-NH); $^{19}$F-NMR (376 MHz, [D$_6$]DMSO): δ=−74.74 (CF$_3$).

G. 4-Amino-7-(5'-O-mesyl-β-D-ribofuranosyl)-5-[1"-(3"-trifluoroacet-amido)propyl]-7H-pyrrolo[2,3-d]pyrimidine, compound 10

A solution of nucleoside 9 (40 mg, 74 μmol) in aqueous trifluoroacetic acid (TFA) (70%, 2 mL) was stirred at room temperature for 45 min. The solvent was removed under reduced pressure and remaining solvent co-evaporated with ethanol and methylene chloride. The crude product 10 (R$_f$ 0.22, methanol/methylene chloride 10:90) was directly used in the following reaction.

$^{19}$F-NMR (376 MHz, [D$_6$]DMSO): δ=−74.75 (CF$_3$).

H. 4-Amino-7-(5'-N-aziridinyl-5'-deoxy-β-D-ribofuranosyl)-5-[1"-(3"-amino-propyl)]-7H-pyrrolo[2,3-d]pyrimidine, compound 11

Crude nucleoside 10 from the previous step was dissolved in a mixture of dry aziridine (Gabriel, (1888) Chem. Ber. 21, 2664-2669; Gabriel and Stelzner, (1895) Chem. Ber. 28, 2929-2938) (1 mL, 16.3 mmol) and N-ethyldiisopropylamine (EDIA) (300 μL, 1.8 mmol) under argon atmosphere and the reaction mixture was stirred at room temperature for 4 d. The reaction progress was monitored by analytical reverse-phase HPLC (Prontosil-ODS, 5 μm, 120 Å, 250×4.6 mm, Bischoff, Leonberg, Germany). Compounds were eluted with acetonitrile (7% for 5 min, followed by linear gradients to 31.5% in 10 min, to 35% in 15 min and to 70% in 5 min) in triethylammonium acetate buffer (0.1 M, pH 7.0) at a flow of 1 mL/min. The product 11 eluted with a retention time of 10.2 min (UV detection at 280 nm and 300 nm). Volatile compounds were removed under reduced pressure and the residue was dissolved in triethylammonium hydrogencarbonate buffer (4 mL, 0.1 M, pH 8.6). The crude product was purified by preparative reverse-phase HPLC (Prontosil-ODS, 5 μm, 120 Å, 250×8 mm, Bischoff, Leonberg, Germany). Compounds were eluted with acetonitrile (7% for 5 min, followed by linear gradients to 21% in 15 min and to 70% in 5 min) in triethylammonium hydrogencarbonate buffer (0.01 M, pH 8.6) at a flow of 3 mL/min. Fractions containing the product 11 (retention time 16.8 min, UV detection at 280 nm and 310 nm) were combined and stored at −80° C. The amount of product 11 (10 mg, 39% from 9) in the combined fractions was determined by UV spectroscopy using the published extinction coefficient $\epsilon^{278}$=8500 L mol$^{-1}$ cm$^{-1}$ of 4-amino-7-(2'-deoxy-β-D-erythro-pentofuranosyl)-5-[1"-(5"-trifluoroacetamido)pentyl]-7H-pyrrolo[2,3-d]pyrimidine (Seela et al., (2000) Helv. Chim. Acta 83, 910-927).

I. 4-Amino-7-(5'-N-aziridinyl-5'-deoxy-β-D-ribofuranosyl)-5-[1"-(N"-biotinyl)-3"-aminopropyl]-7H-pyrrolo[2,3-d]pyrimidine, compound 1

To a solution (12 mL) of nucleoside 11 (10 mg, 29 μmol) in triethylammonium hydrogencarbonate buffer (0.1 M, pH 8.6) containing acetonitrile was added N-hydroxysuccinimidyl biotin (NHS biotin) (10.2 mg, 30 μmol) in dimethylsulfoxide (500 μL). The reaction mixture was stirred at room temperature for 2 h. The progress of the reaction was monitored by analytical reverse-phase HPLC (Prontosil-ODS, 5 μm, 120 Å, 250×4.6 mm, Bischoff, Leonberg, Germany). Compounds were eluted with acetonitrile (7% for 5 min followed by linear gradients to 31.5% in 10 min, to 35% in 15 min and to 70% in 5 min) in triethylammonium acetate buffer (0.1 M, pH 7.0) at a flow of 1 mL/min. The product 1 eluted with a retention time of 20.8 min (UV detection at 280 nm and 300 nm). The crude product was purified by preparative reverse-phase HPLC (Prontosil-ODS, 5 μm, 120 Å, 250×8 mm, Bischoff, Leonberg, Germany). Compounds were eluted with acetonitrile (7% for 5 min, followed by linear gradients to 31.5% in 5 min, to 35% in 10 min and to 70% in 5 min) in triethylammonium hydrogencarbonate buffer (0.01 M, pH 8.6) at a flow of 3 mL/min. Fractions containing the product 1 (retention time 14.8 min, UV detection at 280 nm and 300 nm) were combined and the solvent was removed by lyophilization. The aziridine cofactor 1 (5.2 mg, 32%) was obtained as a white solid.

$^1$H-NMR (300 MHz, [D$_6$]DMSO): δ=1.10-1.15 (m, 2H, aliphatic biotin-H), 1.25-1.35 (m, 4H, aziridine-H), 1.45-1.55 (m, 2H, aliphatic biotin-H), 1.55-1.63 (m, 2H, aliphatic biotin-H), 1.64-1.72 (m, 2H, H2"), 2.04-2.06 (m, 2H, aliphatic biotin-H), 2.28-2.34 (m, 2H, H5' a), 2.46-2.50 (m, 2H, H5' b), 2.54-2.58 (m, 1H, biotin-SCH$_2$a), 2.72-2.77 (m, 2H, H1"), 2.77-2.83 (m, 1H, biotin-SCH$_2$b), 3.05-3.16 (m, 3H, biotin-SCH, H3"), 3.89-3.94 (m, 1H, H4'), 4.08-4.15 (m, 2H, biotin-SCHRCH, H3'), 4.25-4.34 (m, 2H, biotin-SCH$_2$CH, H2'), 6.05 (d, $^3J=5.69$ Hz, 1H, H1'), 6.35 (s, 1H, biotin-NHa), 6.42 (s, 1H, biotin-NHb), 6.53 (s, 2H, NH$_2$), 7.10 (s, 1H, H6), 7.79 (t, $^3J=5.69$ Hz, 1H, 3"—NH), 8.03 (s, 1H, H2); ESI-MS: m/z (relative intensity): 575.25 (100) [M+H]$^+$, 418.18 (7) [4-amino-541'-(N-biotinyl)-3'-aminopropyl]-7H-pyrrolo[2,3-d]pyrimidine+H]$^+$.

Example 4

Synthesis of Aziridine Cofactor 2

The synthesis of cofactor 2 was carried out as shown in scheme 3. Details of the synthesis are given below (the IUPAC numbering for purines is used).

Scheme 3: Synthesis of aziridine cofactor 2.

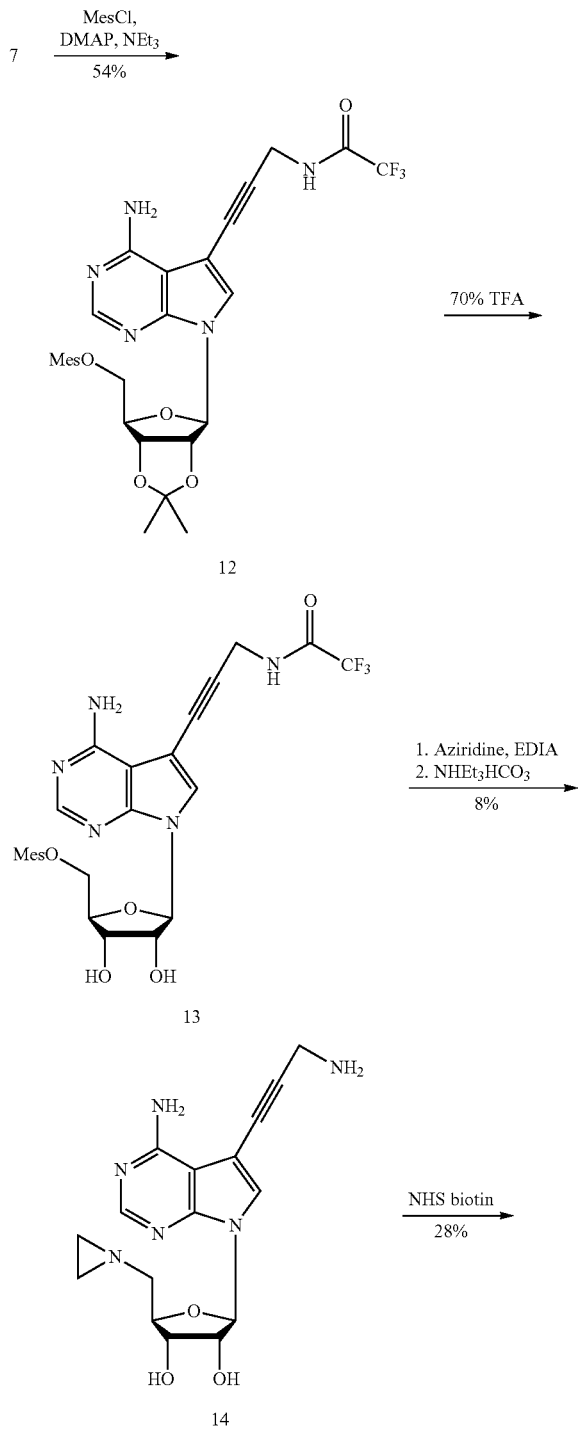

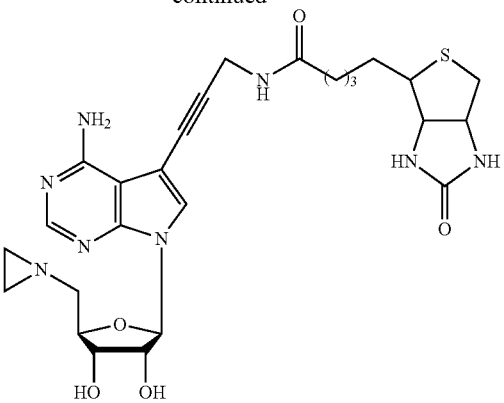

A. 4-Amino-7-(2',3'-O-isopropylidene-5'-O-mesyl-β-D-ribofuranosyl)-5-[1"-(3"-trifluoroacetamido)prop-1-ynyl]-7H-pyrrolo[2,3-d]pyrimidine, compound 12

To a solution of nucleoside 7 (100 mg, 220 μmol, example 3D) in dry methylene chloride (10 mL) under argon atmosphere were added dimethylaminopyridine (DMAP) (26.8 mg, 220 μmol) and triethylamine (92 μL, 660 μmol). After cooling the solution to 0° C. methanesulfonyl chloride (MesCl) (25.2 μl, 330 μmol) was slowly added and the reaction mixture was stirred at 0° C. for 1.5 h. Then, the reaction was quenched by adding an ice-cold, saturated sodium hydrogencarbonate solution (2 mL). The organic layer was removed and the aqueous layer was extracted with ice-cold chloroform (3×4 mL). The combined organic layers were dried over magnesium sulfate. After filtration the solvent was removed under reduced pressure and the crude product was purified by column chromatography (silica gel, methanol/methylene chloride 7:93) to give nucleoside 12 (63 mg, 54%) as yellow foam ($R_f$ 0.39, methanol/methylene chloride 10:90).

$^1$H-NMR (400 MHz, [D$_6$]DMSO): δ=1.32 (s, 3H, isopropylidene-CH$_3$a), 1.54 (s, 3H, isopropylidene-CH$_3$b), 3.13 (s, 3H, mesyl-CH$_3$), 4.32 (d, $^3J$=5.22 Hz, 2H, H3"), 4.33-4.37 (m, 2H, H5'), 4.40-4.43 (m, 1H, H4'), 5.02 (dd, $^3J$=3.03 Hz, $^3J$=6.32, 1H, H3'), 5.26 (dd, $^3J$=2.35 Hz, $^3J$=6.32, 1H, H2'), 6.25 (d, $^3J$=2.75 Hz, 1H, H1'), 7.74 (s, 1H, H6), 8.15 (s, 1H, H2), 10.11 (t, $^3J$=5.22 Hz, 1H, 3"-NH); $^{19}$F-NMR (376 MHz, [D$_6$]DMSO): δ=−74.317 (CF$_3$).

B. 4-Amino-7-(5'-O-mesyl-β-D-ribofuranosyl)-5-[1"-(3"-trifluoroacetamido)-prop-1-ynyl]-7H-pyrrolo[2,3-d]pyrimidine, compound 13

A solution of nucleoside 12 (48 mg, 90 μmol) in aqueous trifluoroacetic acid (TFA) (70%, 3 mL) was stirred at room temperature overnight. The solvent was removed under reduced pressure and remaining solvent co-evaporated twice with ethanol and once with methylene chloride. The product 13 ($R_f$ 0.38, methanol/methylene chloride 10:90) was directly used in the following reaction.

$^1$H-NMR (300 MHz, [D$_6$]DMSO): δ=3.19 (s, 3H, mesyl-CH$_3$), 3.60-4.00 (m, 3H, H5' and H4'), 4.10-4.16 (m, 1H, H3'), 4.33 (d, $^3J$=5.19 Hz, 2H, H3"), 4.40-4.44 (m, 1H, H2'), 6.11 (d, $^3J$=5.69 Hz, 1H, H1'), 7.86 (s, 1H, H6), 8.29 (s, 1H, H2), 10.12 (s, br, 1H, 3"—NH); $^{19}$F-NMR (282 MHz, [D$_6$]DMSO): δ=−74.293 (CF$_3$).

C. 4-Amino-7-(5'-N-aziridinyl-5'-deoxy-β-D-ribo-furanosyl)-5-[1''-(3''-aminoprop-1-ynyl)]-7H-pyrrolo[2,3-d]pyrimidine, compound 14

Crude nucleoside 13 (41 mg, 83 μmol) from the previous step was dissolved in a mixture of dry aziridine (Gabriel, (1888) Chem. Ber. 21, 2664-2669; Gabriel and Stelzner, (1895) Chem. Ber. 28, 2929-2938) (1 mL, 16.3 mmol) and N-ethyldiiso-propylamine (EDIA) (300 μl, 1.8 mmol) under argon atmosphere and stirred at room temperature for 4 d. The reaction progress was monitored by analytical reverse-phase HPLC (Prontosil-ODS, 5 μm, 120 Å. 250×4.6 mm, Bischoff, Leonberg, Germany). Compounds were eluted with acetonitrile (7% for 5 min, followed by linear gradients to 31.5% in 10 min, to 35% in 15 min and to 70% in 5 min) in triethylammonium acetate buffer (0.1 M, pH 7.0) at a flow of 1 mL/min. The product 14 eluted with a retention time of 13.5 min (UV detection at 254 nm and 280 nm). Volatile compounds were removed under reduced pressure and the residue was dissolved in triethylammonium hydrogencarbonate buffer (0.01 M, pH 8.6). The crude product was purified by preparative reverse-phase HPLC (Prontosil-ODS, μm, 120 Å, 250×8 mm, Bischoff, Leonberg, Germany). Compounds were eluted with acetonitrile (7% for 5 min, followed by linear gradients to 28% in 5 min, to 42% in 15 min and to 70% in 5 min) in triethylammonium hydrogencarbonate buffer (0.01 M, pH 8.6) at a flow of 3 mL/min. Fractions containing the product 14 (retention time 15.7 min, UV detection at 280 nm and 300 nm) were combined. The amount of product 14 (2.3 mg, 8.1%) in the combined fractions (12.5 mL) was determined by UV spectroscopy using the published extinction coefficient $\epsilon^{278}=14200$ L mol$^{-1}$ cm$^{-1}$ of 4-amino-7-(2'-deoxy-β-D-erythropentofuranosyl)-5-[1''-(3''-trifluoroacetamido)prop-1-ynyl]-7H-pyrrolo[2,3-d]pyrimidine (Seela and Zulauf, (1999) Helv. Chim. Acta 82, 1878-1898).

D. 4-Amino-7-(5'-N-aziridinyl-5'-deoxy-β-D-ribo-furanosyl)-5-[1''-(N''-biotinyl)-3''-aminoprop-1-ynyl]-7H-pyrrolo[2,3-d]pyrimidine, compound 2

To a solution (12.5 mL) of nucleoside 14 (2.3 mg, 6.7 μmol) in triethylammonium hydrogencarbonate buffer (0.01 M, pH 8.6) containing acetonitrile was added N-hydroxysuccinimidyl biotin (NHS biotin) (15 mg, 44 μmol) in dimethylsulfoxide (400 μL). The reaction mixture was stirred at room temperature for 2 h. The progress of the reaction was monitored by analytical reverse-phase HPLC (Prontosil-ODS, 5 μm, 120 Å, 250×4.6 mm, Bischoff, Leonberg, Germany). Compounds were eluted with acetonitrile (7% for 5 min followed by linear gradients to 31.5% in 10 min, to 35% in 15 min and to 70% in 5 min) in triethylammonium acetate buffer (0.1 M, pH 7.0) at a flow of 1 mL/min. The product 2 eluted with a retention time of 17.5 min (UV detection at 254 nm and 280 nm). The crude product was purified by preparative reverse-phase HPLC (Prontosil-ODS, 5 μm, 120 Å, 250×8 mm, Bischoff, Leonberg, Germany). Compounds were eluted with acetonitrile (7% for 5 min, followed by linear gradients to 28% in 5 min, to 42% in 15 min and to 70% in 5 min) in triethyl-ammonium hydrogencarbonate buffer (0.01 M, pH 8.6) at a flow of 3 mL/min. Fractions containing product 2 (retention time 16.0 min, UV detection at 280 nm and 300 nm) were combined and the solvent was removed by lyophilization. The aziridine cofactor 2 (1.0 mg, 26%) was obtained as a white solid.

ESI-MS: m/z (relative intensity): 571.5 (100) [M+H]$^+$.

Example 5

Synthesis of Aziridine Cofactor 3

The synthesis of cofactor 3 was carried out as shown in scheme 4. Details of the synthesis are given below.

Scheme 4: Synthesis of aziridine cofactor 3.

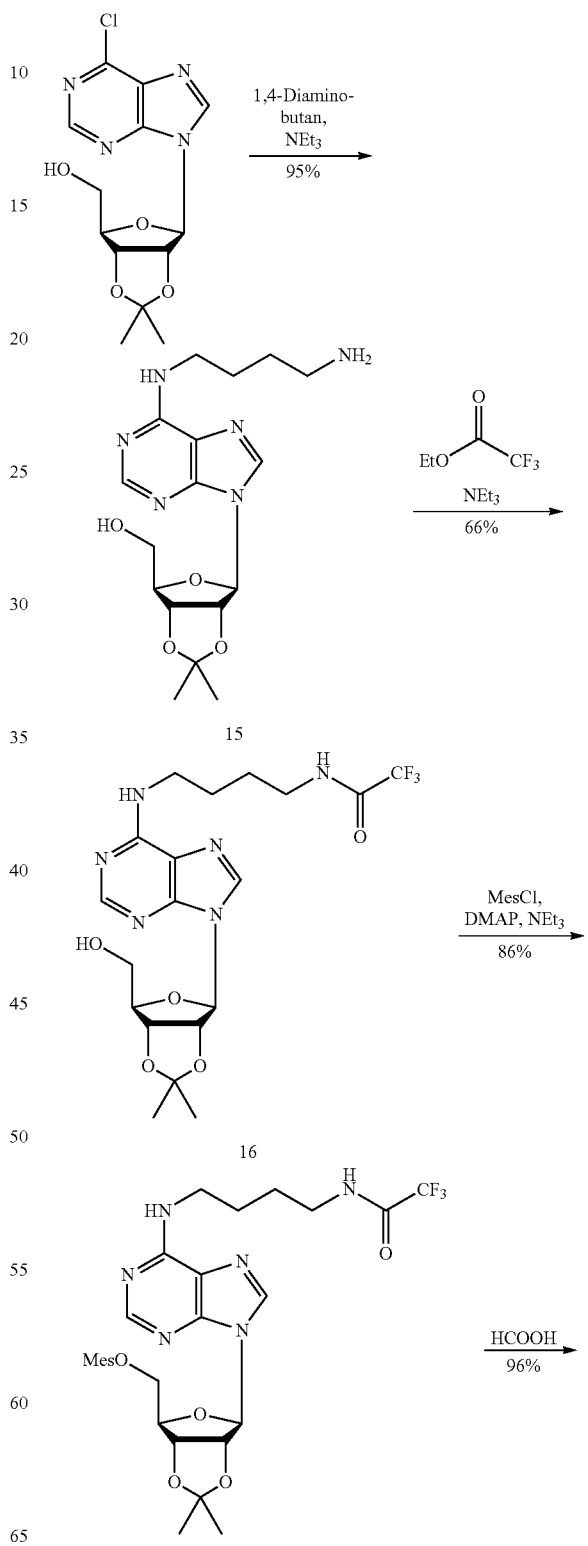

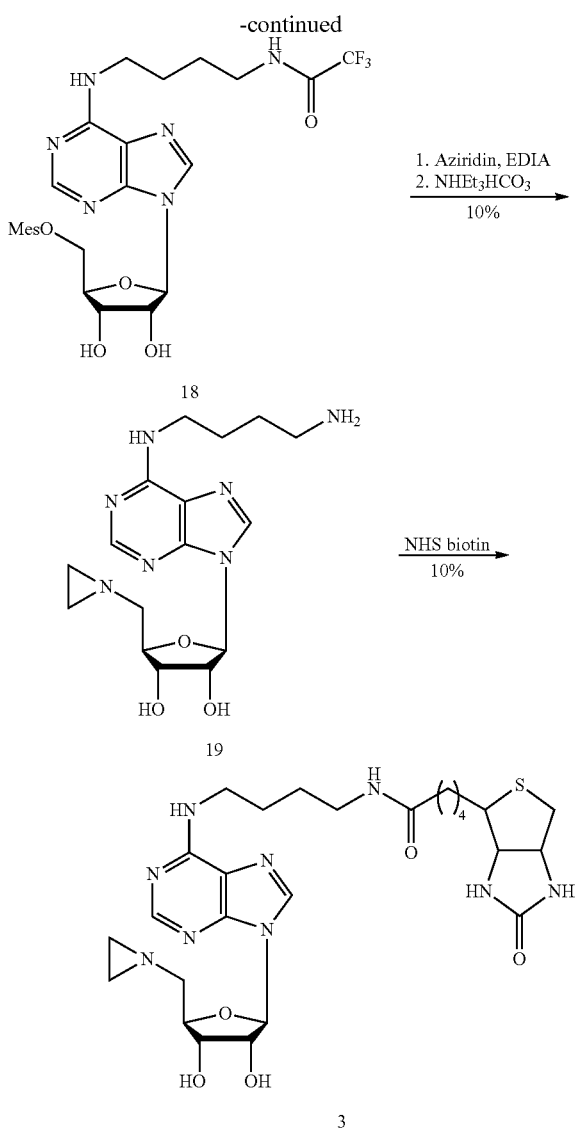

A. N64-[1"-(4"-aminobutyl)]-2',3'-O-isopropylidene-adenosine, compound 15

To a solution of 1,4-diaminobutane (1.05 g, 11.9 mmol) and triethylamine (1.70 mL, 6.92 mmol) in ethanol (5 mL) was added slowly a solution of 6-chloro-2',3'-O-iso-propylideneadenosine (Kappler and Hampton, (1990) J. Med. Chem. 33, 2545-2551) (0.97 g, 2.97 mmol) in ethanol (50 mL) and the reaction mixture was stirred at 60° C. for 18 h. The solvent and excess of reagents were removed under reduced pressure to give the crude nucleoside 15 (1.07 g, 95%) as a white solid.

$^1$H-NMR (300 MHz, [D$_6$]DMSO): δ=1.33 (s, 3H, isopropylidene-CH$_3$a), 1.56 (s, 3H, isopropylidene-CH$_3$b), 1.58-1.70 (m, 4H, H2", H3"), 2.55-2.62 (m, 2H, H4"), 3.46-3.54 (m, 2H, H1"), 3.54-3.60 (m, 2H, H5'), 4.22-4.26 (m, 1H, H4'), 4.98 (dd, $^3$J=2.48 Hz, $^3$J=6.19 Hz, 1H, H3'), 5.34 (dd, $^3$J=2.97 Hz, $^3$J=6.18 Hz, 1H, H2'), 6.13 (d, $^3$J=2.97 Hz, 1H, H1'), 8.00 (s, br, 1H, 6-NH), 8.23 (s, 1H, H8), 8.37 (s, 1H, H2).

B. N6-[1"-(4"-trifluoroacetamido)butyl]-2',3'-O-isopropylideneadenosine, compound 16

To a solution of nucleoside 15 (1.05 g, 2.77 mmol) and triethylamine (0.96 mL, 6.92 mmol) in methanol (50 mL) was added trifluoroacetic acid ethylester (1.9 mL, 16.6 mmol). The reaction mixture was stirred at room temperature overnight. The solvent was removed under reduced pressure and the crude product was purified by column chromatography (silica gel, ethyl acetate) to give nucleoside 16 (0.87 g, 66%) as a white solid (R$_f$ 0.20, ethyl acetate).

$^1$H-NMR (300 MHz, [D$_6$]DMSO): δ=1.33 (s, 3H, isopropylidene-CH$_3$a), 1.55 (s, 3H, isopropylidene-CH$_3$b), 1.57-1.61 (m, 4H, H2", H3"), 3.18-3.24 (m, 2H, H4"), 3.43-3.62 (m, 4H, H5', H1"), 4.20-4.24 (m, 1H, H4'), 4.97 (dd, $^3$J=2.47 Hz, $^3$J=6.18 Hz, 1H, H3'), 5.24 (t, $^3$J=5.57 Hz, 1H, 5'-OH), 5.34 (dd, $^3$J=2.97 Hz, $^3$J=6.19 Hz, 1H, H2'), 6.13 (d, $^3$J=2.97 Hz, 1H, H1'), 7.92, (s, br, 1H, 6-NH), 8.23 (s, 1H, H8), 8.34 (s, 1H, H2), 9.41 (t, $^3$J=5.44 Hz, 1H, 4"—NH); $^{19}$F-NMR (282 MHz, [D$_6$]DMSO): δ=−74.353; ESI-MS: m/z (relative intensity): 475.7 (100) [M+H]$^+$, 303.7 (27) [N6-[1"-(4"-trifluoroacetamido)butyl]adenine+H]$^+$.

C. N6-[1"-(4"-trifluoroacetamido)butyl]-2',3'-O-isopropylidene-5'-O-mesyl-adenosine, compound 17

To a solution of nucleoside 16 (0.85 g, 1.79 mmol) in dry methylene chloride (60 mL) under argon atmosphere were added dimethylaminopyridine (DMAP) (0.22 g, 1.79 mmol) and triethylamine (6.24 mL, 44.4 mmol) and the solution was cooled to 0° C. in an ice bath. Methanesulfonyl chloride (1.39 mL, 17.9 mmol) was slowly added and the reaction mixture was stirred at 0° C. for 2 h. The reaction was quenched by adding an ice-cold, saturated sodium hydrogencarbonate solution (15 mL) and the organic layer was removed. The aqueous layer was extracted with ice-cold chloroform (3×25 mL) and the combined organic layers were dried over magnesium sulfate. After filtration the solvent was removed under reduced pressure and the crude product was purified by column chromatography (silica gel, methanol/methylene chloride 5:95) to give nucleoside 17 (0.85 mg, 86%) as a light yellow solid (R$_f$ 0.21, methanol/methylene chloride 5:95).

$^1$H-NMR (300 MHz, [D$_6$]DMSO): δ=1.34 (s, 3H, isopropylidene-CH$_3$a), 1.56 (s, 3H, isopropylidene-CH$_3$b), 1.56-1.64 (m, 4H, H2", H3"), 3.11 (s, 3H, mesyl-CH$_3$), 3.16-3.23 (m, 2H, H4"), 3.25-3.36 (m, 2H, H1"), 4.36-4.50 (m, 3H, H5', H4'), 5.07-5.11 (m, 1H, H3'), 5.45 (dd, $^3$J=2.23 Hz, $^3$J=6.43 Hz, 1H, H2'), 6.25 (d, $^3$J=2.23 Hz, 1H, H1'), 7.90 (s, br, 6-NH), 8.24 (s, 1H, H8), 8.31 (s, 1H, H2), 9.45 (t, $^3$J=4.70 Hz, 1H, 4"—NH); $^{19}$F-NMR (282 MHz, [D$_6$]DMSO): δ=−74.35; ESI-MS: m/z (relative intensity): 591.1 (10) [M+K]$^+$, 575.1 (15) [M+Na]$^+$, 553.3 (17) [M+H]$^+$, 457.5 (100) [cyclonucleoside].

D. N6-[1"-(4"-trifluoroacetamido)butyl]-5'-O-mesyladenosine, compound 18

Nucleoside 17 (500 mg, 0.905 mmol) was dissolved in aqueous formic acid (50%, 35 mL) and the reaction mixture was stirred at room temperature for 3 d. The solvents were removed under reduced pressure and remaining solvent coevaporated with water/methanol (1:1, 3×10 mL). After drying in high vacuum nucleoside 18 (447 mg, 96%) was obtained as a white solid (R$_y$ 0.17, methanol/methylene chloride 5:95)

$^1$H-NMR (400 MHz, [D$_6$]DMSO): δ=1.66-1.86 (m, 4H, H2", H3"), 3.16 (s, 3H, mesyl-CH$_3$), 3.18-3.24 (m, 2H, H4"), 3.25-3.39 (m, 2H, H1"), 4.13-4.18 (m, 1H, H4'), 4.23-4.28 (m, 1H, H3'), 4.40-4.55 (m, 2H, H5'), 4.64-4.69 (m, 1H, H2'), 5.48 (s, br, 1H, OH), 5.63 (s, br, 1H, OH), 5.95 (d, $^3$J=5.50 Hz, 1H, H1'), 7.90 (s, br, 1H, 6-NH), 8.22 (s, 1H, H8), 8.32 (s, 1H, H2), 9.41 (t, $^3$J=5.50 Hz, 1H, 4"—NH); $^{19}$F-NMR (376 MHz, [D$_6$]DMSO): δ=−78.01; ESI-MS: m/z (relative intensity): 535.2 (5) [M+Na], 513.3 (100) [M+H]$^+$, 417.7 (9) [cyclonucleoside].

E. 5'-N-Aziridinyl-N6-[1"-(4"-aminobutyl)]-5'-deoxyadenosine, compound 19

Nucleoside 18 (150 mg, 0.292 mmol) was dissolved in a mixture of dry aziridine (1.1 mL, 17.9 mmol) (Gabriel, (1888) Chem. Ber. 21, 2664-2669; Gabriel and Stelzner, (1895) Chem. Ber. 28, 2929-2938) and N-ethyldiisopropylamine (EDIA) (3 mL, 18 mmol) under argon atmosphere and stirred at room temperature for 3 d. The reaction progress was monitored by analytical reverse-phase HPLC (Prontosil-ODS, 5 μm, 120 Å. 250×4.6 mm, Bischoff, Leonberg, Germany). Compounds were eluted with acetonitrile (14% for 5 min, followed by linear gradients to 31.5% in 10 min, to 35% in 10 min and to 70% in 5 min) in triethylammonium acetate buffer (0.1 M, pH 7.0) at a flow of 1 mL/min. The product 19 eluted with a retention time of 4.4 min (UV detection at 280 nm and 300 nm). Volatile compounds were removed under reduced pressure and the crude product was dissolved in triethylammonium hydrogencarbonate buffer (0.01 M, pH 8.6, 2 mL) before purification by preparative reverse-phase HPLC (Prontosil-ODS, 5 μm, 120 Å, 250×8 mm, Bischoff, Leonberg, Germany). Compounds were eluted with acetonitrile (7% for 5 min, followed by linear gradients to 21% in 15 min and to 70% in 5 min) in triethylammonium hydrogencarbonate buffer (0.01 M, pH 8.6) at a flow of 3 mL/min. Fractions containing product 19 (retention time 17.4 min, UV detection at 280 nm and 300 nm) were stored at −80° C. The amount of product 19 (10.1 mg, 10%) in the combined fractions (30 mL) was determined by UV spectroscopy using the published extinction coefficient $\epsilon^{267}=16000$ L mol$^{-1}$ cm$^{-1}$ of N6-[1"-(4"-aminobutyl]-2',3'-O-methoxy-ethylideneadenosine (Murata et al., (1980) J. Med. Chem. 23, 781-786).

ESI-MS: m/z (relative intensity): 364.3 (11) [M+H]$^+$.

F. 5'-N-Aziridinyl-N6-[1"-(N"-biotinyl)-4"-aminobutyl]-5'-deoxyadenosine, compound 3

To a solution (30 mL) of nucleoside 19 (10.1 mg, 27.8 μmol) in triethylammonium hydrogencarbonate buffer (0.01 M, pH 8.6) containing acetonitrile was added N-hydroxysuccinimidyl biotin (NHS biotin) (12.2 mg, 36 μmol) in dimethylsulfoxide (2 mL). The reaction mixture was stirred at room temperature for 40 min. The reaction progress was monitored by analytical reverse-phase HPLC (Prontosil-ODS, 5 μm, 120 Å, 250×4.6 mm, Bischoff, Leonberg, Germany). Compounds were eluted with acetonitrile (14% for 5 min, followed by linear gradients to 31.5% in 10 min, to 35% in 10 min and to 70% in 5 min) in triethylammonium acetate buffer (0.1 M, pH 7.0) at a flow of 1 mL/min. The product 19 eluted with a retention time of 19.1 min (UV detection at 280 nm and 300 nm). The crude product was purified by preparative reverse-phase HPLC (Prontosil-ODS, 5 μm, 120 Å, 250×8 mm, Bischoff, Leonberg, Germany) and compounds were eluted with acetonitrile (14% for 5 min, followed by linear gradients to 31.5% in 5 min, to 35% in 10 min and to 70% in 5 min) in triethylammonium hydrogencarbonate buffer (0.01 M, pH 8.6) at a flow of 3 mL/min. Fractions containing the product 3 (retention time 14.3 min, UV detection at 280 nm and 300 nm) were combined and dried by lyophilization. The aziridine cofactor 3 (3.0 mg, 18%) was obtained as a white solid.

$^1$H-NMR (400 MHz, [D$_6$]DMSO): δ=1.18-1.25 (m, 2H, aliphatic H), 1.32-1.36 (m, 2H, aliphatic H), 1.36-1.45 (m, 8H, 4×aliphatic H, 4×aziridine-H), 1.48-1.55 (m, 4H, aliphatic H), 1.97 (t, $^3$J=7.42 Hz, 2H, aliphatic H), 2.60-2.72 (m, 2H, biotin-SCH$_2$), 2.84-2.99 (m, 2H, H5'), 2.99-3.05 (m, 1H, biotin-SCH), 3.18-3.22 (m, 2H, aliphatic-H), 3.80-3.91 (m, 1H, H4'), 4.02-4.10 (m, 1H, biotin-SCHRCH), 4.15-4.19 (m, 1H, H3'), 4.20-4.23 (m, 1H, biotin-SCH$_2$CH), 4.56-4.60 (m, 1H, H2'), 5.20 (s, br, 1H, OH), 5.40 (s, br, 1H, OH), 5.79-5.83 (m, 1H, H1'), 6.30 (s, br, 1H, biotin-NHa), 6.39 (s, br, 1H, biotin-NHb), 7.70 (t, $^3$J=5.49 Hz, 1H, 4"—NH), 7.75 (m, 1H, 6-NH), 8.10 (s, 1H, H8), 8.22 (s, 1H, H2); ESI-MS: m/z (relative intensity): 612.6 (53) [M+Na]$^+$590.5 (100) [M+H]$^+$, 433.6 (12) N6-[1"-(N"-biotinyl)-4"-aminobutyl]-adenine+H]$^+$.

Example 6

Road Block Modification of DNA

A. The Concept

The following experimental approach is based on the idea that sterically demanding modifications of nucleic acid molecules can lead to a reduction or blockage of amplification of said nucleic acid molecule. The modification is introduced at specific recognition sequences for DNA-methyltransferases. A pre-requisite for the modification is the presence of non-methylated recognition sequences since methylation at these sides prevents any further modification with the sterically demanding aziridin-cofactors. Following therefrom, only unmethylated DNA strands are prevented from amplification (by the presence of the sterically demanding aziridin derivative), whereas methylated DNA strands (which can not be modified with the aziridin derivative) can be amplified in a subsequent PCR reaction. This concept is summarized in the following scheme (scheme 1).

Scheme 5: "road block" concept for determining the methylation pattern of DNA. Left: non-methylated DNA-MTase recognition sequences (grey bars) are sequence-specifically modified by using a DNA-MTase and an aziridine-cofactor, so that DNA amplification (e.g. in a subsequent PCR reaction) is hindered or blocked. Right: methylated DNA-Mtase recognition sequences cannot be modified by the aziridine-cofactor, so that the corresponding DNA can be amplified (e.g. in a subsequent PCR reaction).

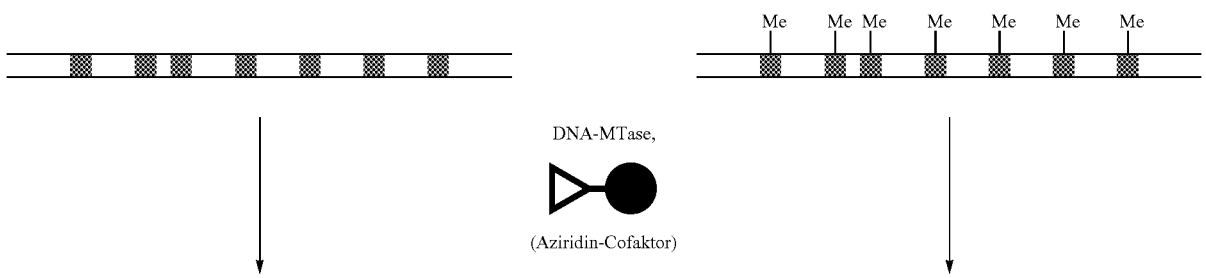

45

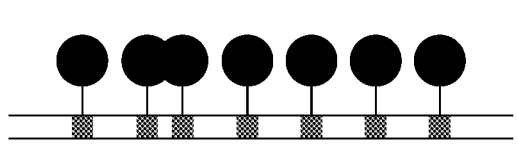

no PCR product

-continued

46

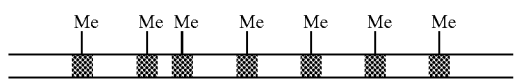

DNA-Polymerase,
Pimer, dNTPs

PCR product

Test DNA was modified by use of DNA-MTase from *Haemophilus haemolyticus* (M.HhaI). M. HhaI catalyzes the transfer of activated methyl groups from the natural cofactor S-adenosyl-L-methionin (AdoMet) onto the 5-position of the first cytosine-residue within the double stranded sequence 5'GCGC-3' (scheme 6) and can thereby modify 5'-GCGC-3'-sequences of the test DNA.

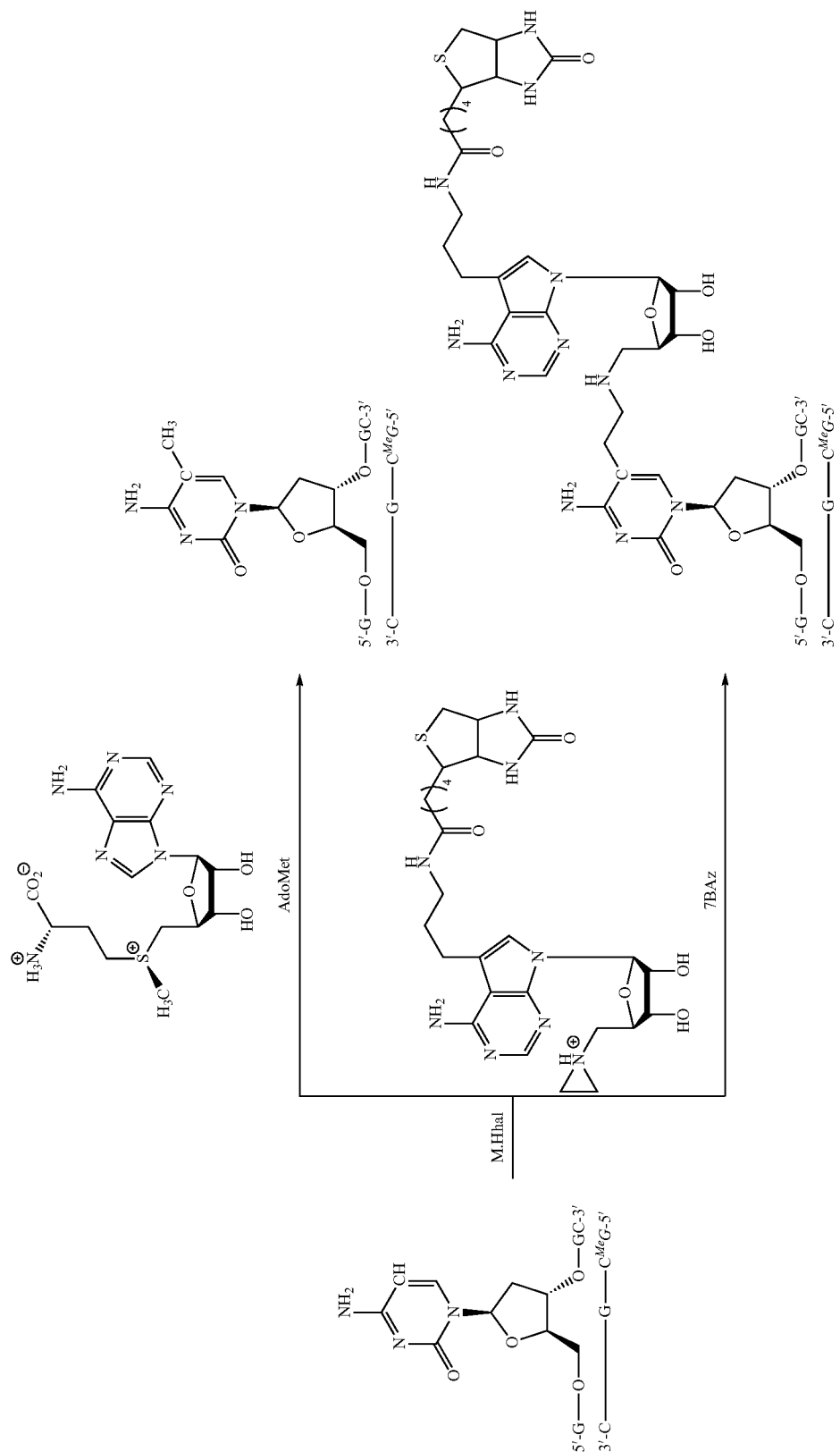
Scheme 6: M.HhaI catalysed reactions.

In addition, the enzyme is rather useful for sequence-specific methyltransferase-induced labelling of DNA (SMILing DNA). Furthermore, MQ1 (M.SssI) was analysed with respect to its usefulness within the SMILing DNA-technology. M.SssI is the only known bacterial cytosine-specific DNA-MTase with a 5'-GCGC-3' recognition sequence and could, potentially, be used for analyzing the methylation status of CpG-motives of (human) DNA.

Scheme 7: M.SssI catalysed reactions.

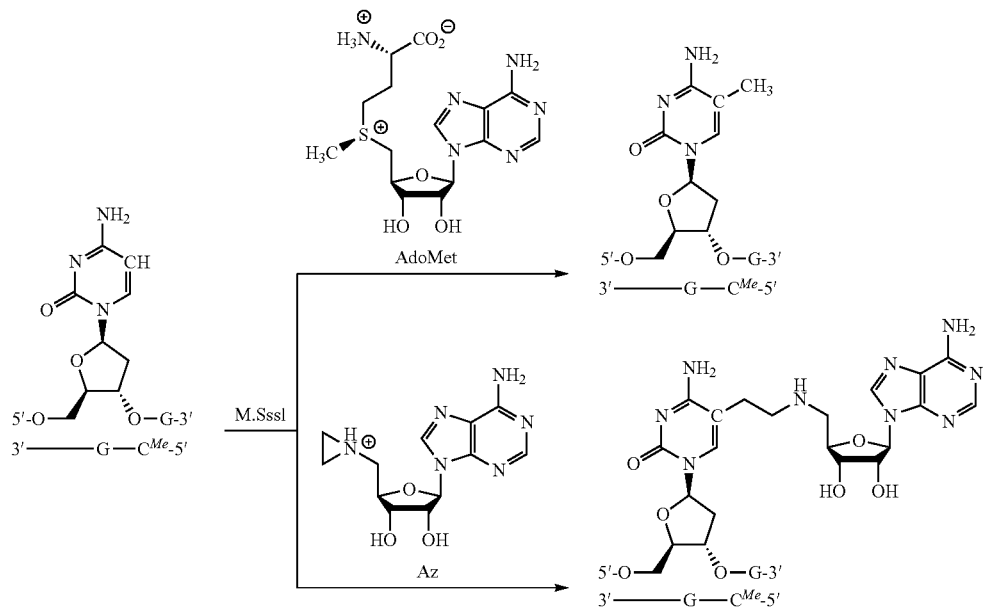

M.SssI has a high enzymatic activity and could be produced by expression in *Escherichia coli*. Moreover, experiments have shown that M.SssI is capable of using the simple aziridin-cofactor Az to modify DNA-molecules (scheme 7).

B. Sequence-Specific Labelling of DNA by Using M. HhaI and 7BAz

Figure 3:
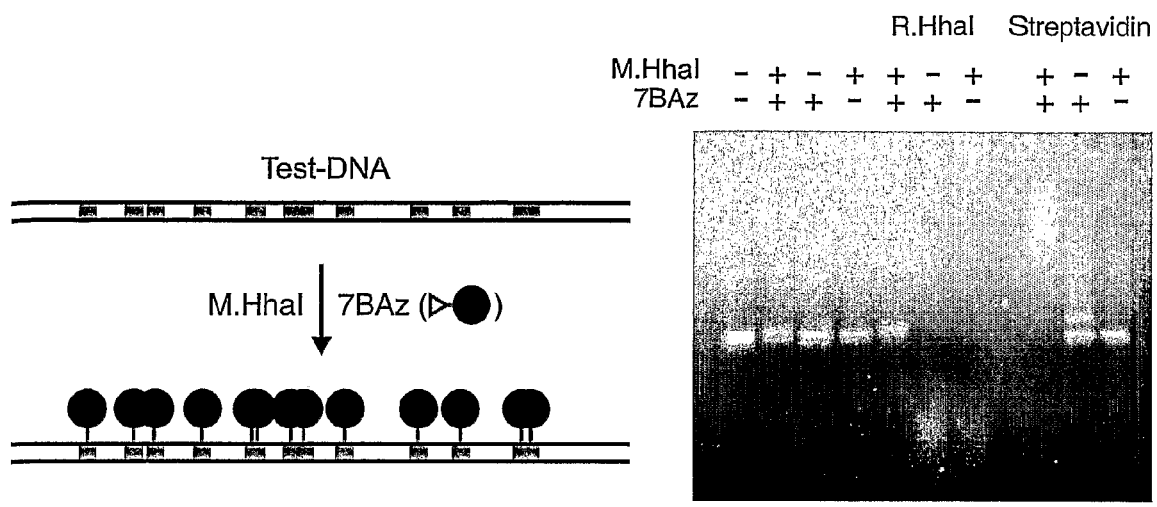
FIG. 3: Sequence specific labelling of Test-DNA using M.HhaI and 7BAz. Left: reaction scheme. Right: Test of the labelling reaction by addition of R.HhaI resp. Streptavidin, subsequent electrophoresis on an agarose gel.

A 320 base pair along test DNA was prepared as described herein. This test DNA contains 13 5'-GCGC-3' recognition sequences for M.HhaI, two of which overlap (FIG. 3, left).

Figure 4:
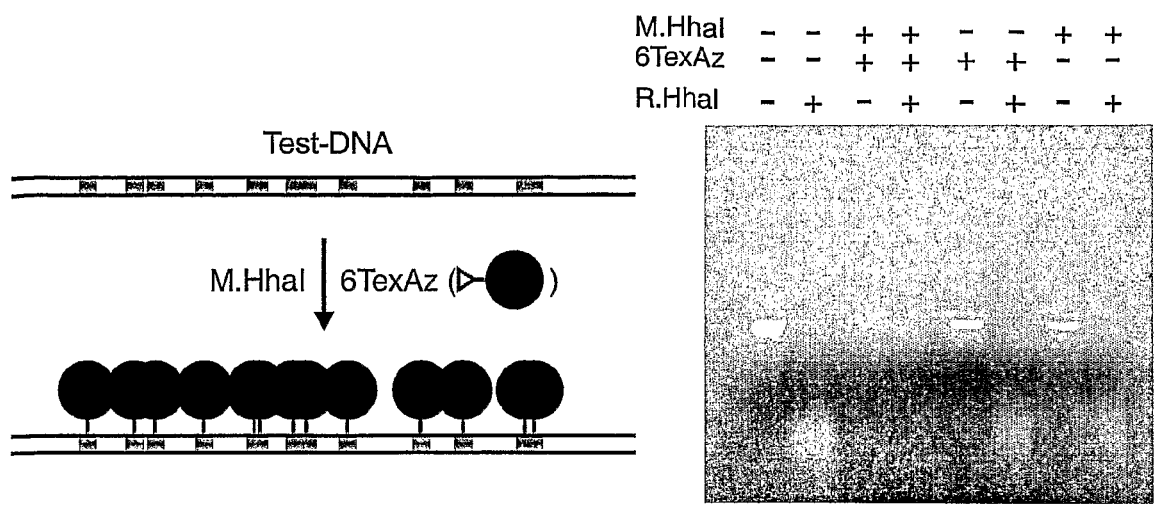
FIG. 4: Sequence specific labelling of test DNA using M.HhaI and 6TexAz. Left: reaction scheme. Right: Test of the labelling reaction by addition of R.HhaI, subsequent electrophoresis on an agarose gel.

Test DNA, M.HhaI and 7BAz were incubated for 3 h in buffer at 37° C. for 3 h. Subsequently, the enzyme by heat-inactivated and the modified DNA was purified by a commercially available kit. At the same time control-reactions (without M.HhaI or without 7BAz) were carried out and DNA samples were analysed by "real-time" PCR. on modified Modification was tested by using restriction endonuclease R.HhaI which can not cut at modified recognition sequences. After incubating the test DNA with M.HhaI and 7BAz, the DNA was completely protected against R.HhaI activity (FIG. 3, right). The two controls without M.HhaI and/or 7BAz were completely digested (i.e. cut). The presence of biotin residues DNA was also analysed by using an electrophoretic mobility-shift-assay. Addition of streptavidin had a pronounced effect on the electrophoretic mobility of modified DNA (FIG. 4, right). On the other hand, controls without M.HhaI or 7BAz essentially showed no difference in the mobility of DNA in this assay.

C. Sequence-Specific Labelling of DNA by Using M.HhaI and 6TexAz

N-adenosylaziridine-cofactor 7BAz has a molecular weight of 534 g/mol. In order to test the properties of a sterically more demanding Cofactor, N-adenosylaziridine-derivative 6TexAz, having a molecular weight of 1065 g/mol, was synthesized (scheme 8).

Scheme 8: Synthesis of the sterically demanding N-adenosylaziridine-cofactor 6TexAz (cofactor 4).

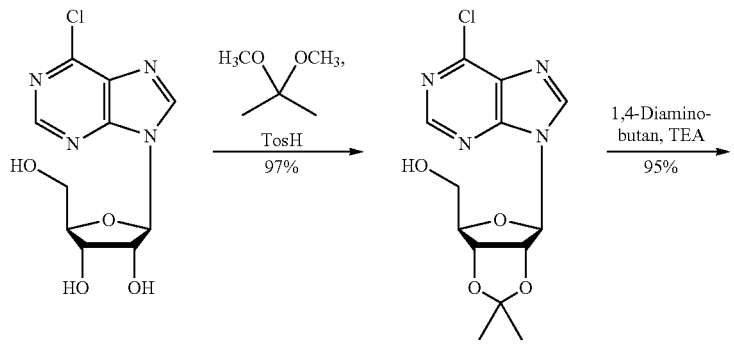

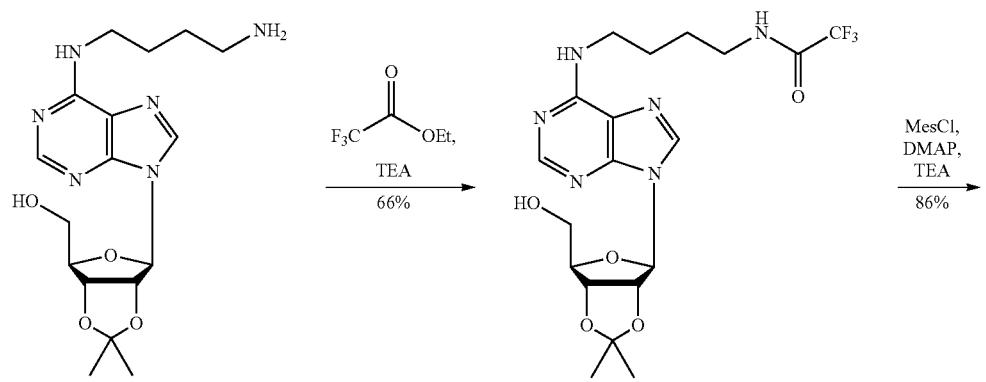
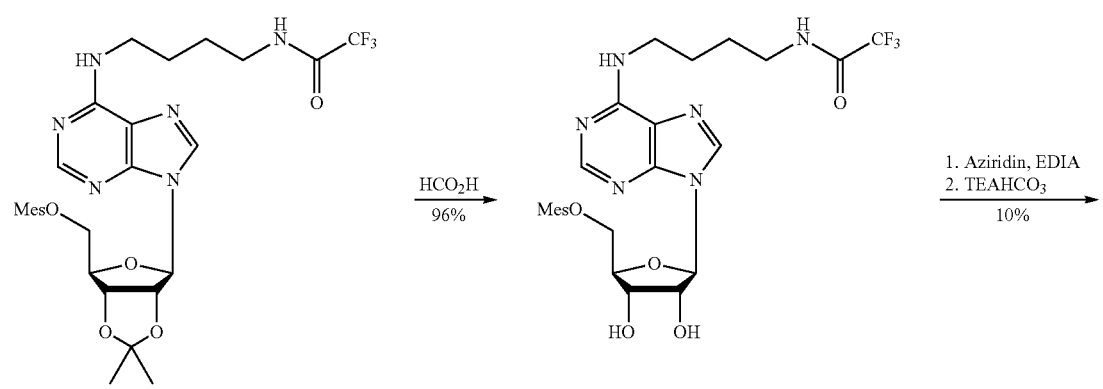
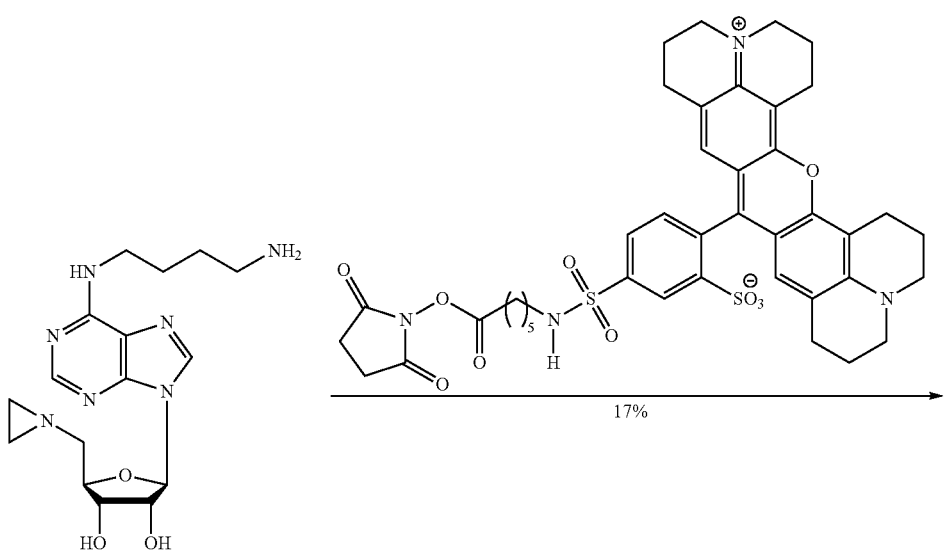

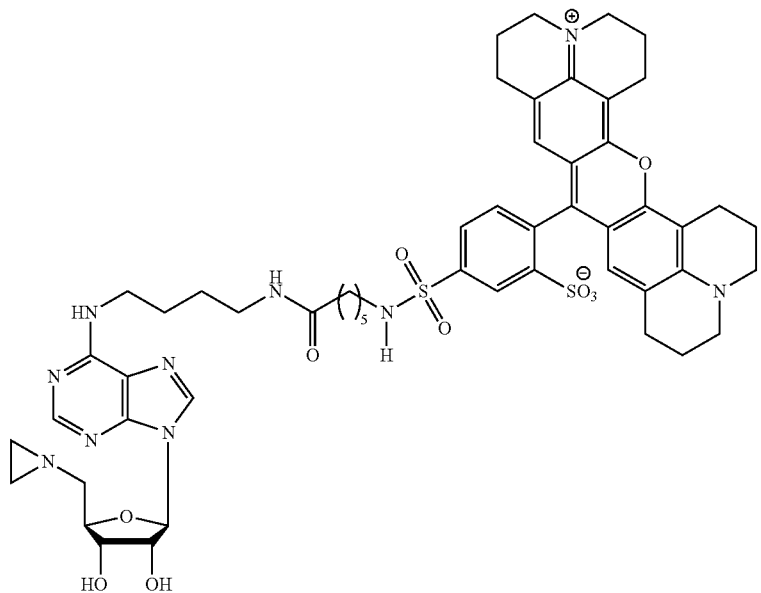

6TexAz

Synthesis was based on 6BAz. Starting from 6-chloropurin-9-β-D-ribufuranosid, the secondary hydroxyl groups were protected as acetonid, a diaminobutan-linker was introduced in 6-position and the primary amino function of the linkers were protected as trifluoracetamid. Subsequently the 5'-hydroxyl group was activated as mesylate, the isopropyliden protection group was removed and the aziridine group was introduced by nucleophilic substitution at the 5'-position. Alkaline conditions during the preparation result in a deprotection of the primary amino function of the linkers so that these are available for the final reaction with an NHS-Ester of TexAz Red.

For sequence-specific DNA labelling (FIG. 4, left), test DNA was incubated with M.HhaI and 6TexAz in buffer at 37° C. for 15 h.

Subsequently, the enzyme was heat inactivated and modified DNA was purified by a commercially available kit. In addition, parallel controls were performed in the absence of M.HhaI or in the absence of 6TexAz. 3 DNA samples were analysed in a "real-time" PCR experiment.

For checking the labelling reaction, 3 samples were treated with R.HhaI. After incubation of test DNA with M.HhaI and 6TexAz, the test DNA was completely protected against digestion with R.HhaI (FIG. 4, right). On the other hand, both control samples without M.HhaI or 6TexAz showed complete digestion.

D. N-Adenosylaziridine Derivative 6BAz as Cofactor for M.SssI

For analyzing the DNA methylation status of human DNA, DNA-MTase M.SssI might be particularly useful since, in comparison with M.HhI, it cannot modify each and every methylated CpG-motive. Therefore, it was tested whether or not M.SssI is in principle useful for the SMILing DNA technology and, hence, for the "road-block" concept. It was known that M.SssI is capable of using the non-complex aziridine-cofactor Az as a substrate and can couple it to DNA (scheme 7). On the other hand, the N-adenosylaziridine-derivatives 8BAz and 7BAz, coupled with a linker in 8- or 7-position to a biotin group, cannot be transferred onto DNA molecules (scheme 9), which could be the result of unfavorable steric hindrance with the cofactor binding pocket of M.SssI.

Scheme 9: N-adenosylaziridine-derivatives as cofactors for M.SssI.
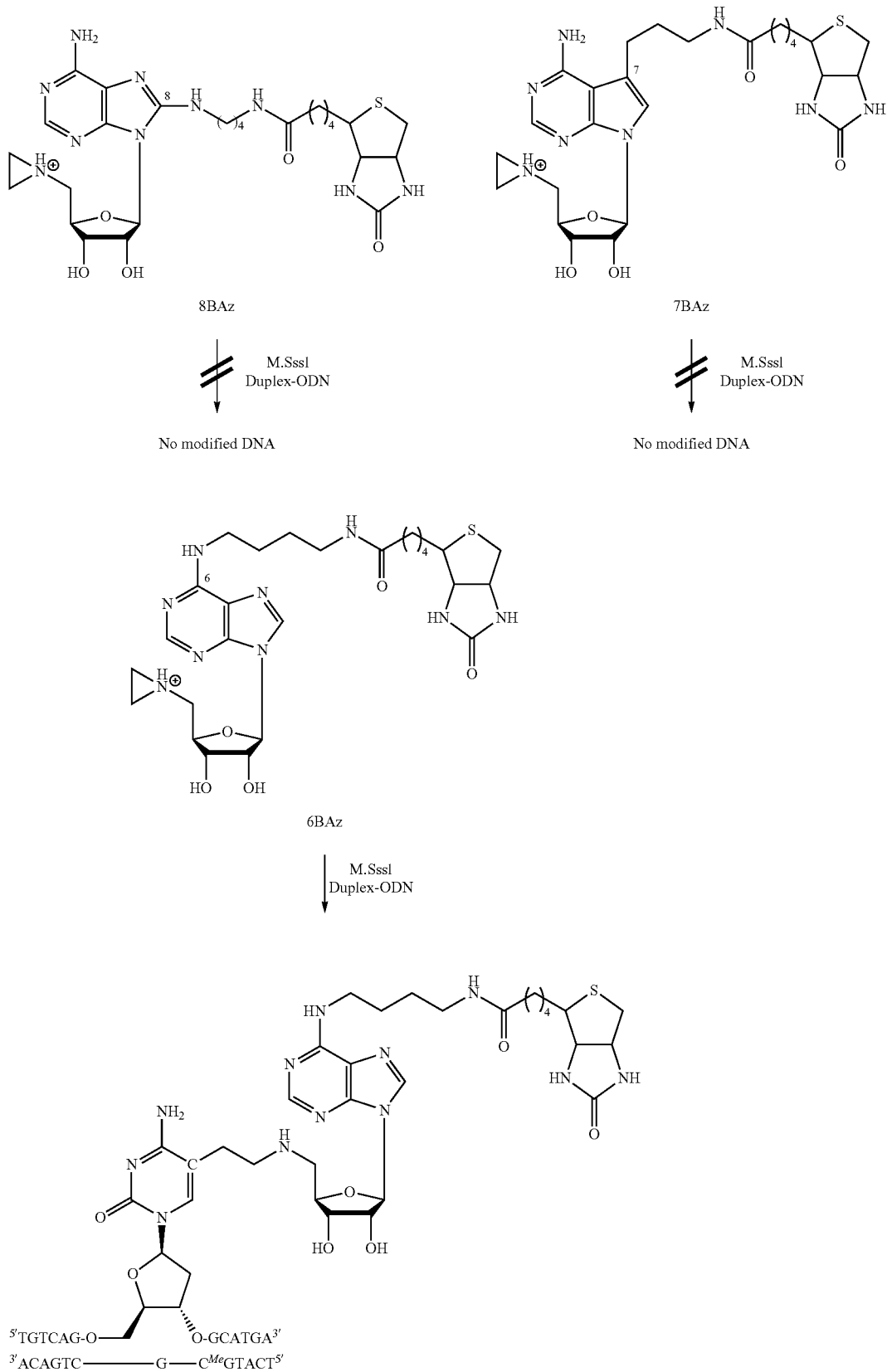

M.SssI-mediated conversion of 6BAz was studied by using a duplex-oligodeoxynucleotide and purified DNA-methyltransferase. After adjusting and optimizing the reaction conditions (pH and composition of the puffers, temperature, amount of M.SssI) 60% of a hemi-methylated duplex-oligodeoxynucleotide was labelled in a 2 h reaction. When unmethylated duplex-oligodeoxynucleotides were used, approximately 100% was labelled. These diverging results may be due to the presence of minor amounts of natural cofactor AdoMet in the enzyme preparation.

In summary, sequence-specific labelling of test DNA with DNA-MTase M.HhaI showed quantitative conversion with aziridine-cofactor 6TexAz and 7BAz. Labelled DNA samples and control DNA samples were tested in "real-time" PCR reactions. In comparison with both controls. The amplification reaction was markedly impaired in comparison with both controls. The amplification impairment was even more pronounced when 6TexAz-labelled test DNA was used as PCR template. These results demonstrate that the "road-block" concept is useful for the detection of non-methylated recognition sequences of DNA-MTase.

In addition it was shown that 6BAz is an aziridin-cofactor for the DNA-MTase M.SssI so that a sequence-specific modification of all unmethylated CpG-motives in DNA should be possible. An effective method for the detection of DNA methylation patterns might therefore be based on a "real-time" PCR of aziridine-labelled DNA.

E. Methods

E1. Sequence-Specific Labelling of Test DNA with M.HhaI and 7BAz

Test DNA (1.2 µg, 320 bp, 13 recognition sequences for M.HhaI, 0.6 µg/M M.HhaI-recognition sequences), M.HhaI (1.2 µM) and 7BAz (80 µM) in buffer (118 µl) consisting of Tris/HCl (10 mM, pH 7.4), NaCl (50 mM), EDTA (0.05 mM) and 2-mercaptoethanol (2 mM) were incubated for 3 h at 37° C. DNA was also incubated in the absence of M.HhaI or 7BAz (control). Subsequently, the samples were heated for 20 min to 80° C. DNA was purified by using QIAquick PCR purification kit of QUIAGEN (Hilden) according to the manufacturer's protocol, DNA was eluted with buffer (40 µL, 10 mM Tris/HCl, pH 8.5).

Restriction analysis was carried out by incubating 3.3 µL of purified labelled DNA (or control) with buffer (7.7 µL, 10 mM Tris/HCl, pH 7.9, 15 mM $MgCl_2$, 75 mM NaCl and 1 mM 1,4-dithiothreitol) and R.HhaI (8 U) in buffer (9 µL) consisting of Tris/HCl (10 mM, pH 7.9), $MgCl_2$ (10 mM), NaCl (50 mM), 1,4-dithiothreitol (1 mM) and BSA (2.2 µg/µL), incubated for 3 h at 37° C. Subsequently, the samples were incubated for 20 min at 80° C., a proteinase K-solution (1 µL, 20 µg/µL in 10 mM Tris/HCl, pH 7.5, QIAGEN proteinase K) was added, followed by 30 min at 37° C. and incubation for 20 min at 80° C. Afterwards the samples were mixed with sample buffer (2 µL, 0.25% bromophenolblue and 30% glycerol) and analysed on a 1% agarose-gel.

Electrophoretic mobilityshift assay: 3.3 µL of purified labelled DNA (or control) was mixed with buffer (7.7 µL, 10 mM Tris/HCl, pH 7.9, 15 mM $MgCl_2$, 75 mM NaCl and 1 mM 1,4-dithiothreitol) and a streptavidin-solution (2 µL, 2.0 µg/µL) and incubated for 3 h at 37° C. Afterwards the samples were treated with sample buffer (2 µL, 0.25% bromophenol-blue and 30% glycerol) and analysed on a 1% agarose-gel.

E2. Synthesis of Sterically Demanding Aziridine-Cofactor 6Texaz

6TexAz was essentially synthesized as described in scheme 8. The NHS-Ester of TexasRed (2.2 µM) is solubilized in DMSO (1.2 mL), mixed with 1.35 mL of a solution of 5'-aziridinyl-N6-[1"-(4"-aminobutyl)]-5'-desoxyadenosine (1.8 µmol in 10 mM triethylammoniumhydrogencarbonate-buffer and 30% acetonitril) and stirred for 30 min at RT. After control of the reaction (HPLC-control) by preparative reversed phase HPLC (prontosil-ODS, 5 µm, 120 Å, 250×8 mm, Bischoff, Leonberg) the product was purified. The product was eluted with acetonitril (21% for 5 min, followed by a linear gradient on 70% in 5 min and 70% isocratric for 10 min) in triethylammonium-hydrogencarbonate buffer (10 mM, pH 8.5) at 3 mL/min. Factions containing the product (retention time 13.5 min, UV detection at 280 and 595 nm) were collected and lyophillysed, the red solid compound was solubilized in 100 µL of DMSO. The yield of aziridine-cofactor 6TexAz (17%) is determined UV spectroscopy ($\epsilon^{595}$=80.000 $cm^{-1}$ $M^{-1}$).

E3. Sequence-Specific Labelling of Test DNA with M.HhaI and 6TexAz

Test DNA (1.0 µg, 320 bp, 13 recognition sequences for M.HhaI, 0.6 µ/M M.HhaI-recognition sequences), M.HhaI (1.2 µM) and 6TexAz (60 µM) in buffer (100 µL) consisting of Tris/HCl (10 mM, pH 7.4), NaCl (50 mM), EDTA (0.05 mM) and 2-mercaptoethanol (2 mM) were incubated for 15 h at 37° C. As parallel controls, the test DNA was incubated in the absence of M.HhaI or 6TexAz. Subsequently, the samples were heated for 20 min to 80° C. DNA was purified by using QIAquick PCR purification kit of QUIAGEN (Hilden) according to the manufacturer's protocol, DNA was eluted with buffer (50 µL, 10 mM Tris/HCl, pH 8.5).

Restriction analysis was carried out by incubating 5.0 µL of purified labelled DNA (or control) with buffer (5.0 µL, 20 mM Tris/HCl, pH 7.9, 15 mM $MgCl_2$, 100 mM NaCl und 2 mM 1,4-dithiothreitol) and R.HhaI (8 U) in buffer (9 µL) consisting of Tris/HCl (10 mM, pH 7.9), $MgCl_2$ (10 mM), NaCl (50 mM), 1,4-dithiotreitol (1 mM) and BSA (2.2 µg/µL), incubated for 3 h at 37° C. Subsequently, the samples were incubated for 20 min at 80° C., a proteinase K-solution (1 µL, 20 µg/µL in 10 mM Tris/HCl, pH 7.5, QIAGEN proteinase K) was added, followed by 30 min at 37° C. and incubation for 20 min at 80° C. Afterwards the samples were mixed with sample buffer (2 µL, 0.25% bromophenolblue and 30% glycerol) and analysed on a 1% agarose-gel.

Figure 5:
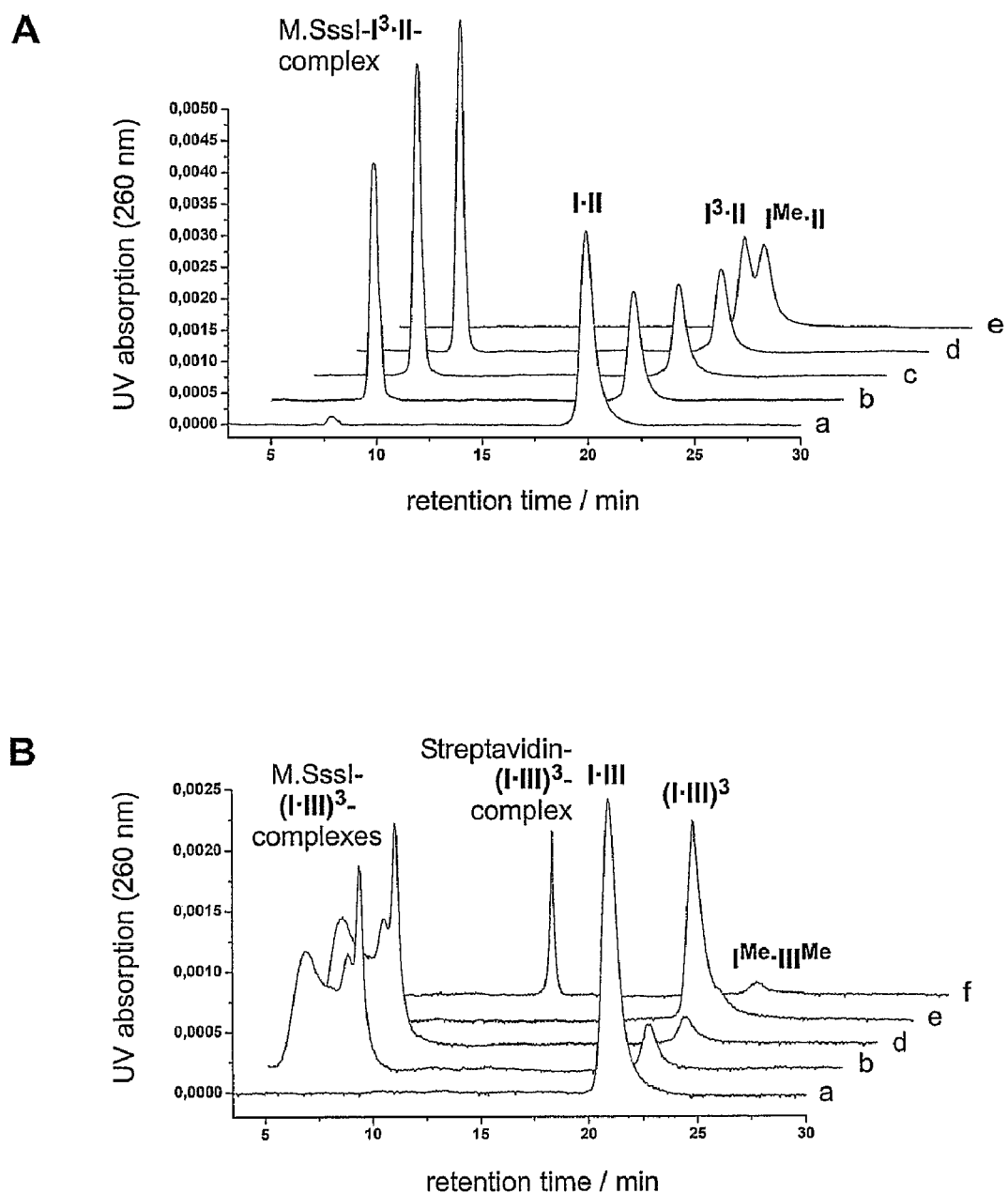
FIG. 5: M.SssI-catalysed coupling of biotinylated aziridine cofactor 3 with the hemi-methylated duplex oligodeoxynucleotide I-II (A) and the non-methylated duplex oligodeoxynucleotide I-III (B) analysed by anion exchange HPLC at the beginning of the reaction (a), after 1 h (b), after 2 h (c), after 3 h (d), after additional heating to 95° C. for 10 min (e) and further addition of streptavidin (f).

E4. M.SssI-Catalysed Coupling of Biotinylated Aziridine Cofactor 3 with the Hemi-Methylated Duplex Oligodeoxynucleotide I-II and the Non-Methylated Duplex Oligodeoxynucleotide I-III Aziridine cofactor 3 with a biotin group attached to the 6 position of the adenine ring is a substrate for M.SssI (Scheme 10). This is demonstrated in FIG. 5.

Scheme 10: M.SssI-catalysed coupling of biotinylated aziridine cofactor 3 with the hemi-methylated duplex oligodeoxynucleotide I-II (M = 5-methyl-2′-deoxycytidine).

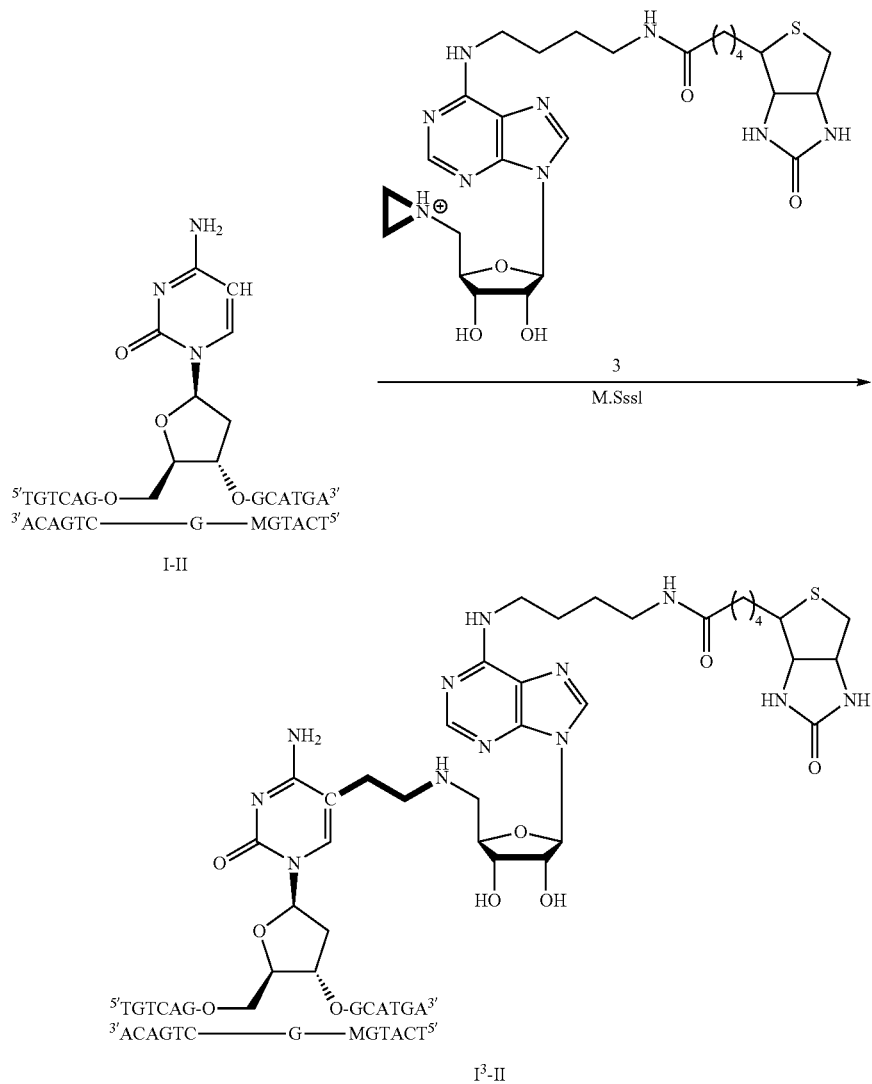

Solutions of hemi-methylated duplex oligodeoxynucleotide I-II (1 µM, I=5′-TGTCAGCGCATGA-3′ (SEQ ID NO:1), II=5′-TCATGMGCTGACA-3′ with M=5-methyl-2′-deoxycytidine (SEQ ID NO:2)) or non-methylated duplex oligodeoxynucleotide I-III (1 µM, I=5′-TGTCAGCGCATGA-3′ (SEQ ID NO:1), III=5′-TCATGCGCTGACA-3′ (SEQ ID NO:3)), aziridine cofactor 3 (100 µM) and M.SssI (2 µM) in buffer (10 mM Tris hydrochloride, pH 7.4, 50 mM sodium chloride, 10 mM ethylenediaminetetraacetic acid and 2 mM dithiothreitol) were incubated at 21° C. The progress of the coupling reactions was monitored by anion exchange HPLC (Poros 10 HQ, 10 µm, 4.6×100 mm, Applied Biosystems). Compounds were eluted with aqueous potassium chloride (0.2 M for 5 min, followed by linear gradients to 0.5 M in 5 min and to 1 M in 30 min) in Tris hydrochloride buffer (10 mM, pH 7.6) supplemented with sodium azide (1 mM) at a flow of 4 mL/min.

Directly after mixing 3 with the duplex I-II and M.SssI a new compound with a much smaller retention time (7.9 min) was observed (FIG. 5A). The amount of this reaction product increased and the amount of the starting material I-II decreased during the incubation. The reaction product is assigned to a non-covalent protein-DNA complex between M.SssI and the coupling product $I^3$-II based on the observed UV absorption ratio at 260 nm and 280 nm (not shown). The coupling product $I^3$-II was released from the protein-DNA complex by incubation at 95° C. for 10 min and a slightly smaller retention time was observed for the product duplex $I^3$-II (19.4 min) compared with the retention time of the starting material I-II (20.2 min). Conversion of starting duplex I-II to the product duplex $I^3$-II was about 60%. Addition of another equivalent of M.SssI after 3 h and incubation for 1 h at 21° C. did not lead to further product formation indicating that the reaction came to completion after 3 h (not shown). This non-complete conversion was attributed to small amounts of the natural cofactor S-adenosyl-L-methionine present in the enzyme preparation and M.SssI-catalysed methyl group transfer from S-adenosyl-L-methionine to the hemi-methylated duplex I-II leading to the double-methylated duplex $I^{me}$-II should block the reaction with aziridine cofactor 3.

This assumption was verified using the non-methylated duplex I-III as starting material for the M.SssI-catalysed coupling reaction with the aziridine cofactor 3 (FIG. 5B). With this duplex almost complete conversion to non-covalent protein-DNA complexes between M.SssI and the coupling product (I-III)$^3$ (retention times 5.3-9.6 min) occurred during 3 h incubation. Again, the coupling product (I-III)$^3$ was released from the protein-DNA complexes by incubation at 95° C. for 10 min and a slightly smaller retention time was observed for the product duplex (I-III)$^3$ compared with the retention time of the starting duplex HU. In addition, the presence and functionality of biotin groups in the product duplex (I-III)$^3$ was verified by addition of streptavidin. Excess of aziridine cofactor 3 was first removed by gel filtration using a NAP-5 column (Amersham Biosciences, Freiburg, Germany) and elution with Tris hydrochloride (10 mM, pH 7.4), sodium chloride (50 mM), ethylenediaminetetraacetic (10 mM) acid and dithiothreitol (2 mM). Afterwards, streptavidin (1 µg for 10 µmol duplex) was added and the solution incubated at room temperature for 30 min. Anion exchange HPLC analysis (see above) revealed a new major compound with a retention time of 14.2 min which is in accordance with the formation of a complex between streptavidin and the biotinylated duplex (I-III)$^3$. In addition to this complex, small amounts of presumably double-methylated duplex I$^{me}$-III$^{me}$ were observed.

Example 7

Real-Time PCR Application of the Road Block Concept

Figure 6A:
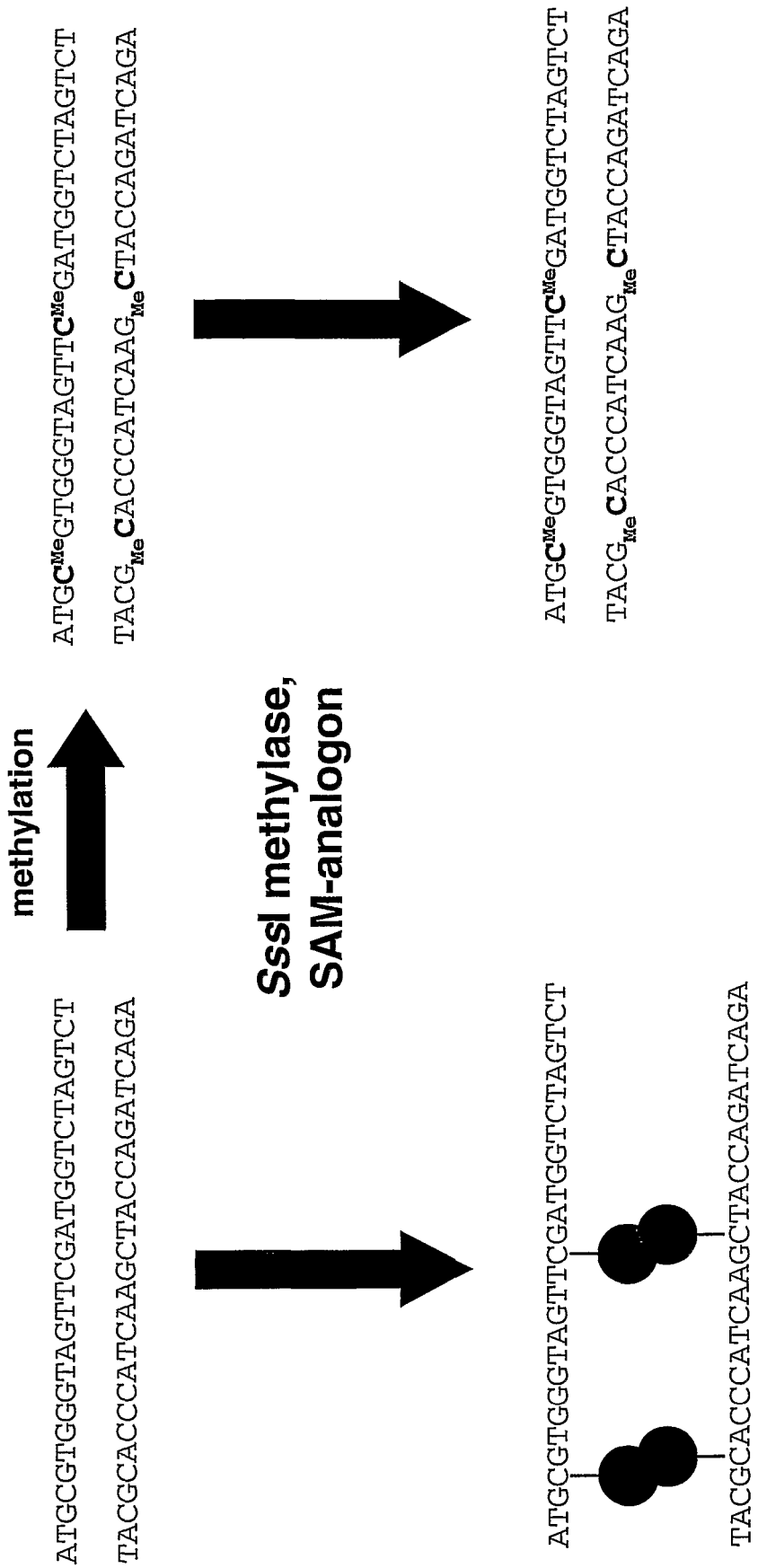
FIG. 6: (A) The principle of DNA-labelling using DNA-Methyltransferases and aziridine derivatives; (B) The principle of inhibiting PCR-amplification by aziridine-labelled DNA-templates.
Figure 6B:
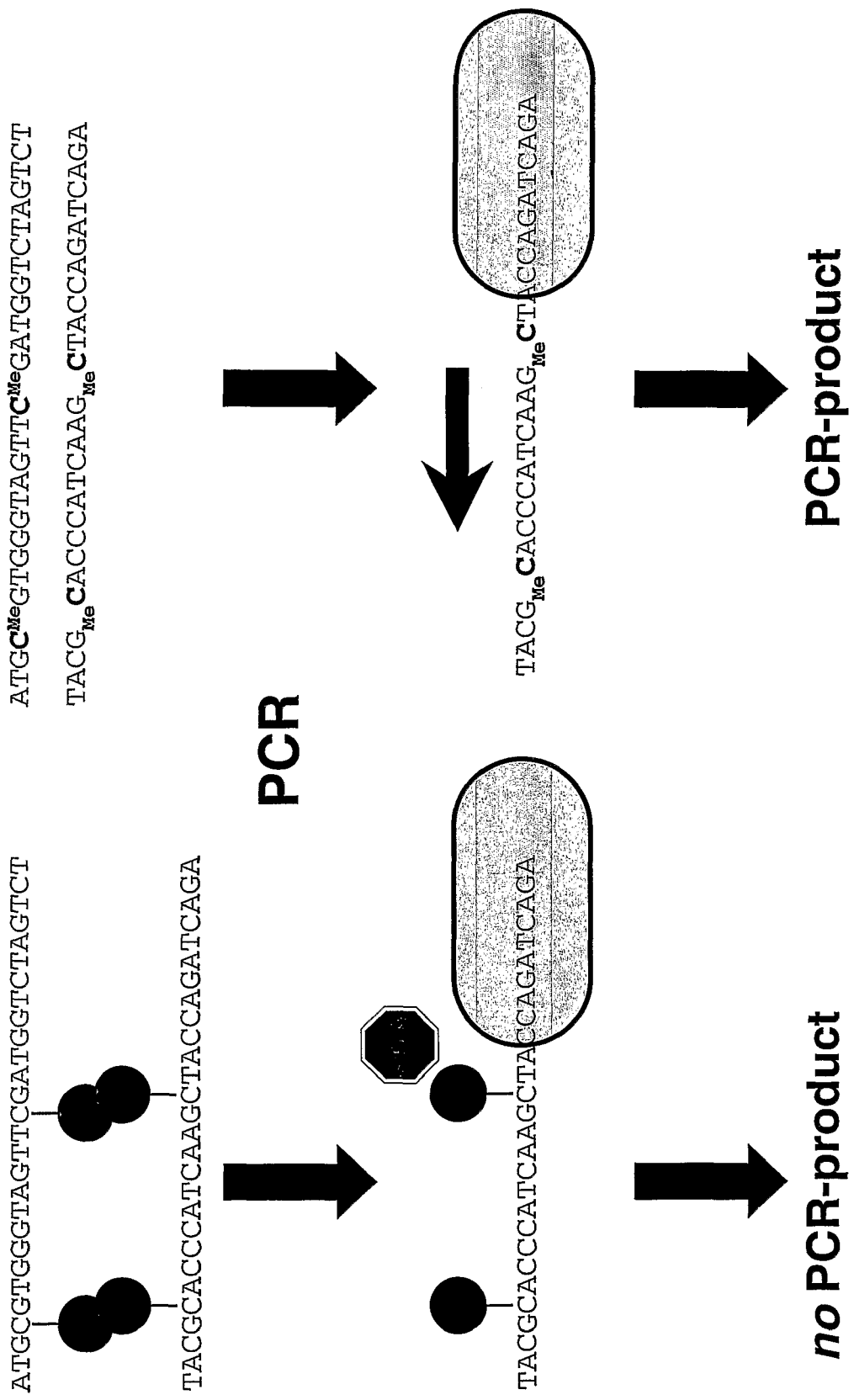

Sequence specific, covalent labelling of nucleic acid molecules can be realized by using S-Adenosyl-Methionine-Analoga such as N-Adenosylaziridine derivatives and methyltransferases. The labeling, however, is only possible at non-methylated bases of the DNA substrate, methylated bases cannot be labelled (FIG. 6A). It is conceivable that the labelling of DNA substrates with bulky Aziridine side chains has an inhibitory effect on a subsequent PCR amplification reaction (FIG. 6B). A methylated DNA substrate, however, would remain uneffect. This difference could be detected in a real time-PCR (LightCycler).

(A) PREPARATION OF THE DNA SUBSTRATE

As a "DNA model substrate", part of the promoter and Exon1 range of the human GSTP1 gene was chosen. This DNA substrate was synthesized by a so-called overlap-extension-PCR. In this method, oligonucleotides each about 100 bp in length are hybridized with an overlapping range of about 20 bp and amplified to give a double strand in a subsequent polymerase reaction (FIG. 7). Sufficient amounts of the substrate were treated in a subsequent standard PCR (fw-primer: 5'GACCTGGGAAAGAGGGAAAGGC-3' (SEQ ID NO:4); rev-primer: 5'-CTGCGGGTTGGCCCCATGC-3' (SEQ ID NO:5; denaturation: 30 sec at 96° C., annealing: 60 sec at 59° C.; amplification: 30 sec at 72° C.; 30 cycles). The synthesized DNA substrate was subsequently examined for its correctness by means of sequence analysis (FIG. 8).

(B) METHYLATION OF THE DNA SUBSTRATE

Figure 9A:
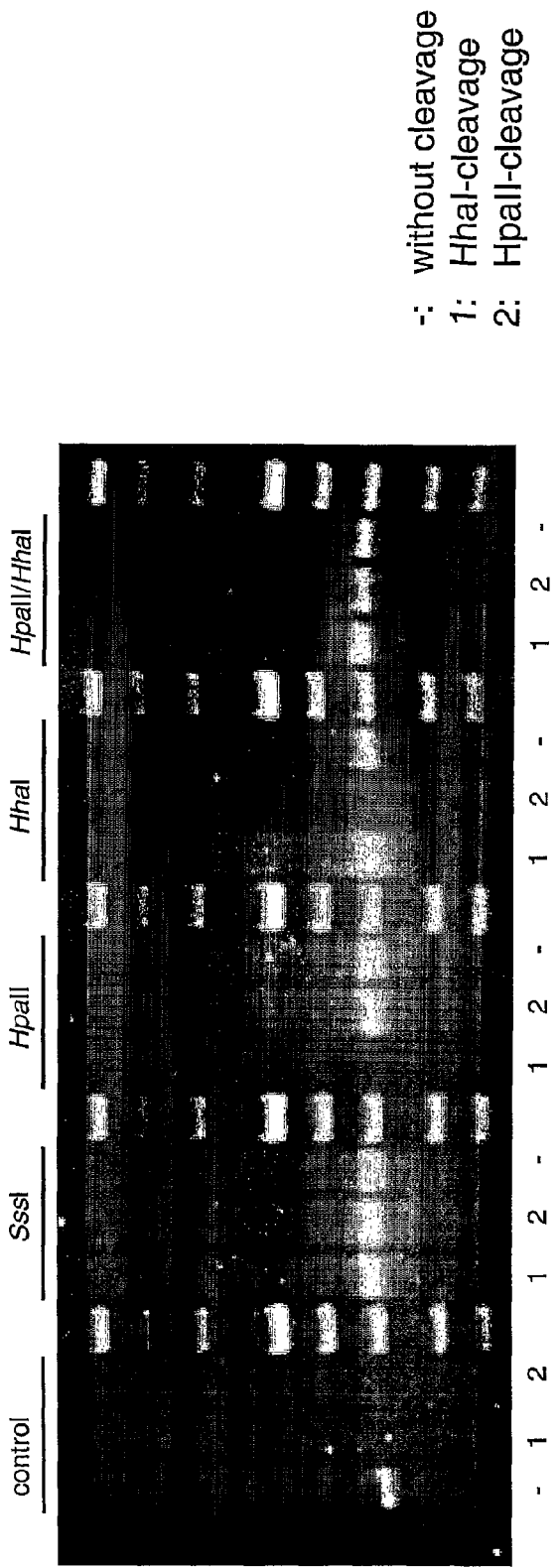
FIG. 9: (A) Production of methylated/partially methylated DNA substrate; (B) Analysis of methylated/partially methylated DNA substrate.
Figure 10A:
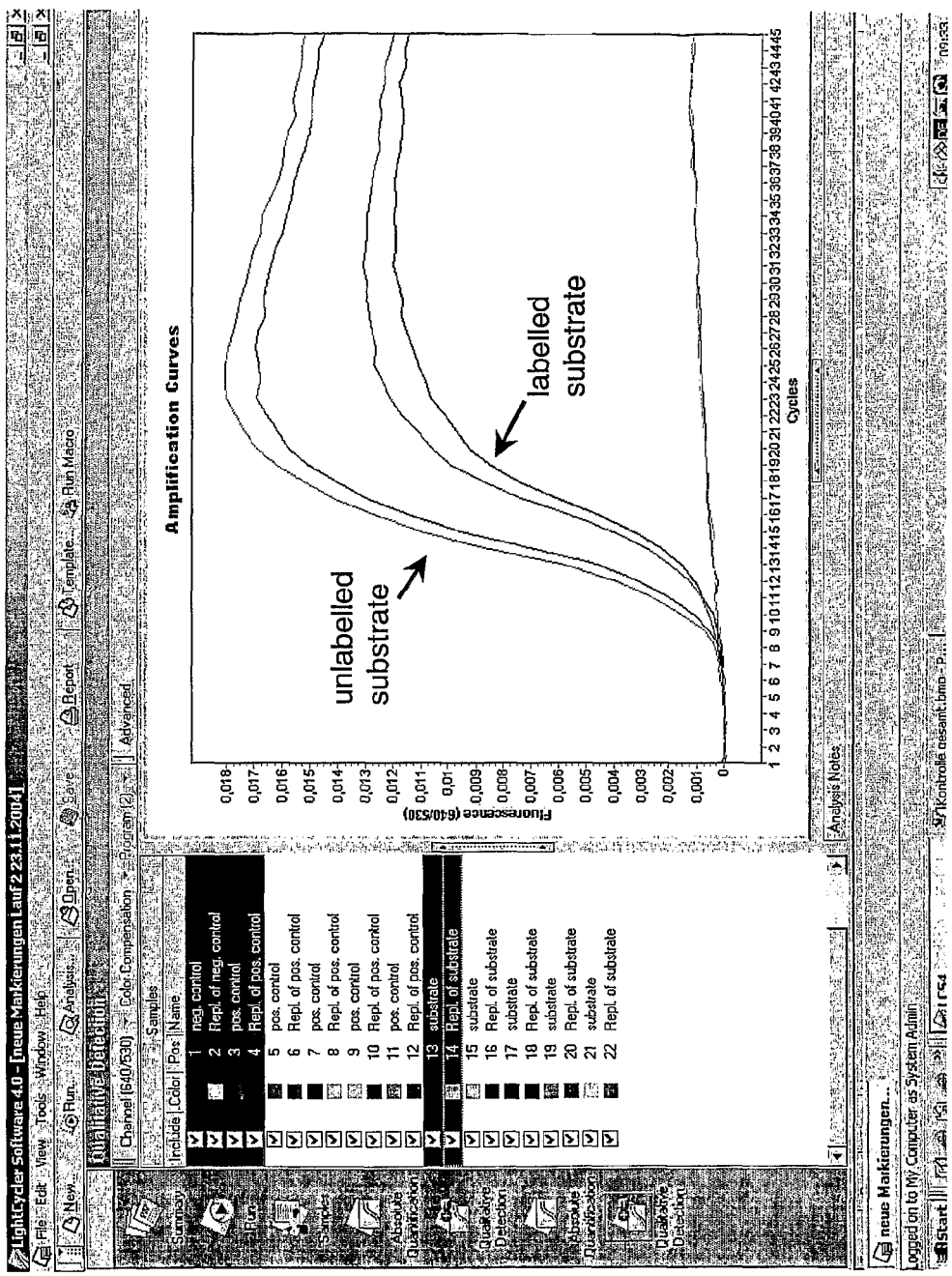
FIG. 10: Comparison of unlabelled and Aziridine-labelled DNA substrate by LightCycler-PCR (A=1.5 ng template DNA); (B=150 pg template DNA); (C=15 pg template DNA); (D=1.5 pg template DNA).
Figure 10B:
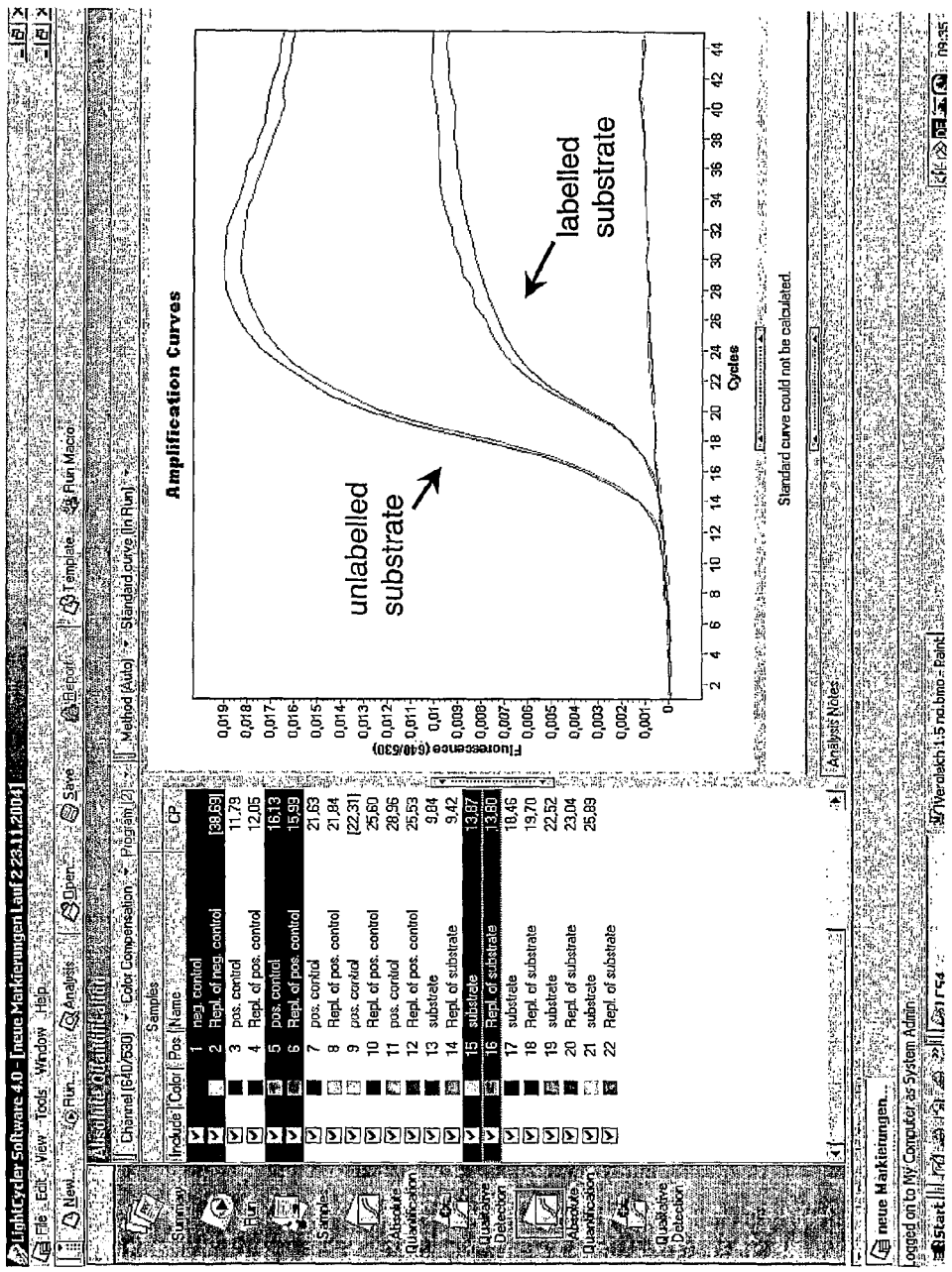
Figure 10C:
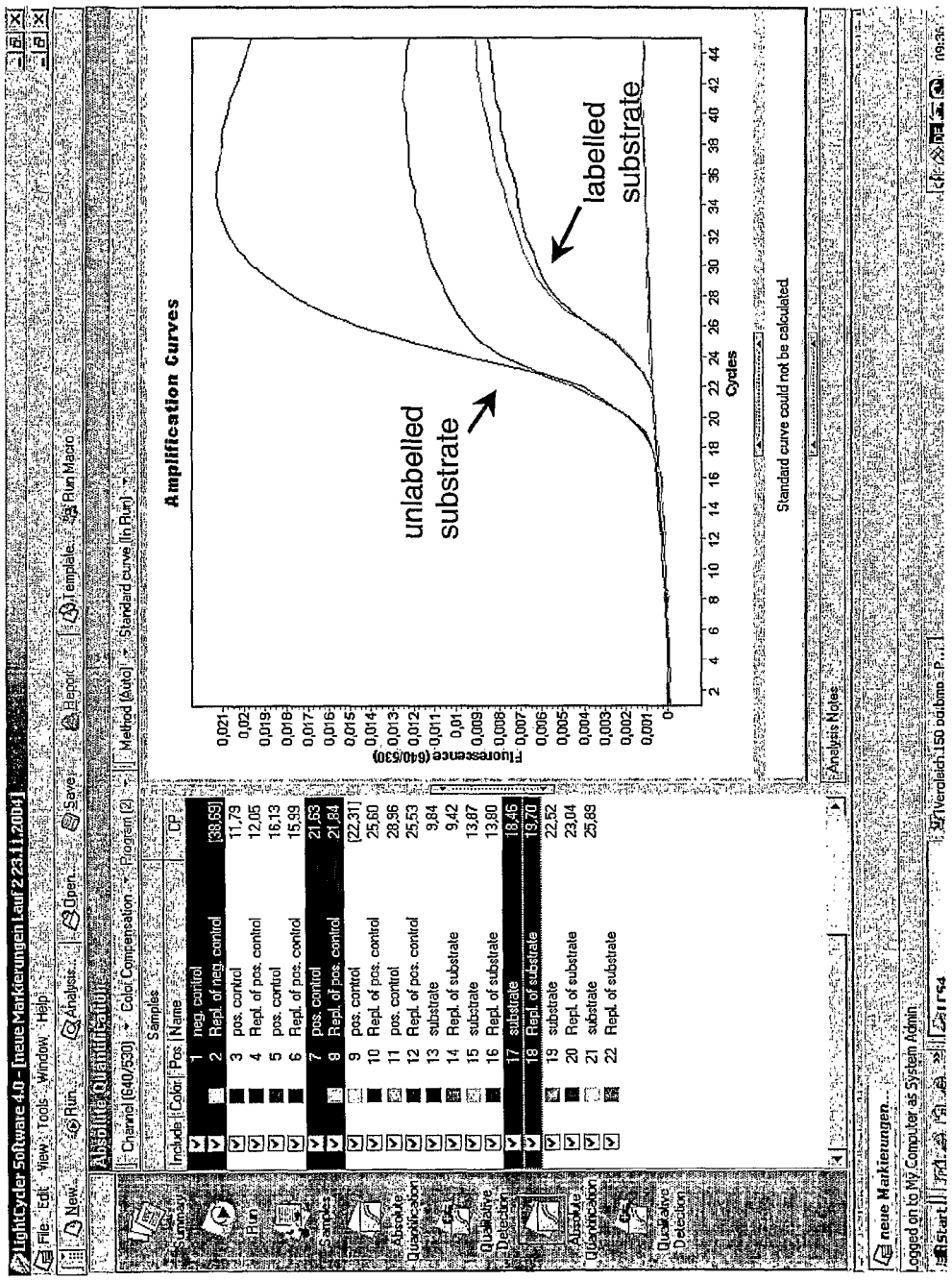
Figure 10D:
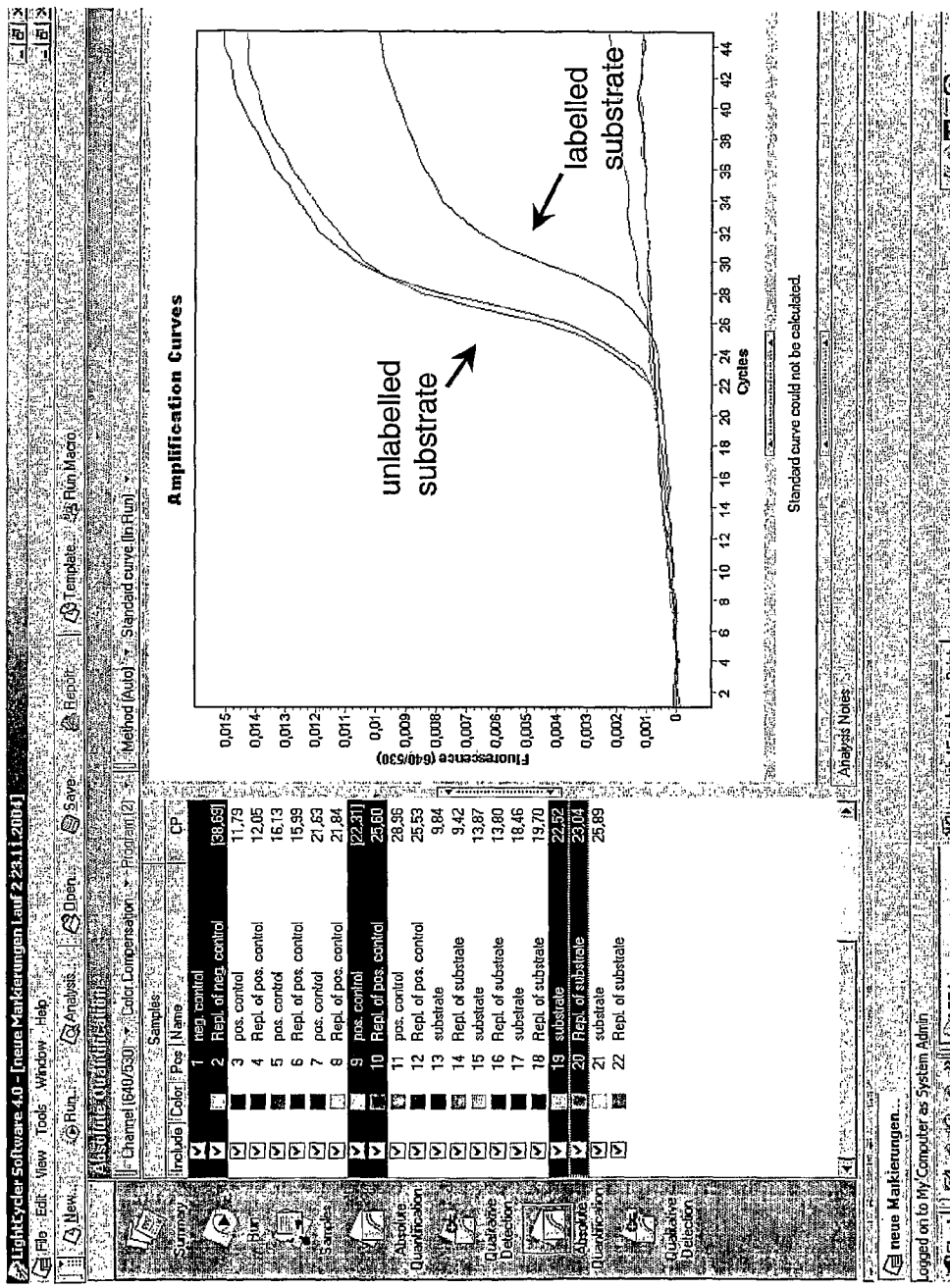

In the subsequent labelling experiments both non-methylated and (for control purposes) methylated substrate were used. In order to prepare completely or partially methylated DNA substrate, the DNA was incubated with the methylases M.SssI (recognition sequence CG), M.HhaI (recognition sequence GCGC) and M.HpaII (recognition sequence CCGG) using the natural methyl group donor S-adenosyl methionine (SAM) in accordance with the manufacturer's instructions. A subsequent examination of the complete methylation or purification was carried out by the use of the corresponding restriction endonuclease HhaI and HpaII (methylated sequences are not hydrolyzed) (FIG. 9A) and subsequent purification by means of a preparative agarose gel electrophoresis (FIG. 9B).

(C) LABELLING OF THE DNA SUBSTRATES

In order to examine the "road block" concept, first of all only non-methylated substrate was used for labelling with the aziridine derivative 7-BAz (for experimental details as to the labelling with 7-BAz see above, Example 6). The correspondingly treated DNA substrates were subsequently transferred back to the RCD for control purposes in the LightCycler.

(D) EXAMINATION OF THE LABELLED DNA SUBSTRATES IN THE LIGHTCYCLER

In order to examine the possible influence of 7-BAz labelling on the polymerase reaction, correspondingly labelled DNA as well as two unlabelled controls were tested in real-time PCR reactions in a LightCycler. In this context, the DNA substrate was diluted in advance used in dilution degrees of 1.5 ng, 150 pg, 15 pg, 1.5 pg and 150 fg DNA per reaction batch. All PCR batches were analyzed twice, respectively. For amplification or detection the following primer/probe pairs were used:

```
forward primer:                     (SEQ ID NO: 4)
5'-GACCTGGGAAAGAGGGAAAGGC-3' reverse primer:                     (SEQ ID NO: 5)
 5'-CTGCGGGTTGGCCCCATGC-3' hyb-probe:                          (SEQ ID NO: 6)
 5'-LC Red640-GGCGCAGCGGGGCGGG-3' fluorescein-probe:                  (SEQ ID NO: 7)
 5'-CGCCGTGACTCAGCACT-fluorescein-3'
```

Moreover, in preliminary tests an optimum MgCl$_2$ concentration of 2 mM could be determined. All PCR reactions in the LightCycler were carried out using the "FastStart DNA Master Hybridization Probes" kit (Roche, order no. 2 239 272) in accordance with the manufacturer's instructions.

Respective Reaction Batches:

| | | |
|---|---|---|
| H$_2$O, PCR-grade | 7.2 µl | — |
| MgCl$_2$ stock sol. | 0.8 µl | 2 mM |
| forward primer | 2.0 µl | 5 µM |
| reverse primer | 2.0 µl | 5 µM |
| Hyb-probe | 2.0 µl | 0.3 µM |
| fluorescein probe | 2.0 µl | 0.3 µM |
| FastStart Mix | 2.0 µl | — |
| DNA template | 2.0 µl | (150 fg to 1.5 ng) |

As a negative control for the PCR reaction, a batch (double determination) using H$_2$O, PCR-grade rather than the DNA template was used.

LightCycler Program:

| 1. "pre-incubation" | 10 min 95° C. | |
|---|---|---|
| 2. "amplification" | 15 sec 95° C. | |
| | 15 sec 58° C. | } 45 cycles |
| | 15 sec 72° C. | |
| 3. "cooling" | 1 min 37° C. | |

After each run the evaluation was carried out using the "LightCycler Software 4.0". By means of the latter, the fluorescence signals detected during the PCR are converted into so-called "crossing points". This makes it possible to draw conclusions on the amplification course or the efficiency of the polymerase reaction.

(E) RESULTS AND CONCLUSION

The real time-PCR using the LightCycler as described above was repeated in several reproduction batches. When comparing the respective batches, it could be shown that the reaction course was slower when the aziridine-labelled DNA substrate was used (i.e. later "crossing points") than with the controls using unlabelled DNA template (FIGS. 10A-D). This means that the polymerase reaction was slowed down by the aziridine labelled bases of the non-methylated DNA substrate.

In summary, the present experimental results clearly demonstrate that the "road block" concept can be used for differentiating between non-methylated and methylated DNA.

The invention claimed is:

1. A method for detecting sequence specific methylation in a biomolecule having a recognition site for an AdoMet, comprising:
   (a) contacting a biomolecule with an S-adenosyl-L-methionine-dependent methyltransferase in the presence of a detectable cofactor of said methyltransferase; and
   (b) detecting whether the recognition site of said methyltransferase has been modified with the cofactor, wherein modification of the recognition site is indicative of an absence of methylation at said recognition site;
   wherein the cofactor is an N-adenosylaziridine derivative represented by formula (I),

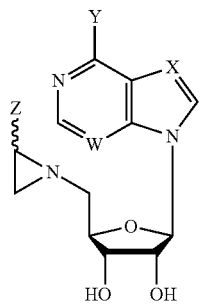

wherein
W is selected from N and CH,
X is N or $CR^1$,
Y is $NH_2$ or $NHR^2$,
Z is H, $R^3$ or $CH_2CH(COOH)(NH_2)$,
with the proviso that
if X is $CR^1$, Y is $NH_2$ and Z is H or $CH_2CH(COOH)(NH_2)$,
if X is N and Y is $NHR^2$, Z is H or $CH_2CH(COOH)(NH_2)$,
if X is N and Y is $NH_2$, Z is $R^3$,
$R^1$ is selected from $-(CH_2)_nR^4$, $-(CH=CH)_m(CH_2)_nR^4$, $-(CH_2)_o(CH=CH)_m(CH_2)_nR^4$, $-(C\equiv C)_m(CH_2)_nR^4$, $-(C\equiv C)_m(C_6H_4)_o(CH_2)_nR^4$, $-(C_6H_4)_m(CH_2)_nR^4$, $-CO(CH_2)_nR^4$ and $-S(CH_2)_nR^4$;
$R^2$ is selected from $-(CH_2)_nR^4$, $-(C_6H_4)_m(CH_2)_nR^4$ and $-CO(CH_2)_nR^4$;
$R^3$ is selected from $-(CH_2)_nR^4$, $-(CH=CH)_m(CH_2)_mR^4$, $-(C\equiv C)_m(CH_2)_nR^4$, $-(C_6H_4)_m(CH_2)_nR^4$ and $-CONH(CH_2)_nR^4$;
$R^4$ is selected from $-NHR^5$, $-NHCO(CH_2)_pSR^5$, $-SR^5$, $-OR^5$, $-O(C_2H_5O)_n(C_2H_5)NHR^5$, $-CH_2NHNHR^5$, $-NHCOCH(CH_2SH)NHR^5$ and $-CONHR^5$;
$R^5$ is selected from fluorophores, affinity tags, crosslinking agents, chromophors, proteins, peptides, amino acids which may optionally be modified, nucleotides, nucleosides, nucleic acids, carbohydrates, lipids, PEG, transfection reagents, beads, intercalating agents, nucleic acid cleaving reagents and nanoparticles;
n, m, o and p are independently selected from 0 or an integer from 1 to 5000.

2. The method of claim 1, wherein said biomolecule is a nucleic acid molecule or a (poly)peptide.

3. The method of claim 1, wherein step (a) is performed in vitro or with cell extracts.

4. The method of claim 2, wherein said nucleic acid molecule is DNA.

5. The method of claim 4, further comprising prior to step (a) a step of treating the DNA with a restriction enzyme.

6. The method of claim 4, wherein the DNA molecule is immobilized on a solid support.

7. The method of claim 6, wherein the DNA molecule is coupled to the solid support by hybridizing the DNA molecule to an oligonucleotide which is attached to said solid support.

8. The method of claim 1, wherein the methyltransferase is an orphan DNA methyltransferase or part of a bacterial restriction modification system.

9. The method of claim 8, wherein the methyltransferase is selected from the group consisting of M.HhaI, M.TaqI, M.BseCI and M.SssI.

10. The method of claim 1, wherein
    (a) the N-adenosylaziridine derivative of formula (I) blocks restriction enzyme cleavage at the recognition site of the DNA methyltransferase; and
    (b) methylation is detected by testing whether the modification of the DNA by the N-adenosylaziridine derivative blocks cleavage mediated by a restriction enzyme at said recognition site.

11. The method of claim 1, wherein
    (a) the N-adenosylaziridine derivative of formula (I) interferes with nucleic acid amplification at the recognition site of the methyltransferase; and
    (b) methylation is detected by testing whether amplification of the nucleic acid molecule at the recognition site of the methyltransferase has been retarded.

12. The method of claim of claim 1, wherein
    (a) the N-adenosylaziridine derivative of formula (I) contains a fluorescent label; and
    (b) methylation is detected by measuring the presence or amount of fluorescence in said nucleic acid molecule.

13. The method of claim of claim 1, wherein
    (a) nucleic acid molecules modified at the methyltransferase recognition site are purified by affinity purification; and
    (b) the N-adenosylaziridine derivative of formula (I) contains an affinity tag.

14. The method of claim 1, wherein the N-adenosylaziridine derivative of formula (I) is added to a cytosine residue and cannot be added to a 5-methylcytosine residue in DNA.

15. The method of claim 1, comprising after step (a) an additional step of sequencing the DNA molecule.

16. The method of claim 1, wherein said detectable cofactor is detected by (a) an antibody specifically binding to said detectable cofactor or by (b) avidin or streptavidin specifically binding to said detectable cofactor.

17. The method of claim 1, wherein the identity of said DNA molecule is determined by DNA sequencing, hybridization, Maldi-T of or analysis of nucleoside composition by enzymatic fragmentation and chromatography.

18. The method of claim 1, wherein the N-adenosylaziridine derivative is selected from the group consisting of

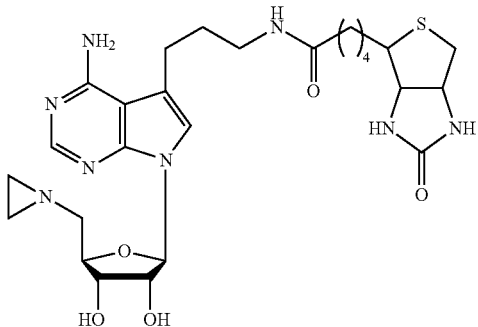

1

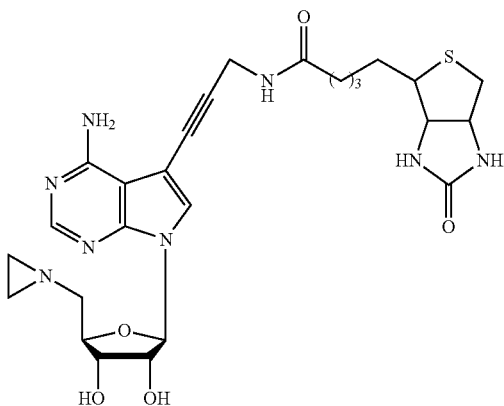

2

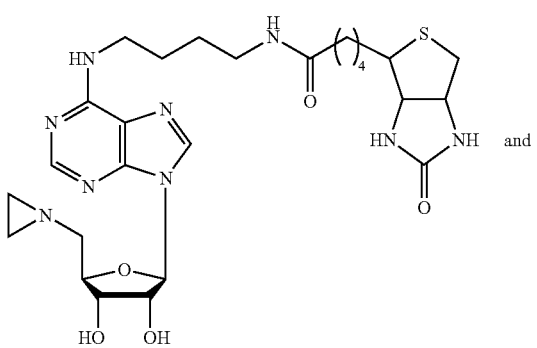

3 and

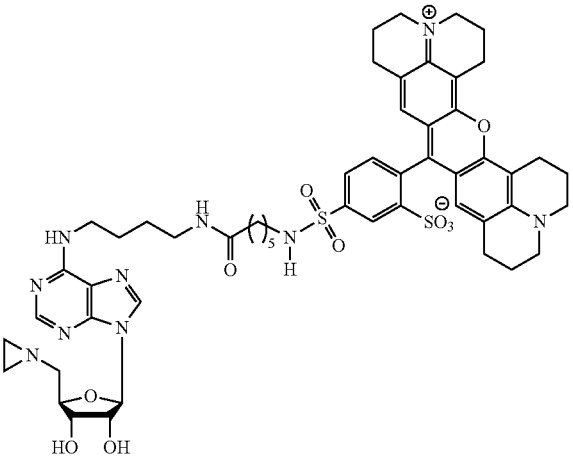

4

19. The method of claim 10, wherein the N-adenosylaziridine derivative is

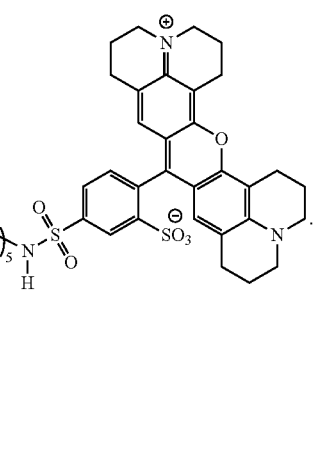

4

20. A compound of formula (I)

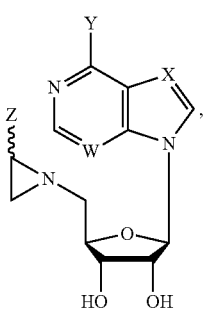

(I)

wherein
W is N or CH,
X is N or CR$^1$,
Y is NH$_2$ or NHR$^2$,
Z is H, R$^3$ or CH$_2$CH(COOH)(NH$_2$), with the proviso that
if X is CR$^1$, Y is NH$_2$ and Z is H or CH$_2$CH(COOH)(NH$_2$),
if X is N and Y is NHR$^2$, Z is H or CH$_2$CH(COOH)(NH$_2$),
if X is N and Y is NH$_2$, Z is R$^3$, R$^1$ is —(CH$_2$)$_n$R$^4$, —(CH=CH)$_m$(CH$_2$)$_n$R$^4$, —(CH$_2$)$_o$(CH=CH)$_m$(CH$_2$)$_n$R$^4$, —(C≡C)$_m$(CH$_2$)$_n$R$^4$, —(C≡C)$_m$(C$_6$H$_4$)$_o$(CH$_2$)$_n$R$^4$, —(C$_6$H$_4$)$_m$(CH$_2$)$_n$R$^4$, —CO(CH$_2$)$_n$R$^4$ or —S(CH$_2$)$_n$R$^4$;

R$^2$ is —(CH$_2$)$_n$R$^4$, —(C$_6$H$_4$)$_m$(CH$_2$)$_n$R$^4$—CO(C$_6$H$_4$)$_m$(CH$_2$)$_n$R$^4$ or —CO(CH$_2$)$_n$R$^4$;

R$^3$ is —(CH$_2$)$_n$R$^4$, —(CH=CH)$_m$(CH$_2$)$_n$R$^4$, —(C≡C)$_m$(CH$_2$)$_n$R$^4$, —(C$_6$H$_4$)$_m$(CH$_2$)$_n$R$^4$ or —CONH(CH$_2$)$_n$R$^4$;

R$^4$ is —NHR$^5$, —NHCO(CH$_2$)$_p$SR$^5$, —SR$^5$, —OR$^5$, —O(C$_2$H$_5$O)$_p$(C$_2$H$_5$)NHR$^5$, —CH$_2$NHNHR$^5$, —NHCOCH(CH$_2$SH)NHR$^5$ or —CONHR$^5$;

R$^5$ is selected from the group consisting of fluorophores, affinity tags, crosslinking agents, chromophors, proteins, peptides, amino acids which may optionally be modified, nucleotides, nucleosides, nucleic acids, carbohydrates, lipids, PEG, transfection reagents, beads, intercalating agents, nucleic acid cleaving reagents and nanoparticles and n, m, o and p are independently 0 or an integer from 1 to 5000.

21. The compound of claim 20, wherein said fluorophore is Alexa, BODIPY, coumarin, dansyl, fluorescein, mansyl, pyrene, rhodamine, Texas red, TNS, or a cyanine fluorophore or a derivative thereof.

22. The compound of claim 20, wherein said affinity tag is a peptide tag, biotin, nickel-nitrilotriacetic acid (NTA), maltose, digoxygenin or dinitrophenol.

23. The compound of claim 22, wherein said peptide tag is his-tag or a tag with metal chelating properties, strep-tag, flag-tag, c-myc-tag, HA-tag, epitopes or glutathione.

24. The compound of claim 20, wherein said crosslinking agent is maleimide, iodacetamide or a derivative thereof, or an aldehyde derivative, or a photocrosslinking agent.

25. The compound of claim 24 wherein said photocrosslinking agent is arylazide, a diazo compound, psoralen or a benzophenone compound.

26. The compound of claim 20, wherein said nucleic acid cleaving reagent is iron-EDTA, acridine or a derivative thereof or a rhodium complex.

27. The compound of claim 20, which is

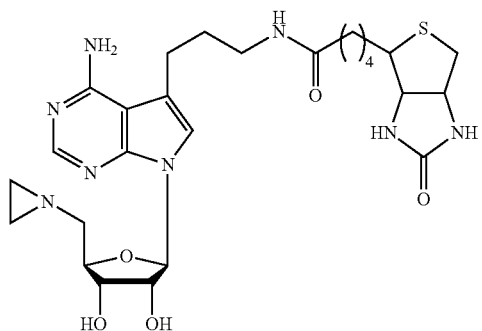

1

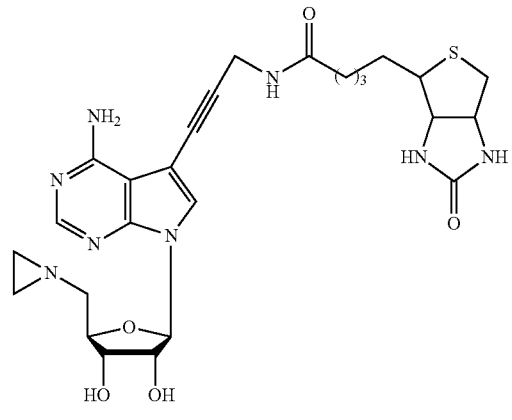

2

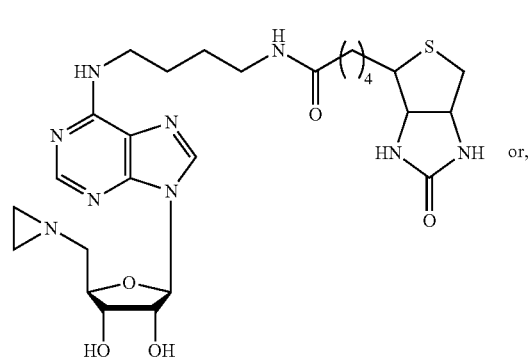

3

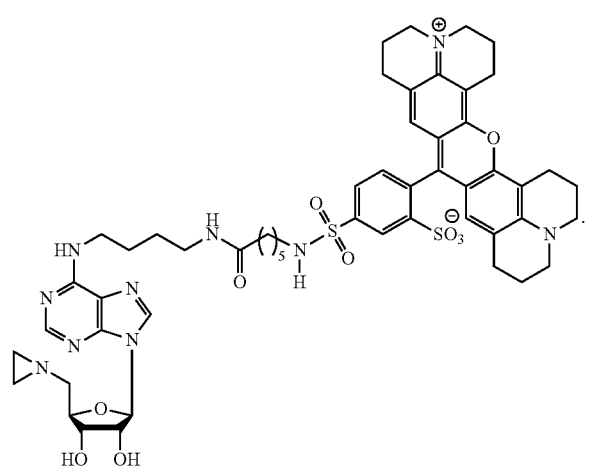

4

28. A complex of a compound according to claim 20 and an S-adenosyl-L-methionine (AdoMet)-dependent methyltransferase.

29. The complex of claim 28, wherein said methyltransferase normally transfers the methyl residue of S-adenosyl-L-methionine (AdoMet) onto a nucleic acid molecule or a (poly)peptide.

30. The complex of claim 28, wherein said methyltransferase is an orphan DNA methyltransferase or part of a restriction modification system of a bacterium.

31. The complex of claim 28, wherein the methyltransferase is selected from the group consisting of the DNA methyltransferases M.HhaI, M.TaqI, M.BseCI and M.SssI.

32. A kit comprising a compound of claim 20 and a methyltransferase which uses AdoMet as a cofactor in vivo, or a complex of the compound and the methyltransferase in a suitable container.

33. A pharmaceutical composition comprising the compound of claim 20 or a complex of the compound and a methyltransferase which use AdoMet as a cofactor in vivo, and a pharmaceutically acceptable carrier.

34. The method of claim 1, wherein step (a) is performed in vivo.

* * * * *